United States Patent
Schaefer et al.

(10) Patent No.: US 10,426,655 B2
(45) Date of Patent: *Oct. 1, 2019

(54) THERMAL CONTRAST THERAPY DEVICES, METHODS, AND SYSTEMS

(71) Applicant: CASCADE WELLNESS TECHNOLOGIES, INC., Sunriver, OR (US)

(72) Inventors: David Schaefer, Sunriver, OR (US); Richard Smith, Sunriver, OR (US)

(73) Assignee: CASCADE WELLNESS TECHNOLOGIES, INC., Sunriver, OH (US)

( * ) Notice: Subject to any disclaimer, the term of this patent is extended or adjusted under 35 U.S.C. 154(b) by 545 days.

This patent is subject to a terminal disclaimer.

(21) Appl. No.: 15/147,109

(22) Filed: May 5, 2016

(65) Prior Publication Data
US 2016/0242957 A1 Aug. 25, 2016

Related U.S. Application Data

(63) Continuation of application No. 14/682,295, filed on Apr. 9, 2015, now Pat. No. 9,345,614.
(Continued)

(51) Int. Cl.
*A61F 7/00* (2006.01)
*A61F 7/02* (2006.01)

(52) U.S. Cl.
CPC ............... *A61F 7/007* (2013.01); *A61F 7/00* (2013.01); *A61F 7/0085* (2013.01);
(Continued)

(58) Field of Classification Search
CPC combination set(s) only.
See application file for complete search history.

(56) References Cited

U.S. PATENT DOCUMENTS

| 4,459,468 A | 7/1984 | Bailey |
| 4,585,002 A | 4/1986 | Kissin |

(Continued)

FOREIGN PATENT DOCUMENTS

| GB | 962716 | 7/1964 |
| WO | 2013013059 | 1/2013 |

OTHER PUBLICATIONS

US 8,655,442 B2, 02/2014, Flint (withdrawn)
(Continued)

*Primary Examiner* — Joseph A Stoklosa
*Assistant Examiner* — Adam J Avigan
(74) *Attorney, Agent, or Firm* — Leber IP Law; Celia H. Leber

(57) ABSTRACT

The present disclosure relates to thermal contrast therapy devices, treatment methods for providing thermal contrast therapy, and systems for providing and managing thermal contrast therapy treatments. The thermal contrast therapy devices disclosed herein are configured to provide a sequence of alternating cooling periods and heating periods to one or more areas of a patient's body. A thermal contrast therapy device may comprise a source of hot fluid, a source of cold fluid, and one or more pumps configured to circulate fluid through one or more treatment pads in fluid communication with the device. The thermal contrast therapy devices disclosed herein are configured to rapidly and efficiently transition between alternating cooling periods and heating periods.

23 Claims, 33 Drawing Sheets

Related U.S. Application Data

(60) Provisional application No. 62/028,952, filed on Jul. 25, 2014.

(52) U.S. Cl.
CPC ............ *A61F 2007/0027* (2013.01); *A61F 2007/0042* (2013.01); *A61F 2007/0054* (2013.01); *A61F 2007/0056* (2013.01); *A61F 2007/0076* (2013.01); *A61F 2007/0086* (2013.01); *A61F 2007/0093* (2013.01); *A61F 2007/0094* (2013.01); *A61F 2007/0096* (2013.01); *A61F 2007/0225* (2013.01); *A61F 2007/0282* (2013.01); *A61F 2007/0295* (2013.01); *A61F 2007/0296* (2013.01)

(56) References Cited

U.S. PATENT DOCUMENTS

| | | |
|---|---|---|
| 4,691,762 A | 9/1987 | Elkins |
| 4,844,072 A | 7/1989 | French et al. |
| 5,051,562 A | 9/1991 | Bailey et al. |
| 5,080,089 A | 1/1992 | Mason et al. |
| 5,128,517 A | 7/1992 | Bailey et al. |
| 5,241,951 A | 9/1993 | Mason et al. |
| 5,411,541 A | 5/1995 | Bell et al. |
| 5,449,379 A | 9/1995 | Hadtke |
| 5,683,438 A | 11/1997 | Grahn |
| 5,711,155 A | 1/1998 | DeVilbiss et al. |
| 5,865,841 A | 2/1999 | Kolen et al. |
| 5,871,526 A | 2/1999 | Gibbs et al. |
| 5,948,012 A | 9/1999 | Mahaffey et al. |
| 5,980,561 A | 11/1999 | Kolen et al. |
| 6,149,670 A | 11/2000 | Worthen et al. |
| 6,149,674 A | 11/2000 | Borders |
| 6,361,496 B1 | 3/2002 | Zikorus et al. |
| 6,383,184 B1 | 5/2002 | Sharkey |
| 6,409,691 B1 | 6/2002 | Dakin et al. |
| 6,551,347 B1 * | 4/2003 | Elkins ............... A61F 7/0085 165/46 |
| 6,551,348 B1 | 4/2003 | Blalock et al. |
| 6,589,267 B1 | 7/2003 | Hui |
| 6,620,187 B2 | 9/2003 | Carson et al. |
| 6,645,232 B2 | 11/2003 | Carson |
| 6,660,027 B2 | 12/2003 | Gruszecki et al. |
| 6,692,518 B2 | 2/2004 | Carson |
| 6,699,267 B2 | 3/2004 | Voorhees et al. |
| 6,818,012 B2 | 11/2004 | Ellingboe |
| 7,087,075 B2 | 8/2006 | Briscoe et al. |
| 7,211,104 B2 | 5/2007 | Edelman |
| 7,306,568 B2 | 12/2007 | Diana |
| 7,476,242 B2 | 1/2009 | Matlock |
| 7,694,693 B1 | 4/2010 | Edelman et al. |
| 7,828,831 B1 | 11/2010 | Tanhelco et al. |
| 7,931,028 B2 | 4/2011 | Jay |
| 8,097,030 B2 | 1/2012 | Stelea et al. |
| 8,206,414 B2 | 6/2012 | Horvat |
| 8,216,290 B2 | 7/2012 | Shawver et al. |
| 8,226,293 B2 | 7/2012 | Faries et al. |
| 8,226,698 B2 | 7/2012 | Edelman et al. |
| 8,425,579 B1 | 4/2013 | Edelman et al. |
| 8,491,644 B1 | 7/2013 | Carson et al. |
| 8,613,762 B2 | 12/2013 | Bledsoe |
| 8,647,374 B2 | 2/2014 | Koewler |
| 8,647,375 B2 | 2/2014 | Woodall |
| 8,690,934 B2 | 4/2014 | Boyden et al. |
| 8,753,383 B2 | 6/2014 | Parish et al. |
| 9,113,895 B2 | 8/2015 | McEwen et al. |
| 2003/0078640 A1 | 4/2003 | Carson et al. |
| 2004/0015217 A1 | 1/2004 | Lofgren |
| 2004/0068310 A1 * | 4/2004 | Edelman ............... A61F 7/02 607/104 |
| 2008/0077211 A1 | 3/2008 | Levinson et al. |
| 2014/0277302 A1 * | 9/2014 | Weber ............... A61F 7/0085 607/104 |

OTHER PUBLICATIONS

SS Growler TM, The Stainless Steel Growler, Single bale design, elastomeric seal Non-repressurizable: only for storing short term 2L, http://www.brewsuit.com/stainless-steel-growler.php (admitted prior art).

The Brauler Modular Growler System: Food grade SS (18/8), 2L single walled Screw//threaded lid design, FreshCap: accessory CO2 cap keeps the beer freshly carbonated longer, http://thezythosproject.com (admitted prior art).

HlydroFlask: 64 oz Wide Mouth Vacuum Insulated Stainless Steel Growler, http://www.hydroflask.com/products/64-oz-wide-mouth-vacuum-insulated-stainless-steel-growler.html (admitted prior art).

The uKeg Pressurized Growler for Fresh Beer, Kickstarter, 2016, https://www.kickstarter.com/projects/growlerwerks/the-ukegtm-pressurized-growler-for-fresh-beer/description.

* cited by examiner

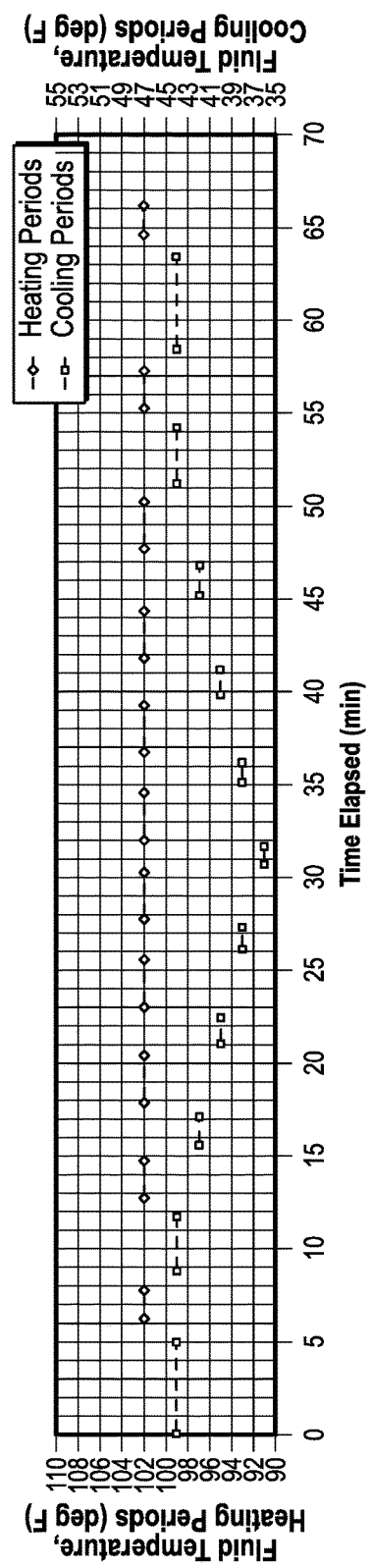

| Period | Start Time (min) | End Time (min) | Duration (min) | Time Elapsed (min) | Fluid Temp (°F) | Period | Start Time (min) | End Time (min) | Duration (min) | Time Elapsed (min) | Fluid Temp (°F) | Period | Start Time (min) | End Time (min) | Duration (min) | Time Elapsed (min) | Fluid Temp (°F) |
|---|---|---|---|---|---|---|---|---|---|---|---|---|---|---|---|---|---|
| C1 | 0 | 5 | 5 | 5 | | T8 | 25.5 | 26 | 0.5 | 26 | | T16 | 44.3 | 45.1 | 0.8 | 45.1 | |
| T1 | 5 | 6.2 | 1.2 | 6.2 | 44 | C5 | 26 | 27.2 | 1.2 | 27.2 | 38 | C9 | 45.1 | 46.9 | 1.8 | 46.9 | 42 |
| H1 | 6.2 | 7.7 | 1.5 | 7.7 | 102 | T9 | 27.2 | 27.7 | 0.5 | 27.7 | | T17 | 46.9 | 47.7 | 0.8 | 47.7 | |
| T2 | 7.7 | 8.7 | 1 | 8.7 | 44 | H5 | 27.7 | 30.2 | 2.5 | 30.2 | 102 | H9 | 47.7 | 50.2 | 2.5 | 50.2 | 102 |
| C2 | 8.7 | 11.7 | 3 | 11.7 | | T10 | 30.2 | 30.6 | 0.4 | 30.6 | | T18 | 50.2 | 51.2 | 1 | 51.2 | |
| T3 | 11.7 | 12.7 | 1 | 12.7 | 44 | C6 | 30.6 | 31.6 | 1 | 31.6 | 36 | C10 | 51.2 | 54.2 | 3 | 54.2 | 44 |
| H2 | 12.7 | 14.7 | 2 | 14.7 | 102 | T11 | 31.6 | 32 | 0.4 | 32 | | T19 | 54.2 | 55.2 | 1 | 55.2 | |
| T4 | 14.7 | 15.5 | 0.8 | 15.5 | 42 | H6 | 32 | 34.5 | 2.5 | 34.5 | 102 | H10 | 55.2 | 57.2 | 2 | 57.2 | 102 |
| C3 | 15.5 | 17.1 | 1.6 | 17.1 | | T12 | 34.5 | 35 | 0.5 | 35 | | T20 | 57.2 | 58.4 | 1.2 | 58.4 | |
| T5 | 17.1 | 17.9 | 0.8 | 17.9 | 42 | C7 | 35 | 36.2 | 1.2 | 36.2 | 38 | C11 | 58.2 | 63.4 | 5 | 63.4 | 44 |
| H3 | 17.9 | 20.4 | 2.5 | 20.4 | 102 | T13 | 36.2 | 36.7 | 0.5 | 36.7 | | T21 | 63.4 | 64.6 | 1.2 | 64.6 | |
| T6 | 20.4 | 21 | 0.6 | 21 | | H7 | 36.7 | 39.2 | 2.5 | 39.2 | 102 | H11 | 64.6 | 66.1 | 1.5 | 66.1 | 102 |
| C4 | 21 | 22.4 | 1.4 | 22.4 | 40 | T14 | 39.2 | 39.8 | 0.6 | 39.8 | | | | | | | |
| T7 | 22.4 | 23 | 0.6 | 23 | | C8 | 39.8 | 41.2 | 1.4 | 41.2 | 40 | | | | | | |
| H4 | 23 | 25.5 | 2.5 | 25.5 | 102 | T15 | 41.2 | 41.8 | 0.6 | 41.8 | | | | | | | |
| | | | | | | H8 | 41.8 | 44.3 | 2.5 | 44.3 | 102 | | | | | | |

C = Cooling Period; H = Heating Period; T = Transition Period

FIG. 14A-2

| Period | Start Time (min) | End Time (min) | Duration (min) | Time Elapsed (min) | Fluid Temp (°F) | Period | Start Time (min) | End Time (min) | Duration (min) | Time Elapsed (min) | Fluid Temp (°F) | Period | Start Time (min) | End Time (min) | Duration (min) | Time Elapsed (min) | Fluid Temp (°F) |
|---|---|---|---|---|---|---|---|---|---|---|---|---|---|---|---|---|---|
| H1 | 0 | 5 | 5 | 5 | 100 | T8 | 29.1 | 30.2 | 1.1 | 30.2 | 106 | T16 | 51.6 | 52.7 | 1.1 | 52.7 | |
| T1 | 5 | 6.4 | 1.4 | 6.4 | | H5 | 30.2 | 32.6 | 2.4 | 32.6 | | H9 | 52.7 | 55.5 | 2.8 | 55.5 | 102 |
| C1 | 6.4 | 8.4 | 2 | 8.4 | 50 | T9 | 32.6 | 33.6 | 1 | 33.6 | | T17 | 55.5 | 56.7 | 1.2 | 56.7 | |
| T2 | 8.4 | 9.8 | 1.4 | 9.8 | | C5 | 33.6 | 34.8 | 1.2 | 34.8 | 42 | C9 | 56.7 | 58.3 | 1.6 | 58.3 | 46 |
| H2 | 9.8 | 12.8 | 3 | 12.8 | 100 | T10 | 34.8 | 35.8 | 1 | 35.8 | | T18 | 58.3 | 59.5 | 1.2 | 59.5 | |
| T3 | 12.8 | 14.1 | 1.3 | 14.1 | | H6 | 35.8 | 38 | 2.2 | 38 | 108 | H10 | 59.5 | 62.5 | 3 | 62.5 | 100 |
| C2 | 14.1 | 15.9 | 1.8 | 15.9 | 48 | T11 | 38 | 38.9 | 0.9 | 38.9 | | T19 | 62.5 | 63.8 | 1.3 | 63.8 | |
| T4 | 15.9 | 17.2 | 1.3 | 17.2 | | C6 | 38.9 | 40 | 1.1 | 40 | 40 | C10 | 63.8 | 65.6 | 1.8 | 65.6 | 48 |
| H3 | 17.2 | 20 | 2.8 | 20 | 102 | T12 | 40 | 40.9 | 0.9 | 40.9 | | T20 | 65.6 | 66.9 | 1.3 | 66.9 | |
| T5 | 20 | 21.2 | 1.2 | 21.2 | | H7 | 40.9 | 43.3 | 2.4 | 43.3 | 106 | H11 | 66.9 | 71.9 | 5 | 71.9 | 100 |
| C3 | 21.2 | 22.8 | 1.6 | 22.8 | 46 | T13 | 43.3 | 44.3 | 1 | 44.3 | | T21 | 71.9 | 73.3 | 1.4 | 73.3 | |
| T6 | 22.8 | 24 | 1.2 | 24 | | C7 | 44.3 | 45.5 | 1.2 | 45.5 | 42 | C11 | 73.3 | 75.3 | 2 | 75.3 | 50 |
| H4 | 24 | 26.6 | 2.6 | 26.6 | 104 | T14 | 45.5 | 46.5 | 1 | 46.5 | | | | | | | |
| T7 | 26.6 | 27.7 | 1.1 | 27.7 | | H8 | 46.5 | 49.1 | 2.6 | 49.1 | 104 | | | | | | |
| C4 | 27.7 | 29.1 | 1.4 | 29.1 | 44 | T15 | 49.1 | 50.2 | 1.1 | 50.2 | | | | | | | |
| | | | | | | C8 | 50.2 | 51.6 | 1.4 | 51.6 | 44 | | | | | | |

C = Cooling Period; H = Heating Period; T = Transition Period

FIG. 14B-2

| Period | Start Time (min) | End Time (min) | Duration (min) | Time Elapsed (min) | Fluid Temp (°F) | Period | Start Time (min) | End Time (min) | Duration (min) | Time Elapsed (min) | Fluid Temp (°F) | Period | Start Time (min) | End Time (min) | Duration (min) | Time Elapsed (min) | Fluid Temp (°F) |
|---|---|---|---|---|---|---|---|---|---|---|---|---|---|---|---|---|---|
| H1 | 0 | 5 | 3 | 3 | | T8 | 21 | 21.5 | 0.5 | 19.5 | | T16 | 35.6 | 36.4 | 0.8 | 34.4 | |
| T1 | 5 | 6 | 1 | 4 | 112 | H5 | 21.5 | 23 | 1.5 | 21 | 116 | H9 | 36.4 | 38.4 | 2 | 36.4 | 114 |
| C1 | 6 | 7 | 1 | 5 | 38 | T9 | 23 | 23.5 | 0.5 | 21.5 | | T17 | 38.4 | 39.2 | 0.8 | 37.2 | |
| T2 | 7 | 8 | 1 | 6 | | C5 | 23.5 | 24.7 | 1.2 | 22.7 | 34 | C9 | 39.2 | 40.2 | 1 | 38.2 | 38 |
| H2 | 8 | 10 | 2 | 8 | 114 | T10 | 24.7 | 25.1 | 0.4 | 23.1 | | T18 | 40.2 | 41.2 | 1 | 39.2 | |
| T3 | 10 | 11 | 1 | 9 | | H6 | 25.1 | 26.6 | 1.5 | 24.6 | 118 | H10 | 41.2 | 43.2 | 2 | 41.2 | 114 |
| C2 | 11 | 12 | 1 | 10 | 38 | T11 | 26.6 | 27 | 0.4 | 25 | | T19 | 43.2 | 44.2 | 1 | 42.2 | |
| T4 | 12 | 12.8 | 0.8 | 10.8 | | C6 | 27 | 28.2 | 1.2 | 26.2 | 34 | C10 | 44.2 | 45.2 | 1 | 43.2 | 38 |
| H3 | 12.8 | 14.8 | 2 | 12.8 | 114 | T12 | 28.2 | 28.7 | 0.5 | 26.7 | | T20 | 45.2 | 46.2 | 1 | 44.2 | |
| T5 | 14.8 | 15.6 | 0.8 | 13.6 | | H7 | 28.7 | 30.2 | 1.5 | 28.2 | 118 | H11 | 46.2 | 48.2 | 2 | 46.2 | 114 |
| C3 | 15.6 | 16.6 | 1 | 14.6 | 38 | T13 | 30.2 | 30.7 | 0.5 | 28.7 | | T21 | 48.2 | 49.2 | 1 | 47.2 | |
| T6 | 16.6 | 17.2 | 0.6 | 15.2 | | C7 | 30.7 | 31.9 | 1.2 | 29.9 | 36 | C11 | 49.2 | 50.2 | 1 | 48.2 | 38 |
| H4 | 17.2 | 19.2 | 2 | 17.2 | 114 | T14 | 31.9 | 32.5 | 0.6 | 30.5 | | T22 | 50.2 | 51.2 | 1 | 49.2 | |
| T7 | 19.2 | 19.8 | 0.6 | 17.8 | | H8 | 32.5 | 34 | 1.5 | 32 | 116 | H12 | 51.2 | 54.2 | 3 | 52.2 | 112 |
| C4 | 19.8 | 21 | 1.2 | 19 | 36 | T15 | 34 | 34.6 | 0.6 | 32.6 | | | | | | | |
| | | | | | | C8 | 34.6 | 35.6 | 1 | 33.6 | 38 | | | | | | |

C = Cooling Period; H = Heating Period; T = Transition Period

FIG. 14C-2

| Period | Start Time (min) | End Time (min) | Duration (min) | Time Elapsed (min) | Fluid Temp (°F) | Period | Start Time (min) | End Time (min) | Duration (min) | Time Elapsed (min) | Fluid Temp (°F) | Period | Start Time (min) | End Time (min) | Duration (min) | Time Elapsed (min) | Fluid Temp (°F) |
|---|---|---|---|---|---|---|---|---|---|---|---|---|---|---|---|---|---|
| H1 | 0 | 5 | 3 | 3 | 80 | T8 | 21.8 | 23 | 1.2 | 21 | 80 | T16 | 41.8 | 43 | 1.2 | 41 | 80 |
| T1 | 5 | 6.2 | 1.2 | 4.2 | | H5 | 23 | 25 | 2 | 23 | | H9 | 43 | 45 | 2 | 43 | |
| C1 | 6.2 | 6.8 | 0.6 | 4.8 | 50 | T9 | 25 | 26.2 | 1.2 | 24.2 | 50 | T17 | 45 | 46.2 | 1.2 | 44.2 | 50 |
| T2 | 6.8 | 8 | 1.2 | 6 | | C5 | 26.2 | 26.8 | 0.6 | 24.8 | | C9 | 46.2 | 46.8 | 0.6 | 44.8 | |
| H2 | 8 | 10 | 2 | 8 | 80 | T10 | 26.8 | 28 | 1.2 | 26 | 80 | T18 | 46.8 | 48 | 1.2 | 46 | 80 |
| T3 | 10 | 11.2 | 1.2 | 9.2 | | H6 | 28 | 30 | 2 | 28 | | H10 | 48 | 50 | 2 | 48 | |
| C2 | 11.2 | 11.8 | 0.6 | 9.8 | 50 | T11 | 30 | 31.2 | 1.2 | 29.2 | 50 | T19 | 50 | 51.2 | 1.2 | 49.2 | 50 |
| T4 | 11.8 | 13 | 1.2 | 11 | | C6 | 31.2 | 31.8 | 0.6 | 29.8 | | C10 | 51.2 | 51.8 | 0.6 | 49.8 | |
| H3 | 13 | 15 | 2 | 13 | 80 | T12 | 31.8 | 33 | 1.2 | 31 | 80 | T20 | 51.8 | 53 | 1.2 | 51 | 80 |
| T5 | 15 | 16.2 | 1.2 | 14.2 | | H7 | 33 | 35 | 2 | 33 | | H11 | 53 | 55 | 2 | 53 | |
| C3 | 16.2 | 16.8 | 0.6 | 14.8 | 50 | T13 | 35 | 36.2 | 1.2 | 34.2 | 50 | T21 | 55 | 56.2 | 1.2 | 54.2 | 50 |
| T6 | 16.8 | 18 | 1.2 | 16 | | C7 | 36.2 | 36.8 | 0.6 | 34.8 | | C11 | 56.2 | 56.8 | 0.6 | 54.8 | |
| H4 | 18 | 20 | 2 | 18 | 80 | T14 | 36.8 | 38 | 1.2 | 36 | 80 | T22 | 56.8 | 58 | 1.2 | 56 | 80 |
| T7 | 20 | 21.2 | 1.2 | 19.2 | | H8 | 38 | 40 | 2 | 38 | | H12 | 58 | 61 | 3 | 59 | |
| C4 | 21.2 | 21.8 | 0.6 | 19.8 | 50 | T15 | 40 | 41.2 | 1.2 | 39.2 | 50 | | | | | | |
| | | | | | | C8 | 41.2 | 41.8 | 0.6 | 39.8 | 50 | | | | | | |

C = Cooling Period; H = Heating Period; T = Transition Period

FIG. 14D-2

| Period | Start Time (min) | End Time (min) | Duration (min) | Time Elapsed (min) | Rate of Heat Transfer (BTU) | Total Heat Transfer (BTU) | Period | Start Time (min) | End Time (min) | Duration (min) | Time Elapsed (min) | Rate of Heat Transfer (BTU) | Total Heat Transfer (BTU) | Period | Start Time (min) | End Time (min) | Duration (min) | Time Elapsed (min) | Rate of Heat Transfer (BTU) | Total Heat Transfer (BTU) |
|---|---|---|---|---|---|---|---|---|---|---|---|---|---|---|---|---|---|---|---|---|
| C1 | 0 | 5 | 5 | 5 | -11.7 | -58.3 | T8 | 2.5 | 3 | 0.5 | 26 | | | T16 | 2.5 | 3.3 | 0.8 | 45.1 | | |
| T1 | 5 | 6.2 | 1.2 | 6.2 | | | C5 | 3 | 4.2 | 1.2 | 27.2 | -13.2 | -15.8 | C9 | 3.3 | 5.1 | 1.8 | 46.9 | -12.2 | -21.9 |
| H1 | 6.2 | 7.7 | 1.5 | 7.7 | 3.1 | 4.6 | T9 | 4.2 | 4.7 | 0.5 | 27.7 | | | T17 | 5.1 | 5.9 | 0.8 | 47.7 | | |
| T2 | 7.7 | 8.7 | 1 | 8.7 | | | H5 | 4.7 | 7.2 | 2.5 | 30.2 | 3.0 | 7.6 | H9 | 5.9 | 8.4 | 2.5 | 50.2 | 3.0 | 7.6 |
| C2 | 8.7 | 11.7 | 3 | 11.7 | -11.7 | -35 | T10 | 7.2 | 7.6 | 0.4 | 30.6 | | | T18 | 8.4 | 9.4 | 1 | 51.2 | | |
| T3 | 11.7 | 12.7 | 1 | 12.7 | | | C6 | 7.6 | 8.6 | 1 | 31.6 | -13.7 | -13.7 | C10 | 9.4 | 12.4 | 3 | 54.2 | -11.7 | -35 |
| H2 | 12.7 | 14.7 | 2 | 14.7 | 3.1 | 6.1 | T11 | 8.6 | 9 | 0.4 | 32 | | | T19 | 12.4 | 13.4 | 1 | 55.2 | | |
| T4 | 14.7 | 15.5 | 0.8 | 15.5 | | | H6 | 9 | 11.5 | 2.5 | 34.5 | 3.0 | 7.6 | H10 | 13.4 | 15.4 | 2 | 57.2 | 3.1 | 6.1 |
| C3 | 15.5 | 17.1 | 1.6 | 17.1 | -12.2 | -19.5 | T12 | 11.5 | 12 | 0.5 | 35 | | | T20 | 15.4 | 16.6 | 1.2 | 58.4 | | |
| T5 | 17.1 | 17.9 | 0.8 | 17.9 | | | C7 | 12 | 13.2 | 1.2 | 36.2 | -13.2 | -15.8 | C11 | 16.6 | 21.6 | 5 | 63.4 | -11.7 | -58.3 |
| H3 | 17.9 | 20.4 | 2.5 | 20.4 | 3.0 | 7.6 | T13 | 13.2 | 13.7 | 0.5 | 36.7 | | | T21 | 21.6 | 22.8 | 1.2 | 64.6 | | |
| T6 | 20.4 | 21 | 0.6 | 21 | | | H7 | 13.7 | 16.2 | 2.5 | 39.2 | 3.0 | 7.6 | H11 | 22.8 | 24.3 | 1.5 | 66.1 | 3.1 | 4.6 |
| C4 | 21 | 22.4 | 1.4 | 22.4 | -12.7 | -17.8 | T14 | 16.2 | 16.8 | 0.6 | 39.8 | | | | | | | | | |
| T7 | 22.4 | 23 | 0.6 | 23 | | | C8 | 16.8 | 18.2 | 1.4 | 41.2 | -12.7 | -17.8 | | | | | | | |
| H4 | 23 | 25.5 | 2.5 | 25.5 | 3.0 | 7.6 | T15 | 18.2 | 18.8 | 0.6 | 41.8 | | | | | | | | | |
| | | | | | | | H8 | 18.8 | 21.3 | 2.5 | 44.3 | 3.0 | 7.6 | | | | | | | |

C = Cooling Period; H = Heating Period; T = Transition Period

FIG. 14E-2

| Period | Start Time (min) | End Time (min) | Duration (min) | Time Elapsed (min) | Rate of Heat Transfer (BTU) | Total Heat Transfer (BTU) | Period | Start Time (min) | End Time (min) | Duration (min) | Time Elapsed (min) | Rate of Heat Transfer (BTU) | Total Heat Transfer (BTU) | Period | Start Time (min) | End Time (min) | Duration (min) | Time Elapsed (min) | Rate of Heat Transfer (BTU) | Total Heat Transfer (BTU) |
|---|---|---|---|---|---|---|---|---|---|---|---|---|---|---|---|---|---|---|---|---|
| H1 | 0 | 5 | 5 | 5 | | | T8 | 29.1 | 30.2 | 1.1 | 30.2 | | | T16 | 51.6 | 52.7 | 1.1 | 52.7 | | |
| T1 | 5 | 6.4 | 1.4 | 6.4 | 2.5 | 12.7 | H5 | 30.2 | 32.6 | 2.4 | 32.6 | 4.0 | 9.7 | H9 | 52.7 | 55.5 | 2.8 | 55.5 | 3.0 | 8.5 |
| C1 | 6.4 | 8.4 | 2 | 8.4 | -10.2 | -20.3 | T9 | 32.6 | 33.6 | 1 | 33.6 | | | T17 | 55.5 | 56.7 | 1.2 | 56.7 | | |
| T2 | 8.4 | 9.8 | 1.4 | 9.8 | | | C5 | 33.6 | 34.8 | 1.2 | 34.8 | -12.2 | -14.6 | C9 | 56.7 | 58.3 | 1.6 | 58.3 | -11.2 | -17.9 |
| H2 | 9.8 | 12.8 | 3 | 12.8 | 2.5 | 7.6 | T10 | 34.8 | 35.8 | 1 | 35.8 | | | T18 | 58.3 | 59.5 | 1.2 | 59.5 | | |
| T3 | 12.8 | 14.1 | 1.3 | 14.1 | | | H6 | 35.8 | 38 | 2.2 | 38 | 4.5 | 10 | H10 | 59.5 | 62.5 | 3 | 62.5 | 2.5 | 7.6 |
| C2 | 14.1 | 15.9 | 1.8 | 15.9 | -10.7 | -19.2 | T11 | 38 | 38.9 | 0.9 | 38.9 | | | T19 | 62.5 | 63.8 | 1.3 | 63.5 | | |
| T4 | 15.9 | 17.2 | 1.3 | 17.2 | | | C6 | 38.9 | 40 | 1.1 | 40 | -12.6 | -13.9 | C10 | 63.8 | 65.6 | 1.8 | 65.6 | -10.7 | -19.2 |
| H3 | 17.2 | 20 | 2.8 | 20 | 3.0 | 8.5 | T12 | 40 | 40.9 | 0.9 | 40.9 | | | T20 | 65.6 | 66.9 | 1.3 | 66.9 | | |
| T5 | 20 | 21.2 | 1.2 | 21.2 | | | H7 | 40.9 | 43.3 | 2.4 | 43.3 | 4.0 | 9.7 | H11 | 66.9 | 71.9 | 5 | 71.9 | 2.5 | 12.7 |
| C3 | 21.2 | 22.8 | 1.6 | 22.8 | -11.2 | -17.9 | T13 | 43.3 | 44.3 | 1 | 44.3 | | | T21 | 71.9 | 73.3 | 1.4 | 73.3 | | |
| T6 | 22.8 | 24 | 1.2 | 24 | | | C7 | 44.3 | 45.5 | 1.2 | 45.5 | -12.2 | -14.6 | C11 | 73.3 | 75.3 | 2 | 75.3 | -10.2 | -20.3 |
| H4 | 24 | 26.6 | 2.6 | 26.6 | 3.5 | 9.2 | T14 | 45.5 | 46.5 | 1 | 46.5 | | | | | | | | | |
| T7 | 26.6 | 27.7 | 1.1 | 27.7 | | | H8 | 46.5 | 49.1 | 2.6 | 49.1 | 3.5 | 9.2 | | | | | | | |
| C4 | 27.7 | 29.1 | 1.4 | 29.1 | -11.6 | -16.3 | T15 | 49.1 | 50.2 | 1.1 | 50.2 | | | | | | | | | |
| | | | | | | | C8 | 50.2 | 51.6 | 1.4 | 51.6 | -11.6 | -16.3 | | | | | | | |

C = Cooling Period; H = Heating Period; T = Transition Period

FIG. 14F-2

| Period | Start Time (min) | End Time (min) | Duration (min) | Time Elapsed (min) | Rate of Heat Transfer (BTU) | Total Heat Transfer (BTU) | Period | Start Time (min) | End Time (min) | Duration (min) | Time Elapsed (min) | Rate of Heat Transfer (BTU) | Total Heat Transfer (BTU) | Period | Start Time (min) | End Time (min) | Duration (min) | Time Elapsed (min) | Rate of Heat Transfer (BTU) | Total Heat Transfer (BTU) |
|---|---|---|---|---|---|---|---|---|---|---|---|---|---|---|---|---|---|---|---|---|
| H1 | 0 | 5 | 3 | 3 | 5.6 | 16.7 | T8 | 1.2 | 1.7 | 0.5 | 19.5 | | | T16 | 1 | 1.8 | 0.8 | 34.4 | | |
| T1 | 5 | 6 | 1 | 4 | | | H5 | 1.7 | 3.2 | 1.5 | 21 | 6.6 | 9.9 | H9 | 1.8 | 3.8 | 2 | 36.4 | 6.1 | 12.2 |
| C1 | 6 | 7 | 1 | 5 | -13.2 | -13.2 | T9 | 3.2 | 3.7 | 0.5 | 21.5 | | | T17 | 3.8 | 4.6 | 0.8 | 37.2 | | |
| T2 | 7 | 8 | 1 | 6 | | | C5 | 3.7 | 4.9 | 1.2 | 22.7 | -11.8 | -14.2 | C9 | 4.6 | 5.6 | 1 | 38.2 | -13.2 | -13.2 |
| H2 | 8 | 10 | 2 | 8 | 6.1 | 12.2 | T10 | 4.9 | 5.3 | 0.4 | 23.1 | | | T18 | 5.6 | 6.6 | 1 | 39.2 | | |
| T3 | 10 | 11 | 1 | 9 | | | H6 | 5.3 | 6.8 | 1.5 | 24.6 | 7.1 | 10.7 | H10 | 6.6 | 8.6 | 2 | 41.2 | 6.1 | 12.2 |
| C2 | 11 | 12 | 1 | 10 | -13.2 | -13.2 | T11 | 6.8 | 7.2 | 0.4 | 25 | | | T19 | 8.6 | 9.6 | 1 | 42.2 | | |
| T4 | 12 | 12.8 | 0.8 | 10.8 | | | C6 | 7.2 | 8.4 | 1.2 | 26.2 | -11.8 | -14.2 | C10 | 9.6 | 10.6 | 1 | 43.2 | -13.2 | -13.2 |
| H3 | 12.8 | 14.8 | 2 | 12.8 | 6.1 | 12.2 | T12 | 8.4 | 8.9 | 0.5 | 26.7 | | | T20 | 10.6 | 11.6 | 1 | 44.2 | | |
| T5 | 14.8 | 15.6 | 0.8 | 13.6 | | | H7 | 8.9 | 10.4 | 1.5 | 28.2 | 7.1 | 10.7 | H11 | 11.6 | 13.6 | 2 | 46.2 | 6.1 | 12.2 |
| C3 | 15.6 | 16.6 | 1 | 14.6 | -13.2 | -13.2 | T13 | 10.4 | 10.9 | 0.5 | 28.7 | | | T21 | 13.6 | 14.6 | 1 | 47.2 | | |
| T6 | 16.6 | 17.2 | 0.6 | 15.2 | | | C7 | 10.9 | 12.1 | 1.2 | 29.9 | -11.4 | -13.7 | C11 | 14.6 | 15.6 | 1 | 48.2 | -13.2 | -13.2 |
| H4 | 17.2 | 19.2 | 2 | 17.2 | 6.1 | 12.2 | T14 | 12.1 | 12.7 | 0.6 | 30.5 | | | T22 | 15.6 | 16.6 | 1 | 49.2 | | |
| T7 | 19.2 | 19.8 | 0.6 | 17.8 | | | H8 | 12.7 | 14.2 | 1.5 | 32 | 6.6 | 9.9 | H12 | 16.6 | 19.6 | 3 | 52.2 | 5.6 | 16.7 |
| C4 | 19.8 | 21 | 1.2 | 19 | -11.4 | -13.7 | T15 | 14.2 | 14.8 | 0.6 | 32.6 | | | | | | | | | |
| | | | | | | | C8 | 14.8 | 15.8 | 1 | 33.6 | -13.2 | -13.2 | | | | | | | |

C = Cooling Period; H = Heating Period; T = Transition Period

FIG. 14G-2

THERMAL CONTRAST THERAPY DEVICES, METHODS, AND SYSTEMS

RELATED APPLICATIONS

This application is a continuation application of U.S. application Ser. No. 14/682,295, filed Apr. 9, 2015, which claims priority to U.S. Provisional Application Ser. No. 62/028,952 filed Jul. 25, 2014, the complete disclosures of which are hereby incorporated by reference into this application.

BACKGROUND

The present disclosure relates to thermal contrast therapy devices, treatment methods for providing thermal contrast therapy, and systems for providing and managing thermal contrast therapy treatments.

Thermal contrast therapy comprises therapeutic treatments in which a sequence of alternating cooling periods and heating periods are provided to one or more areas of a patient's body. The alternating cooling periods and heating periods respectively deliver or remove heat from the treatment area. The treatment sequence may be continued for a specified period of time or a specified number of heating periods and/or cooling periods. For example, the sequence may continue for an amount of time effective to achieve a desired therapeutic result.

Without wishing to be constrained by theory, the inventors understand that thermal contrast therapy can cause cycles of vasodilation and vasoconstriction, thus creating a pumping action which improves blood circulation and quality. Applying heat to body tissue may cause vasodilation, or dilation or widening of blood vessels. When blood vessels dilate, the flow of blood through the vessels increases due to a decrease in vascular resistance. Therefore, dilation of arterial blood vessels (mainly the arterioles) is believed to decrease blood pressure in the dilated vessels. Applying cold to body tissue may cause vasoconstriction, or contraction or narrowing of blood vessels, which is believed to increase blood pressure in the contacted blood vessels. When blood vessels constrict, the flow of blood is restricted or decreased, forcing blood to move to other parts of the body.

Blood delivers oxygen and nutrients to, and removes wastes from, tissues and organs. If circulation is poor or slow, delivery of healing nutrients or removal of toxins may be inadequate or suboptimum, which may delay healing or even cause degeneration of tissues or organs. It is believed that by improving the circulation and quality of blood, more nutrients are made available for cells to use, and that as such, toxins may be managed more efficiently.

Additionally, lymph vessels contract when exposed to cold and relax in response to heat. The lymph system, unlike the circulatory system, lacks a central pump. Without wishing to be constrained by theory, it is believed that alternating periods of heating and cooling cause lymph vessels to dilate and contract to essentially "pump" and move fluid from one area to another. This movement of fluid positively affects the inflammation process, which is the body's primary mechanism for healing damaged tissue.

Given these and other physiological effects known in the art, thermal contrast therapy may be an effective treatment for a number of different conditions. The therapy may be applied to any part of the body, for example, a part of the body that is inflamed, congested, injured, fatigued, or recovering from a surgical procedure. General therapeutic uses of thermal contrast therapy include management of pain, swelling, fever, toxins, spasms, constipation, and immune function. Thermal contrast therapy may be used generally to reduce edema or swelling, reduce or sooth pain, encourage healing of bones and tissue, and rehabilitate injuries to bone, muscle, ligaments, tendons, and skin. Thermal contrast therapy may also be an effective treatment for patients with hypothermia or frostbite, for example, to enhance circulation in affected tissue.

Thermal contrast therapy may also be used after an acute injury or surgery to reduce pain and swelling, and to promote healing. Athletes have also used thermal contrast therapy after or between competitions or training sessions, to speed recovery or reduce delayed onset muscle soreness by helping to flush lactic acid from sore muscles. Thermal contrast therapy may also be used to relax joint tissue such as ligaments and tendons, which may help increase range of motion. Thermal contrast therapy may also be an effective treatment for patients with spinal cord or nerve damage, for example, to enhance blood flow to the injured nerve tissue, or prevent or mitigate disputation of the tenuous blood supply.

Thermal contrast therapy may also be an effective therapy for diabetes and related physiological complications, for example, gangrene, or for lymphedema or other disorders associated with vascular or lymphatic insufficiency, for example, chronic venous insufficiency, venous stasis ulcers, post-mastectomy edema or chronic lymphedema, and for peripheral vascular disease or any other circulatory deficiency syndrome, for example, arteriosclerosis, deep vein thrombosis, Buereger's disease, or thromboangiitis obliterans. Thermal contrast therapy may provide therapeutic relief for multiple sclerosis and other autoimmune disorders, for example to treat pain and/or improve blood circulation. Other studies indicate that thermal contrast therapy may positively influence the immune system. Thermal contrast therapy may also be an effective therapy for destruction of subcutaneous lipid cells.

Thermal contrast therapy may be performed manually, such as by alternately immersing an area of the body (e.g., a foot, ankle, or leg) in a cold water whirlpool or bath and a warm whirlpool or bath, or by alternately applying a heat source, such as a heating pad or hydrocollator pack, and a cold source, such as an ice pack, or the like. Alternatively, thermal contrast therapy devices are commercially available which circulate water or other fluid through a treatment pad surrounding an area of the body sought to be treated. Such manual treatments and existing devices, however, may be unsuitable or ineffective for treating some conditions and/or patients.

Without wishing to be constrained by theory, it is believed that the effectiveness of thermal contrast therapy may be enhanced by providing a customized treatment sequence. Existing devices and treatment methods may offer only a finite number of pre-programmed therapies, with only limited ability to vary parameters of the treatment sequence. There is therefore a need for improved devices and methods for providing customized thermal contrast therapy treatment sequences. Some customized treatment sequences disclosed herein require a level of accuracy, precision, and control—for example, of the fluid temperature, the specified measure of heat transfer, and/or various other parameters of the treatment sequence—which may not be feasible with existing devices or manual treatments. There is therefore a further need for improved thermal contrast therapy devices having one or more of the various aspects disclosed herein.

Additionally, without wishing to be constrained by theory, it is believed that in some instances, the effectiveness of thermal contrast therapy may be enhanced by providing treatment sequences that include rapidly alternating cooling periods and heating periods and/or rapid transitions between such periods. Such treatment sequences may, among other things, be effective to enhance vasoconstriction and/or vasodilation and corresponding therapeutic effects. Existing devices may be unsuitable for providing such rapidly alternating periods and/or rapid transitions between periods. For example, existing devices may have an unsuitably large thermal mass in fluid communication with the fluid.

Various components of a thermal contrast therapy device each have a given thermal mass, which may be expressed as:

$$C_{th} = mc_p \tag{1}$$

where m is the mass of the component and $c_p$ is the isobaric specific heat capacity of the component averaged over the temperature range in question. The cumulative thermal mass attributable to the various components in thermal communication with fluid circulating through a thermal contrast therapy device may be expressed as:

$$C_{th\_total} = \Sigma_{n=1}^{n} C_{th_1} + C_{th_2} + \ldots + C_{th_n} \tag{2}$$

Such components in thermal communication with circulating fluid may absorb thermal energy from hot fluid (e.g., during heating periods) and dissipate thermal energy to cold fluid (e.g., during cooling periods).

When transitioning between periods of a treatment sequence, the duration of time required for the circulating fluid and the various components in thermal communication with the fluid to attain equilibrium temperature depends on, among other things, the thermal mass attributable to such components. When a thermal contrast therapy device has a relatively large thermal mass in thermal communication with the fluid circulating through the device, the duration of time required for the fluid to attain equilibrium temperature may be unsuitably large due to heat transfer with the thermal mass. For example, upon transitioning from a heating period to a cooling period, such thermal mass may accumulate heat from the hot fluid, which heat will then transfer to the cold fluid during the cooling period. Thus, when transitioning between periods some duration of time elapses before the fluid in thermal communication with the thermal mass attains equilibrium temperature with respect to heat transfer with such thermal mass. With some devices, the duration of time required to attain equilibrium temperature may exceed the duration of time specified for effecting transitions between alternating periods of a treatment sequence and/or the duration of time specified for such alternating periods, such as with rapidly alternating cooling periods and heating periods and/or rapid transitions between such periods. Consequently, the temperature of fluid circulating through a device may drift over the course of a given period or sequence of alternating periods due to heat transfer with such thermal mass. Also, the heating and/or cooling requirements for providing fluid to a treatment pad at a given temperature increase with increasing thermal mass in thermal communication with the fluid circulating through the treatment pad. Accordingly, devices having a relatively large thermal mass attributable to components in thermal communication with fluid circulating through a treatment pad may be unsuitable for performing certain treatment sequences disclosed herein. There is therefore an even further need for improved thermal contrast therapy devices.

Because of these and other limitations, it is believed that existing thermal contrast therapy devices and/or treatment methods may frequently provide a suboptimum treatment. Moreover, in some situations, a treatment provider or a user may administer treatments which could actually be harmful to the body. For example, if too much heating or cooling is provided, blood flow may be detrimentally restricted and/or tissue may be damaged. Such blood flow restriction may arise from blood pooling caused by excessive heating, or from constriction of blood vessels caused by excessive cooling. Thermal contrast therapy may be optimized, and injury may be avoided, by providing customized treatment sequences. Thus, it would be advantageous to provide thermal contrast therapy devices, methods, and systems as disclosed herein, which provide greater ability to vary and control treatment parameters, enhanced treatment precision and accuracy, and the ability to administer customized treatment sequences.

The skilled artisan will appreciate that research into the effects and benefits of thermal contrast therapy under various treatment conditions is relatively underdeveloped, and in many instances practitioners may desire further research as to the best way to treat a particular patient, body part, injury, ailment, or condition. It would therefore be advantageous to provide researchers and practitioners with devices, methods and systems that facilitate further research on the subject of thermal contrast therapy.

It is to be understood that thermal contrast therapy may be provided to any human or other mammalian patient, and as such, the present disclosure has applicability in both the medical and veterinary arts. The reader will appreciate that references in the present disclosure to a person, patient, user, and/or recipient of thermal contrast therapy treatments also means and refers to any other mammalian species.

SUMMARY

A summary of certain embodiments disclosed herein is set forth below. It should be understood that these aspects are presented merely to provide the reader with a brief summary of these certain embodiments and that they are not intended to limit the scope of the present disclosure.

The present disclosure relates to thermal contrast therapy devices, treatment methods for providing thermal contrast therapy, and systems for providing and managing thermal contrast therapy treatments. It should be understood that the thermal contrast therapy devices, methods, and systems disclosed herein may be implemented alone, together, or in combination with one another or with other devices, methods, or systems known in the art.

A thermal contrast therapy device may include one or more features disclosed herein. Such features may be effective to increase the thermodynamic efficiency of the device. A thermal contrast therapy device may be configured with features effective to reduce the thermal mass attributable to components in thermal communication with fluid circulating through the treatment pad, e.g., to minimize the thermal mass needing to be overcome before attaining equilibrium temperature when transitioning between heating periods and cooling periods. In some embodiments, a thermal contrast therapy device may be configured to provide rapidly alternating cooling periods and heating periods, and/or to rapidly transition between alternating cooling periods and heating periods. Such transitions may be effected at least as quickly as the duration of time determined by dividing the volume of fluid in a treatment pad by the flow rate of the fluid.

In some embodiments, a thermal contrast therapy device may include a cooling system having a first pump configured to circulate cold fluid and a heating system having a second pump configured to circulate hot fluid, in a sequence of alternating cooling periods and heating periods. Upon a transition between a first period and a second period, fluid having a first temperature corresponding to the first period displaces fluid having a second temperature corresponding to the second period. The cooling system may include a cold fluid recirculation line and/or the heating system may include a hot fluid recirculation line. The cooling system and the heating system may converge at an outflow fluid line, the outflow fluid line configured to discharge fluid from the device. In some embodiments, a thermal contrast therapy device may be configured to route circulating fluid either to the heating system and/or the cooling system based, at least in part, on the temperature of the fluid.

The use of a first pump configured to circulate cold fluid and a second pump configured to circulate hot fluid may be effective to reduce the thermal mass needing to be overcome before attaining equilibrium temperature when transitioning between alternating heating periods and cooling period, thereby increasing the thermodynamic efficiency of the cooling system and/or the heating system. Fluid flowing through an outflow fluid line may therefore attain equilibrium temperature rapidly. In some embodiments, a thermal contrast therapy device and/or the cooling system and/or the heating system thereof may be configured such that only a nominal change in temperature of the fluid occurs (if any), when flowing from the cooling block to the discharge of the device. In some embodiments, a thermal contrast therapy device and/or the cooling system and/or the heating system thereof may be configured such that there exists only a nominal cumulative thermal mass attributable to components in thermal communication with the fluid between a first point at which fluid discharges from the cooling system and a second point at which fluid discharges from the device.

In some embodiments, a thermal contrast therapy device may include a shared reservoir configured to supply fluid to the cooling system and the heating system. The shared reservoir may be in fluid communication with the cooling system and the heating system, and displaced fluid from the heating system and/or cooling system may be exchanged with fluid in the shared reservoir. The shared reservoir may hold a first volume of fluid from the cooling system and a second volume of fluid from the heating system. The shared reservoir may be configured such that the first volume of fluid increases upon a transition from a cooling period to a heating period, and the second volume of fluid increases upon a transition from a heating period to a cooling period. The volume of fluid in the shared reservoir may remain substantially constant during the sequence of alternating cooling periods and heating periods. In some embodiments, the shared reservoir allows stratification of hot fluid and cold fluid, and the heating system may preferentially draw stratified hot fluid from the shared reservoir and/or the cooling system may preferentially draw stratified cold fluid from the shared reservoir. Fluid communication between the shared reservoir and the heating system may occur through a first opening in the shared reservoir and fluid communication between the shared reservoir and the cooling system may occur through a second opening in the shared reservoir, with the first opening located at an elevation above the elevation of the second opening.

The cooling system may include a cooling block configured to hold a first volume of fluid, and the heating system may include a heating block configured to hold a second volume of fluid. The cooling block and/or the heating block may have a plurality of baffles defining a serpentine path for fluid travel between an inlet and an outlet. The cooling block and/or heating block may also be provided without such baffles. The cooling system may be configured to circulate cold fluid through a treatment pad, and the heating system may be configured to circulate hot fluid through the treatment pad. Fluid returning from the treatment pad may be routed to either the cooling system or the heating system based, at least in part, on the temperature of the fluid. In some embodiments, fluid circulates through the cooling system during heating periods, and/or fluid circulates through the heating system during cooling periods, for example, to adjust or maintain the temperature of the circulating fluid.

A thermal contrast therapy device may be configured to effect a pressure pulse in the treatment pad. In some embodiments, the cooling system may have a first supply valve and a first return valve, and the heating system may have a second supply valve and a second return valve. The valves may be magnetic solenoid valves. The pressure pulse may be effected at least in part by alternating a valve between opened and closed positions. In some embodiments, a thermal contrast therapy device may be configured to synchronize the frequency of a pressure pulse with the heart rate of a patient receiving treatment. In some embodiments, a thermal contrast therapy device may be configured to provide a pressure pulse effective to induce cycles of vasodilation and vasoconstriction. In some embodiments, cycles of vasodilation and vasoconstriction may be induced by alternating heating periods and cooling periods, and without providing pressure pulses.

In some embodiments, a thermal contrast therapy device may be configured to function with a plurality of different treatment pads. A treatment pad may comprise a network of interconnected cells or capillaries or a serpentine conduit, or combinations thereof, with an inflow port configured to receive fluid via an inflow tube, and an outflow port configured to return fluid via an outflow tube. In some embodiments, a treatment pad having a serpentine conduit allows for more rapid transitions between alternating heating periods and cooling periods. A serpentine conduit may comprise a plurality of conduit patterns, including hairpin corners, a Fermat's spiral, a modified Fermat's spiral, and combinations thereof. In some embodiments, a treatment pad may be provided having a configuration effective to provide a substantially uniform rate of heat transfer across the effective surface area of the treatment pad. In some embodiments, a pad ID tag may be embedded within a treatment pad or within a fitting configured to be attached to a treatment pad. A cuff having any desired shape or configuration may be provided for securing a treatment pad to an area of a patient's body sought to be treated. In some embodiments, a quick-release extension cord may be provided for fluid and data communication between a thermal contrast therapy device and a treatment pad. In some embodiments, a pad ID reader, one or more temperature sensors, and/or other electronics may be embedded in a quick-release extension cord.

The thermal contrast therapy devices disclosed herein may be configured to provide customized thermal contrast therapy treatment sequences. For example, a device may be configured to receive an indication effective to identify a treatment pad operably connected to the device and to cause the device to perform a thermal contrast therapy treatment sequence that is calibrated for the particular treatment pad operably connected to device.

The thermal contrast therapy devices disclosed herein may be configured to automatically adjust one or more sequence parameters during a selected treatment sequence or between a series of treatments. In some embodiments, a thermal contrast therapy device may be configured to allow a user to select or input customized sequence parameters, which may include, among other things, a customized time duration, pressure pulse frequency of the fluid, cuff compression, temperature-change profile, fluid temperature, and/or flow rate. The customized sequence parameters may correspond to one or more of the periods within a sequence, one or more sequences within a series of treatment sequences, or a series of treatment sequences within an ongoing treatment program. In some embodiments, a thermal contrast therapy device may be configured to receive an indication from one or more temperature sensors and/or flow meters and to effect a desired measure of heat transfer between the fluid and the patient's tissue, for example, by automatically adjusting the temperature and/or flow rate of the fluid. In some embodiments, a thermal contrast therapy device may be configured to receive an indication of one or more physiological parameter values exhibited by a patient and to perform a customized thermal contrast therapy treatment sequence based, at least in part, on the one or more physiological parameter values.

In some embodiments, a thermal contrast therapy device may be configured to transmit data to or receive data from a thermal contrast therapy system. Such data may include, for example, physiological parameter values exhibited by a patient, for example, during treatment. In some embodiments, subsequent additional treatments may be provided based, at least in part, on data corresponding to previous treatments. In some embodiments, a thermal contrast therapy device may be configured to perform a treatment sequence derived, at least in part, from an input received from a thermal contrast therapy system. The treatment sequence may be prescribed by a treatment provider or selected by a user of the thermal contrast therapy device. A treatment sequence may be based on, for example, current or previously provided treatment sequences, physiological parameter values exhibited by a patient during a current or previous treatment, and/or therapeutic effects observed in a patient during a current or previous treatment.

The methods disclosed herein include computer-implemented methods of providing thermal contrast therapy. In some embodiments, computer-implemented methods of providing thermal contrast therapy include circulating fluid from a thermal contrast therapy device through a treatment pad, the treatment pad having been applied to a patient, while providing a sequence comprising a plurality of alternating cooling periods and heating periods. Any one or more variables in the thermal contrast therapy sequence may be modified in order to provide a customized thermal contrast therapy treatment sequence. As examples, a customized treatment sequence may include automatically changing the fluid temperature and/or flow rate, the duration of one or more periods, the number of periods, and/or prescribing a sequence for one or more future thermal contrast therapy treatments.

A customized thermal contrast therapy treatment sequence may be prescribed by a treatment provider or selected by a user of a thermal contrast therapy device. The program may be selected, for example, from a database associated with a thermal contrast therapy system configured to provide customized thermal contrast therapy treatments. Customized sequence parameters may be based, for example, on a physiological parameter value exhibited by the patient, an area of the body sought to be treated, a particular symptom or condition sought to be treated, and/or a particular desired therapeutic result. In some embodiments, a customized treatment sequence may include effecting a desired measure of heat transfer between the fluid and the patient's tissue during one or more of the cooling periods and heating periods. The desired measure of heat transfer may be effected by automatically adjusting the flow rate of the fluid and/or the temperature of the fluid.

In some embodiments, a thermal contrast therapy treatment sequence may include rapidly alternating cooling periods and heating periods and/or rapid transitions between such periods. Such a sequence may be effective to induce cycles of vasoconstriction and vasodilation, which, in turn, may be effective to cause an increase in blood circulation and/or blood oxygen content in a patient's tissue.

In some embodiments, a thermal contrast therapy treatment sequence may be automatically adjusted to optimize one or more physiological parameters. For example, a treatment sequences may be automatically adjusted so as to optimize the magnitude of an increase in blood circulation and/or blood oxygen content induced by cycles of vasoconstriction and vasodilation. In some embodiments, a treatment sequence may be automatically adjusted when the patient exhibits a physiological parameter value that corresponds to a predefined value. In some embodiments, automatic adjustments to a thermal contrast therapy treatment sequence may include: changing a setting for the fluid temperature and/or flow rate; changing the duration of one or more of the cooling periods, heating periods, and/or transition periods; changing the number of cooling periods, heating periods, and/or transition periods; changing the frequency of the pressure pulse of the fluid; changing the compression of the treatment pad; changing the rate of change of the temperature and/or flow rate of the fluid; and/or prescribing a sequence for one or more future thermal contrast therapy treatments.

The thermal contrast therapy systems disclosed herein include systems comprising a thermal contrast therapy network, and one or more thermal contrast therapy devices configured to transmit data to and receive data from the thermal contrast therapy network. The thermal contrast therapy devices may be associated with one or more users, and the system may be configured to provide customized thermal contrast therapy to the users. In some embodiments, customized thermal contrast therapy treatment programs may be automatically generated based on data housed in a database associated with a thermal contrast system.

In accordance with the present disclosure, one or more computer-readable media bearing computer-readable instructions may be provided, that, when executed by a processor such as in an automated thermal contrast therapy device, cause the device to perform one or more of the computer-implemented methods of providing thermal contrast therapy. In addition to the foregoing, various other systems, devices, and methods, and non-transitory computer-readable media are set forth and described in the present disclosure.

The foregoing summary may contain simplifications, generalizations, inclusions, and/or omissions of detail; and consequently, those skilled in the art will appreciate that the summary is illustrative only and is not intended to be in any way limiting. In addition to the illustrative aspects, embodiments, and features described above, further aspects, embodiments, and features will become apparent by reference to the drawings, the following detailed description of illustrative embodiments, and the claims.

DESCRIPTION OF THE DRAWINGS

FIGS. 14A-1 and 14A-2; 14B-1 and 14B-2; 14C-1 and 14C-2; and 14D-1 and 14D-2 show exemplary customized thermal contrast therapy treatment sequences configured to provide a desired fluid temperature during the various periods of the sequence.

FIGS. 14E-1 and 14E-2; 14F-1 and 14F-2; and 14G-1 and 14G-2 show exemplary customized thermal contrast therapy treatment sequences configured to provide a desired measure of heat transfer during the various periods of the sequence.

DETAILED DESCRIPTION OF ILLUSTRATIVE EMBODIMENTS

In the following detailed description of illustrative embodiments, thermal contrast therapy devices, treatment methods for providing thermal contrast therapy, and systems for providing and managing thermal contrast therapy treatments will be described in greater detail, with reference to several embodiments thereof as disclosed herein and illustrated in the accompanying figures. Further exemplary thermal contrast therapy devices, methods and systems are described in U.S. patent application Ser. No. 14/340,904, the complete disclosure of which is hereby incorporated by reference into this application. In the following detailed description of illustrative embodiments, numerous specific details are set forth in order to provide a thorough understanding of the disclosed systems, devices, and methods. It will be apparent, however, to one skilled in the art, that the presently disclosed devices, methods, and systems each may be practiced without some or all of these specific details. In other instances, well known process steps and/or structures have not been described in detail in order to not unnecessarily obscure the present disclosure. The following detailed description of illustrative embodiments is therefore not to be taken in a limiting sense, and it is intended that other embodiments are within the scope of the presently disclosed devices, method, and systems. The features and advantages of the presently disclosed subject matter may be better understood with reference to the figures and discussions that follow. The claimed subject matter is defined by the appended claims and their equivalents.

I. Thermal Contrast Therapy Devices, Treatment Pads, and Quick Release Extension Cords Exemplary thermal contrast therapy devices, treatment pads, and quick release extension cords will now be discussed. The thermal contrast therapy devices disclosed herein are configured to provide a sequence of alternating cooling periods and heating periods to one or more areas of a patient's body to which a treatment pad may be applied. A thermal contrast therapy device may comprise a source of hot fluid, a source of cold fluid, and one or more pumps configured to circulate fluid through any one or more treatment pads in fluid communication with the device. In some embodiments, the thermal contrast therapy devices, treatment pads, and/or quick release extension cords disclosed herein may be configured with features effective to reduce the thermal mass attributable to components in thermal communication with fluid circulating through a device and/or a treatment pad.

Thermal Contrast Therapy Devices

Figure 1:
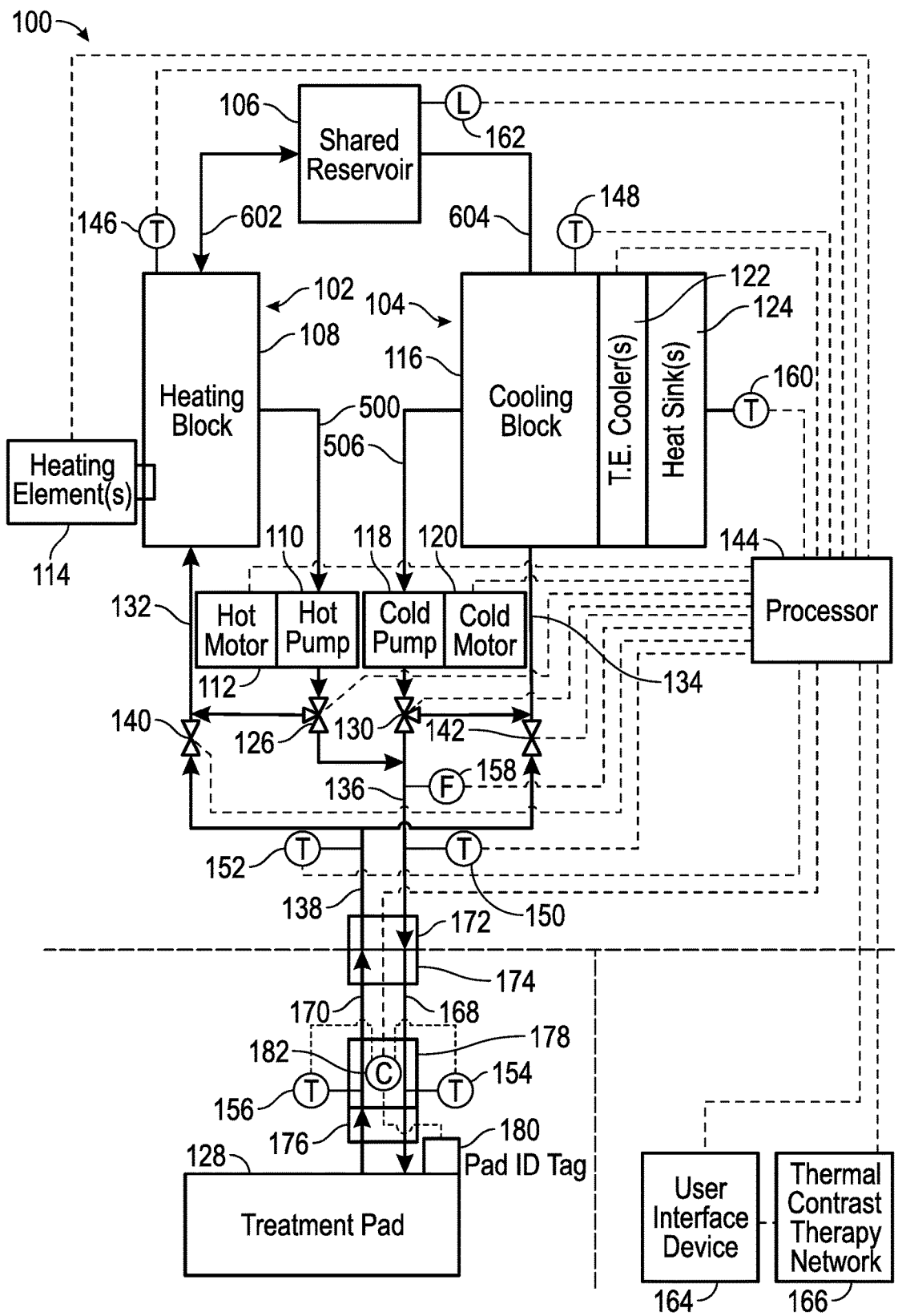
FIG. 1 shows a schematic of an exemplary thermal contrast therapy device.

Referring to FIG. 1, a schematic of an exemplary thermal contrast therapy device 100 is shown. Those skilled in the art will appreciate that numerous other embodiments of thermal contrast therapy devices are within the spirit and scope of the present disclosure.

The thermal contrast therapy device 100 shown in FIG. 1 comprises a heating system 102 configured to provide hot fluid, a cooling system 104 configured to provide cold fluid, and a shared reservoir 106 configured to hold a volume of fluid to supply both the heating system and the cooling system. A heating system may comprise a heating block 108, a hot pump 110 operably coupled to a hot motor 112, and one or more heating elements 114 that impart heat energy to the fluid. A cooling system may comprise a cooling block 116, and a cold pump 118 operably coupled to a cold motor 120. In some embodiments, the hot pump and the cold pump may be operably connected to a single motor. A cooling system may further comprise one or more cooling elements to draw heat energy from the fluid. The one or more cooling elements may be thermoelectric coolers 122 in thermal communication with the cooling block and one or more heat sinks 124. The shared reservoir 106 may be in fluid communication with the cooling system and the heating system, for example, via tubing or other means that permit fluid flow between the shared reservoir and each of the heating block and the cooling block. The shared reservoir may be positioned at an elevation such that fluid from the share reservoir gravity feeds both to the heating block and to the cooling block.

The heating system and cooling system are each configured to circulate fluid. The hot pump circulates fluid drawn from the heating block, and one or more hot supply valves 126 direct the fluid either back to the heating block and/or onward to one or more treatment pads 128. The cold pump circulates fluid drawn from the cooling block, and one or more cold supply valves 130 direct the fluid either back to the cooling block and/or onward to the one or more treatment pads. The hot supply valve 126 and the cold supply valve 130 may comprise three-way valves having one inlet and two outlets. When a first outlet of such a three-way valve is open, fluid flows to the heating block via recirculation line 132 or to the cooling block via cold recirculation line 134, respectively, and when a second outlet is open, fluid flows towards the one or more treatment pads via an outflow fluid line 136. Fluid circulated through the one or more treatment pads returns to the device via return fluid line 138, and may be directed either to the heating block via hot return valve 140 and/or to the cooling block via cold return valve 142. In some embodiments, fluid circulating through a treatment pad may be directed to either the heating block and/or the cooling block based on the temperature of the fluid, for example, so as to optimize the heating and cooling efficiency of the thermal contrast therapy device.

Fluid may be periodically or continuously circulated through the heating system and/or the cooling system so as to provide a volume of fluid having a desired temperature. Fluid from either the heating system and/or the cooling system may be circulated through the treatment pad during alternating heating periods and or cooling periods. For example, during heating periods, hot fluid may be circulated through the treatment pad, via the second outlet of the hot supply valve 126 and the hot return valve 140, while cold fluid circulates through the cooling system via the first outlet of the cold supply valve 130. Similarly, during cooling periods, cold fluid may be circulated through the treatment pad, via the second outlet of the cold supply valve 130 and the cold return valve 142, while hot fluid circulates through the heating system via the second outlet of the hot supply valve 126. In some embodiments, a portion of the fluid discharged from the hot pump 110 may be routed through the first outlet of the hot supply valve 126 to the heating block during heating periods, for example, to maintain circulation of fluid through the heating block or to augment the flow rate of the hot fluid circulated through the treatment pad. Similarly, a portion of the fluid discharged from cold pump 118 may be routed through the first outlet of the cold supply valve 130 to the cooling block during cooling periods, for example, to maintain circulation of fluid through the cooling block or to augment the flow rate of the cold fluid circulated through the treatment pad. In some embodiments, a portion of the fluid that circulates through the treatment pad during a heating period may be routed to the cooling block, via the cold return valve 142, for example, to adjust the temperature of the fluid in the cooling block. Similarly, a portion of the fluid that circulates through the treatment pad during a cooling period may be routed to the heating block, via the hot return valve 140, for example, to adjust the temperature of the fluid in the heating block.

The thermal contrast therapy devices disclosed herein may be configured to rapidly and efficiently transition between alternating cooling periods and heating periods. Upon transitioning between a first period and a second period, fluid having a first temperature corresponding to the first period displaces fluid having a second temperature corresponding to the second period. For example, upon initiating a transition from a heating period to a cooling period, hot fluid will have been circulating through the treatment pad and to the heating block, thus providing fluid having a temperature corresponding to the temperature specified for the heating period. At the transition from the heating period to the cooling period, fluid having a temperature corresponding to the temperature specified for the cooling period displaces the fluid from the heating period. The displaced fluid flows either to the heating block via the hot return valve 140 and/or to the cooling block via the cold return valve 142. In some embodiments, displaced fluid from the heating period flows through the hot return valve 140 until about such time as a substantial portion of the fluid from the heating period has been displaced and, for example, returned to the heating system, at which point the hot return valve 140 closes and fluid then flows through the cold return valve 142 to the cooling system. At the transition from a cooling period to a heating period, fluid having a temperature corresponding to the temperature specified for a heating period similarly displaces the fluid from the cooling period.

In some embodiments, a thermal contrast therapy device may be configured to minimize the thermal mass needing to be overcome before attaining equilibrium fluid temperature when transitioning between alternating heating periods and cooling periods. This may be accomplished, for example, by minimizing the thermal mass attributable to components in thermal communication with fluid from the heating block and with fluid from the cooling block, e.g., during alternating heating periods and cooling periods. For example, as shown in FIG. 1, a heating system 102 and a cooling system 104 are provided having separate, dedicated pumps, valves, and recirculation lines. As shown in FIG. 1, the heating system 102 and the cooling system 104 converge at and outflow fluid line 136, and fluid circulating through the treatment pad returns either to the heating system and/or the cooling system via return fluid line 138. As such, when circulating fluid through the treatment pad 128, fluid pumped to the treatment pad from the heating block 108 and fluid pumped to the treatment pad from the cooling block 116 commonly interact only with the thermal mass of components beginning from the outflow fluid line 136 and ending with the return fluid line 138. Given this, when transitioning between periods of a treatment sequence, only a nominal period of time elapses before the fluid circulating through the treatment pad, and the various components in thermal communication with such fluid, attain equilibrium temperature with respect to the thermal mass of such components. Thus, thermal contrast therapy devices may be configured to provide treatment sequences having rapidly alternating periods and/or rapid transitions between periods.

In some embodiments, thermal contrast therapy devices may exhibit enhanced thermodynamic efficiency, such as with respect to the cooling system and/or the heating system. As an example, heating and cooling loads of are reduced by minimizing the thermal mass attributable to components in thermal communication with fluid from the heating block and with fluid from the cooling block, and as such, the energy required to provide fluid to a treatment pad at a given temperature may be reduced. By contrast, when a pump, recirculation line, and/or valve are commonly used to supply the treatment pad with fluid from the heating block and with fluid from the cooling block, a larger thermal mass will be in thermal communication with the fluid circulating through the treatment pad. As such, when transitioning between periods of a treatment sequence, a longer duration of time will elapse at a given fluid temperature and flow rate before fluid circulating through a treatment pad attains equilibrium temperature with respect to such thermal mass in thermal communication with the fluid.

In some embodiments, a thermal contrast therapy device may be configured such that upon transitioning from a heating period to a cooling period or from a cooling period to a heating period, the fluid flowing towards one or more treatment pads via outflow fluid line 136 attains equilibrium temperature, with respect to such thermal mass in thermal communication with the fluid, within less than about 120 seconds to less than about 5 seconds, for example, within less than 120 seconds, less than 110 seconds, less than 100 seconds, less than 90 seconds, less than 80 seconds, less than 70 seconds, less than 60 seconds, less than 50 seconds, less than 40 seconds, less than 30 seconds, less than 20 seconds, less than 10 seconds, or less than 5 seconds. Such equilibrium temperature may be considered attained when the temperature of the fluid falls within 1° F. of the equilibrium temperature of the fluid with respect to such thermal mass in thermal communication with the fluid.

In some embodiments, a thermal contrast therapy device may be provided having a heating system and/or a cooling system configured such that upon transitioning from a heating period to a cooling period or from a cooling period to a heating period, any change in temperature of the fluid attributable to thermal communication with the thermal mass from the heating block 108 or from the cooling block 116, as applicable, to the discharge of the thermal contrast therapy device (e.g., the discharge of outflow fluid line 136), may be less than about 5° F., less than about 4° F., less than about 3° F., less than about 2° F., less than about 1° F., less than about 0.5° F., or less than 0.1° F. In some embodiments, a thermal contrast therapy device may be configured such that any change in temperature of the fluid when flowing from the heating block 108 or from the cooling block 116 to the treatment pad 128 may be less than about 5° F., less than about 4° F., less than about 3° F., less than about 2° F., less than about 1° F., less than about 0.5° F., or less than 0.1° F. Such changes in temperature may be determined by measuring the temperature of the fluid when flowing from the heating block or cooling block, as applicable, and the temperature of the fluid when flowing out of the device or into the treatment pad, as applicable, and calculating the difference between those temperatures.

In some embodiments, a thermal contrast therapy device may be equipped with a heating system and/or a cooling system configured such that the cumulative thermal mass, $C_{th\_tota}$, attributable to the various components in thermal communication with the fluid, from between the discharge of the heating system 102 and/or the cooling system 104 (e.g., the convergence thereof at the outflow fluid line 136) to the discharge of the thermal contrast therapy device (e.g., the discharge of outflow fluid line 136), may be less than about 0.5 BTU/° F., less than about 0.4 BTU/° F., less than about 0.3 BTU/° F., less than about 0.2 BTU/° F., less than about 0.1 BTU/° F., less than about 0.05 BTU/° F., or less than about 0.01 BTU/° F.

Further referring to FIG. 1, when performing a thermal contrast therapy treatment sequence, fluid may be supplied to a treatment pad during a given period either by the hot pump 110, by the cold pump 118, or in part by the hot pump and in part by the cold pump. For example, in some embodiments, fluid corresponding to a heating period may include fluid supplied by the hot pump, and fluid corresponding to a cooling period may include fluid supplied by the cold pump. In some embodiments, fluid from the heating block may be tempered with fluid from the cooling block, for example, to provide fluid to the treatment pad during a heating period having a temperature that is less than the temperature of the fluid discharged from the hot pump. Similarly, fluid from the cooling block may be tempered with fluid from the heating block, for example, to provide fluid to the treatment pad during a cooling period having a temperature that is greater than the temperature of the fluid discharged from the cold pump. By such tempering, a multitude of intermediate fluid temperatures may be provided through mixing various proportions of hot and cold fluid, and without first having to heat or cool a volume of fluid to the desired intermediate temperature. In some embodiments, when fluid from the hot pump and cold pump are mixed with one another, fluid returning from the treatment pad may be routed in part to the heating block and in part to the cooling block. In some embodiments, all of the fluid returning from the treatment pad may be routed to either the heating block or the cooling block. The routing of fluid returning from the treatment pad as between the heating block and the cooling block may be determined based on the resulting loads of the heating system and/or cooling system, and the corresponding energy efficiency of the device.

When transitioning between a first period and a second period, displaced fluid from the first period causes a corresponding volume of fluid to be exchanged with fluid from the shared reservoir 106. For example, when fluid from the cooling block displaces fluid from a heating period with fluid for a cooling period, the displaced fluid may flow to the heating block, which causes a corresponding volume of fluid to flow from the heating block to the shared reservoir, and from the shared reservoir to the cooling block. Over a sequence of alternating cooling periods and heating periods, fluid flows between the heating block, the shared reservoir, and the cooling block, in alternating directions. The shared reservoir allows the volume of fluid in the heating system and the cooling system to balance, for example, when displacing fluid during transitions between periods, when fluid from the hot pump and cold pump are mixed with one another in various proportions, and/or when fluid returning from the treatment pad is routed in part to the heating block and in part to the cooling block in various proportions. While fluid flows in and out of the shared reservoir in alternating directions, the volume of fluid in the shared reservoir remains substantially constant, as fluid gravity feeds to the heating block and the cooling block in the opposite direction of fluid flowing into the shared reservoir, as discussed below with respect to FIGS. 6A and 6B.

In some embodiments, fluid communication between the shared reservoir and the heating block occurs through a first opening in the shared reservoir, and fluid communication between the shared reservoir and the cooling block occurs through a second opening in the shared reservoir. The first opening may be located at an elevation above the elevation of the second opening. Such configuration may be effective to allow stratification of hot fluid and cold fluid within the shared reservoir. Fluid in the cooling block may stratify, for example, when fluid exchange with the shared reservoir takes place with minimal agitation or turbulence such as under substantially laminar flow conditions. Stratification of hot fluid and cold fluid in the shared reservoir may reduce the heating and cooling demands of the heating block and the cooling block, respectively, as fluid flowing from the shared reservoir to the hot system may preferentially draw from the stratified hot fluid, while fluid flowing from the shared reservoir to the cold system may preferentially draw from the stratified cold fluid. Such stratification may be enhanced by minimizing the degree of turbulence in the shared reservoir caused by fluid flowing in and out of the shared reservoir. This may be achieved, for example, by configuring the shape and size of the shared reservoir and/or locations where the heating block and/or cooling block interface with the shared reservoir, so as to minimize turbulence. Such turbulence in the shared reservoir may be of particular concern, for example, when flow rates exceedingly depart from laminar flow conditions, and/or when providing pressure pulses. Such pressure pulses may create turbulence that disrupts stratification in the shared reservoir. One or more inline pulse dampeners may be used to mitigate such disruptions caused by pressure pulses. Baffles and/or diffusers may also be used to minimize turbulence in the shared reservoir. Configurations that provide laminar flow (as opposed to turbulent flow) may also enhance stratification in the shared reservoir.

In some embodiments, one or more baffles and/or plate diffuser elements may be provided in the shared reservoir to enhance stratification between hot fluid and cold fluid. For example, such an element may be positioned at about the expected line of stratification between hot fluid and cold fluid. In some embodiments, such an element may be configured to float or adjust in conjunction with the line of stratification within the shared reservoir.

Further referring to FIG. 1, a thermal contrast therapy device may be equipped with a processor 144 to control the operation of device. The processor may be configured to cause the thermal contrast therapy device to perform customized thermal contrast therapy treatment sequences, for example, by monitoring and/or controlling various aspects of the device, including the heating element(s), thermoelectric cooler(s), heat sink(s), pump(s), and valve(s). In some embodiments, a thermal contrast therapy device may be equipped with one or more temperature sensors and/or flow meters, from which the processor may be configured to receive an input which may be used to monitor and/or control operation of the device. For example, a heating block temperature sensor 146 may be provided to measure the temperature of the fluid at the heating block, and/or a cooling block temperature sensor 148 may be provided to measure the temperature of the fluid at the cooling block. Further temperature sensors may be provided; for example, a fluid supply line temperature sensor 150 may be provided (e.g., along the outflow fluid line 136), and/or a fluid return line temperature sensor 152 may be provided (e.g., along the return fluid line 138).

In some embodiments, the processor 144 may be configured to receive an input from temperature sensors that are external to the device, for example, a treatment pad inlet temperature sensor 154 and/or a treatment pad outlet temperature sensor 156, which temperature sensors may be proximately located at about a treatment pad's inlet and outlet, respectively. In some embodiments, a flow meter 158 may be provided, for example, to measure the flow rate of fluid circulating through the treatment pad. Further temperature sensors, flow meters, and other instrumentation may also be provided. The temperature of the heat sink may be monitored via heat sink temperature sensor 160, for example, to monitor and control cooling of fluid effected by the cooling system. In some embodiments, the shared reservoir may be equipped with a level sensor 162. Such level sensor may provide an indication as to whether the fluid level in the shared reservoir departs from an allowable operating range, which may occur in the event of fluid evaporation and/or in the event of a disruption in device operations such as a stoppage or decrease in fluid flow.

The processor 144 may be configured to control the temperature of the fluid, utilizing temperature measurements from any one or more temperature sensors. The processor may also be configured to control the flow rate of the fluid, utilizing flow measurements from any one or more flow meters. These temperature and/or flow rate measurements may be utilized in thermodynamic calculations to provide customized thermal contrast therapy treatment sequences. Such treatment sequences may include effecting a specified measure of heat transfer (i.e., a quantity of heat and/or a rate of heat transfer).

In some embodiments, a thermal contrast therapy device may be configured to interact with a user interface device 164, for example, to allow a user to control the operation of the thermal contrast therapy device, such as by selecting or inputting customized treatment sequence parameters. The user interface device may include any suitable interface, such as a touch screen, monitor, keypad, mouse, or other interface device or any combination thereof. The user interface device may be integrated with a thermal contrast therapy device, for example, a touch screen may be integrated with the device's casing 200 (FIG. 2), e.g., on the frontward face of the casing. Alternatively, a user interface device may be provided separately. For example a personal computer, tablet, mobile phone, or other hand-held device may be provided for interacting with a thermal contrast therapy device. In some embodiments, the processor may be configured to interact with a thermal contrast therapy network 166. The processor may be configured to perform a treatment sequence derived, at least in part, from an input received from a thermal contrast therapy network. The treatment sequence may be prescribed buy a treatment provider or selected by a user of the thermal contrast therapy device. The selected treatment may be chosen from a database of available treatment sequences supplied through the thermal contrast therapy network, or manually input, via a user interface. The processor may also be configured to automatically adjust one or more sequence parameters so as to perform a selected treatment sequence.

The thermal contrast therapy devices disclosed herein may be configured to function with a plurality of different treatment pads of various sizes and/or configurations. Treatment pads having different sizes may be provided (e.g., small, medium, large, extra-large, etc.), for example, to accommodate different sized patients. Treatment pads having different configurations may be provided, for example, to accommodate different body parts (e.g., for the arm, leg, knee, foot, ankle, hip, lumbar, back, shoulder, elbow, wrist, neck, or cranium, etc.). As shown in FIG. 1, fluid from the thermal contrast therapy device circulates through a treatment pad through supply line 168 and return line 170. Fluid lines may be coupled to the thermal contrast therapy device and treatment pad via any suitable means. In some embodiments, fluid lines may be coupled to the thermal contrast therapy device via a device interface fitting 172 configured to releasably mate with a corresponding device-side fitting 174 on the fluid lines. Similarly, fluid lines may be coupled to the treatment pad via a pad interface fitting 176 configured to releasably mate with a corresponding pad-side fitting 178 on the opposite end of the fluid lines. A treatment pad ID tag 180 may be embedded in the treatment pad or in a pad interface fitting 176. A treatment pad ID tag may be used, for example, to identify a treatment pad and associate thermal contrast therapy treatments and related data with the treatment pad in service. A pad ID reader 182 may be built into pad-side fitting 178, for example, to interact with treatment pad ID tag and/or temperature sensors 154, 156 embedded in the pad-side fitting or elsewhere, and to transmit data to the thermal contrast therapy device. The pad ID reader may, in turn, interact with a processor, for example, to relay inputs that may be used to monitor and control thermal contrast therapy treatments and/or record and store data associated with such treatments.

In some embodiments, a thermal contrast therapy device may be configured to automatically adjust one or more parameters of a treatment sequence based, at least in part, on one or more characteristics of a particular treatment pad. Such parameters include fluid temperature, flow rate, and/or duration of time for one or more periods of a treatment sequence. Such automatic adjustments may be configured to enable a thermal contrast therapy device to effect a desired treatment across a plurality of different treatment pads having varying dimensions and/or configurations. In some embodiments, a thermal contrast therapy device may be configured to effect a specified measure of heat transfer (i.e., a quantity of heat and/or a rate of heat transfer) by automatically adjusting one or more of: fluid temperature, flow rate, and/or duration of time, based, at least in part, on the identification a particular treatment pad operably connected to the device and/or one or more characteristics of such treatment pad.

In some embodiments, a thermal contrast therapy device may be configured to perform a treatment sequence based, at least in part, on the identification a particular treatment pad operably connected to the device and/or one or more characteristics of such treatment pad. For example, if the device identifies a treatment pad associated with knee treatments, the device may perform a treatment sequence intended for treating knees; or, if the device identifies a cuff associated with the lumbar region, the device may perform a treatment sequence intended for treating the lumbar region. Such treatment sequences may be provided based on virtually any treatment pad associated with virtually any area of the body or condition sought to be treated.

Figure 2:
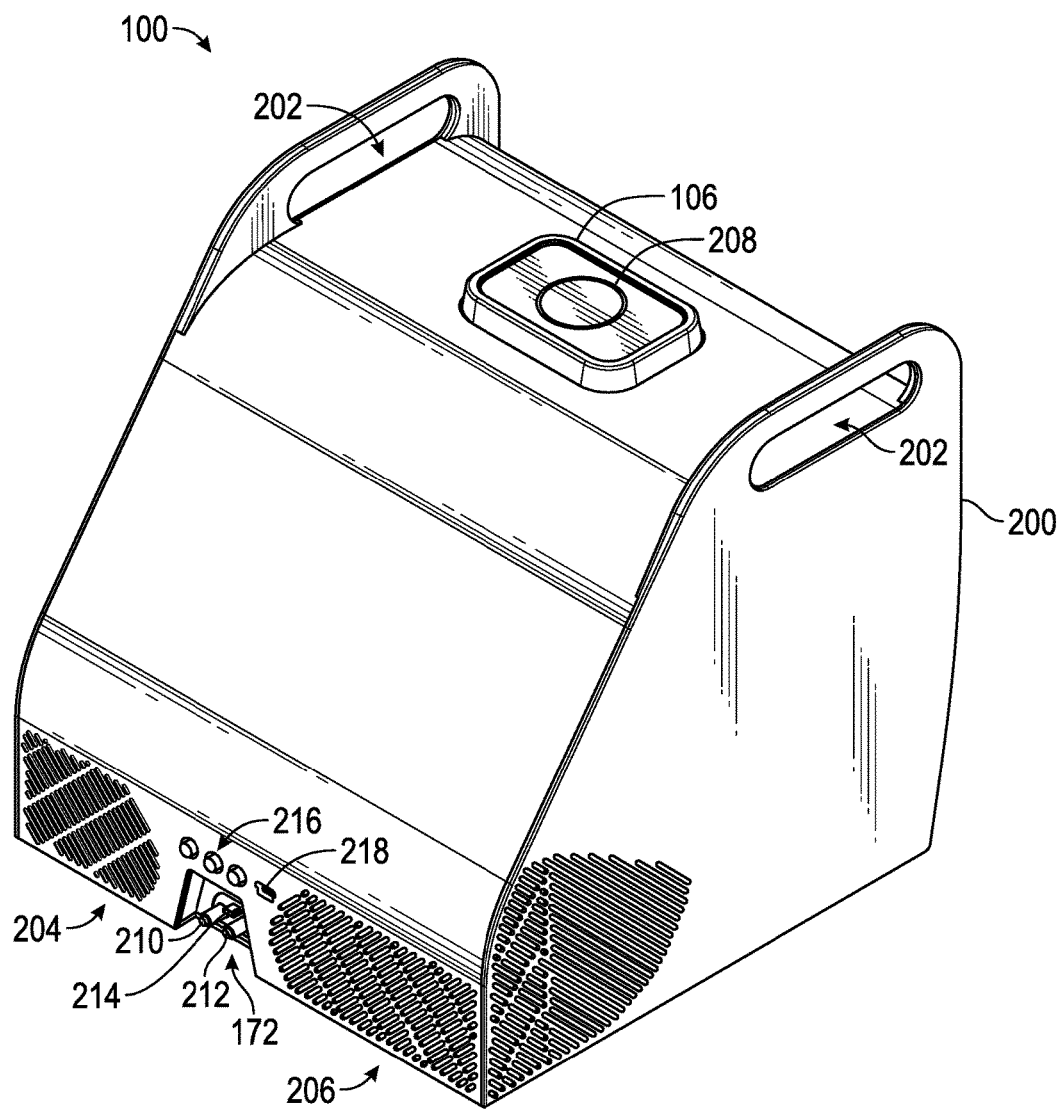
FIG. 2 shows a front perspective view of an exemplary thermal contrast therapy device.

An exemplary configuration of a thermal contrast therapy device will now be discussed. It is to be understood that various other configurations are within the spirit and scope of the present disclosure. Referring now to FIG. 2, a front perspective view of an exemplary thermal contrast therapy device 100 is shown. The various components of the device may be contained within a casing 200, which may be configured with handles 202 for portability. The casing may be fabricated from any suitable material or combinations thereof, including plastics such as acrylonitrile butadiene styrene, polyvinyl chloride, metals, composites, or other materials. Vents 204, 206 provide ventilation to various components within the device. The shared reservoir 106 may be accessed via a cap 208 for adding or removing fluid. The cap 208 may be configured with a pressure relief vent or valve, so as to equalize pressure that may accumulate within the thermal contrast therapy device. Such pressure may accumulate from vapor produced by heating fluid.

A device interface fitting 172 may be conveniently located, such as on the front of the casing as shown in FIG. 2. The device interface fitting may have a supply line fitting 210, a return line fitting 212, and a data fitting 214, and each of which may be configured to releasably mate with corresponding receptacles on a device-side fitting 174 (FIG. 1). The data fitting 214 may interface with a cable configured to transmit data between the thermal contrast therapy device and associated electronic components, such as a pad ID reader 182, temperature sensors 154, 156, a treatment pad ID tag 180, an auxiliary device, and/or other components (FIG. 1). Indicator lights 216 provide users with information about the status of the device. A data port 218 may be provided on the front of the device as a convenient location to transmit data to or from the device, for example, to upload or download data associated with a user of the device or thermal contrast therapy treatments, and/or to enable the device to interact with one or more auxiliary devices or other electronic components.

Figure 3:
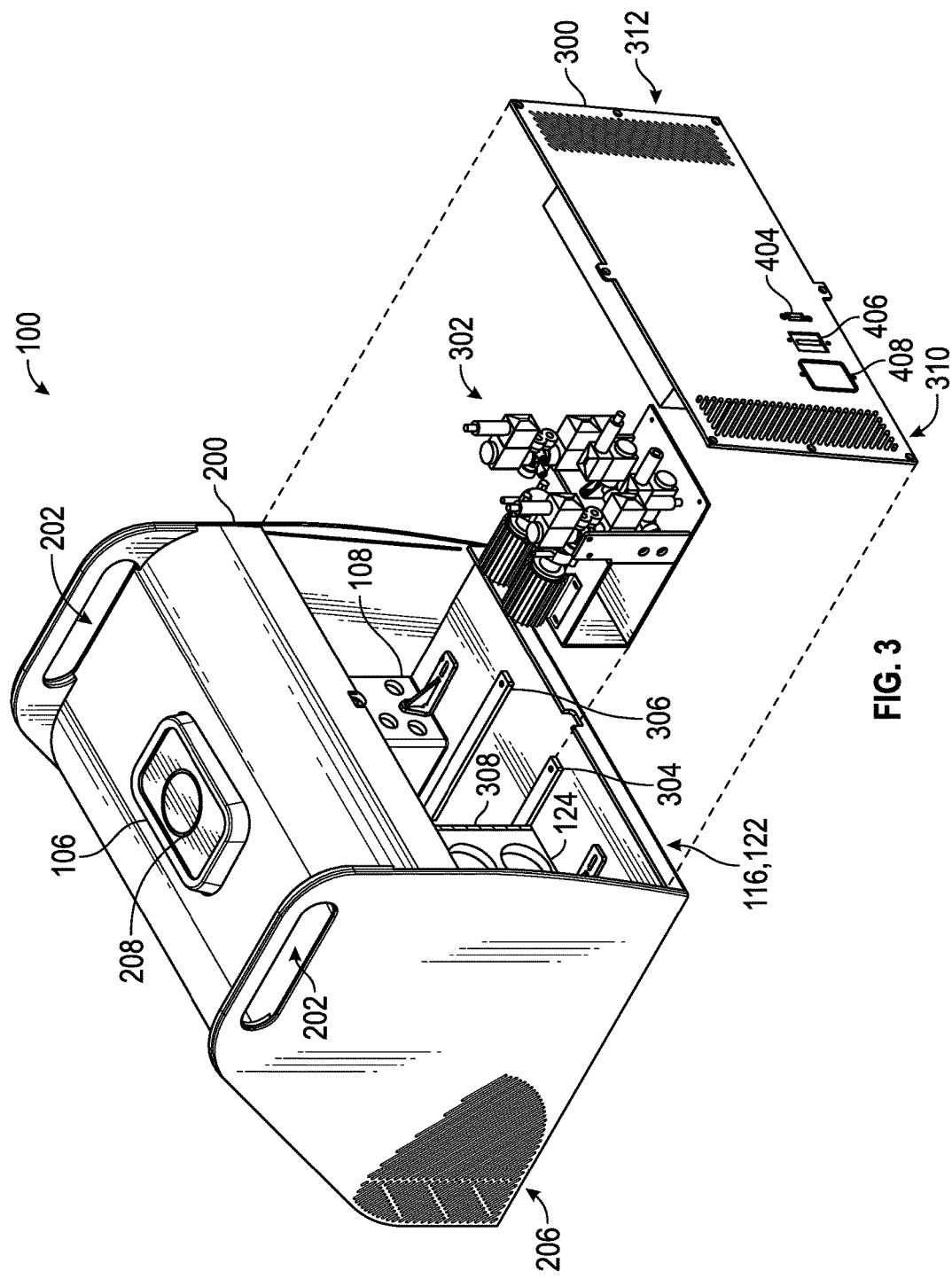
FIG. 3 shows a rear perspective, exploded view of the exemplary thermal contrast therapy device of FIG. 2.
Figure 4:
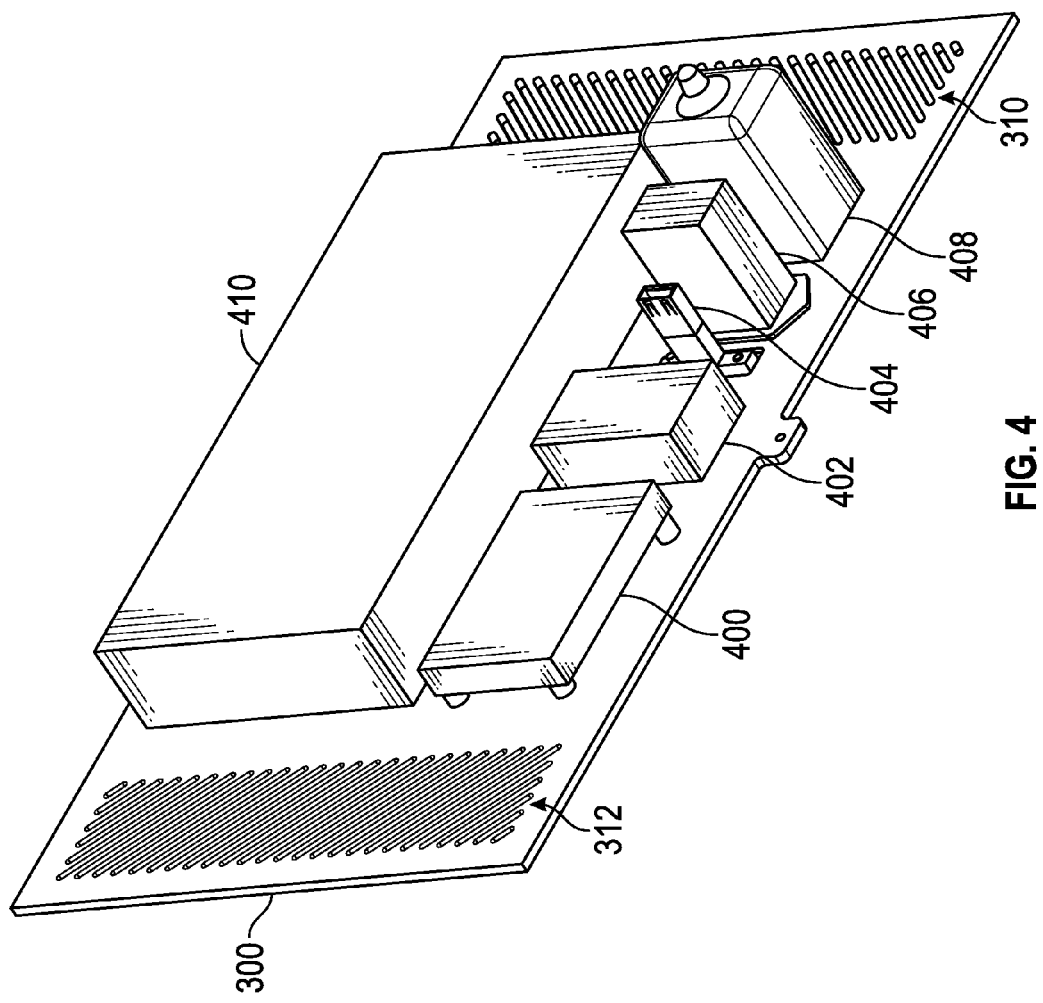
FIG. 4 shows a perspective view of the inside of the rear panel of the exemplary thermal contrast therapy device of FIG. 2.

Referring now to FIG. 3, a rear perspective, exploded view of the exemplary thermal contrast therapy device of FIG. 2 is shown. A removable rear panel 300 provides access to components within the thermal contrast therapy device. A pump and valve module 302 slides between brackets 304, 306 configured to secure the pump and valve module within the casing 200. The cooling block 116 and one or more thermoelectric cooler(s) 122 (both not shown) and heat sink(s) 124 reside adjacent to the pump and valve module, and the heating block 108 resides opposite thereof. A partition 308 provides structural integrity to the casing, and also insulates the cooling block, thermoelectric cooler(s), and heat sink(s) from other components within the casing. Vents 310, 312 provide ventilation to various components within the device. As shown in FIG. 4, various electronic components may be mounted to the inside of the removable rear panel 300, including a circuit board 400, having a processor 144, a USB hub 402, a USB port 404, a counter 406, a power input 408, and a power supply 410. Such electronic components are well known in the art, and the skilled artisan may select from among any suitable alternatives. Referring again to FIG. 3, the USB port 404, the counter 406, and the power input 408 are each accessible from the rear of the device.

The power supply 410 provides power to operate the thermal contrast therapy device, e.g., 12 volt DC power. In some embodiments, a modular configurable power supply may be used to power a thermal contrast therapy device. Pulse width modulation may be used to control the amount of power delivered to various components of the thermal contrast therapy device, such as pump motors, valves, heating elements, thermoelectric coolers, heat sinks, and other components. Exemplary modular configurable power supplies include UtiliMod power supplies such as the UX6 1200 W power supply, available from Excelsys Technologies, Rockwall, Tex.

Figure 5:
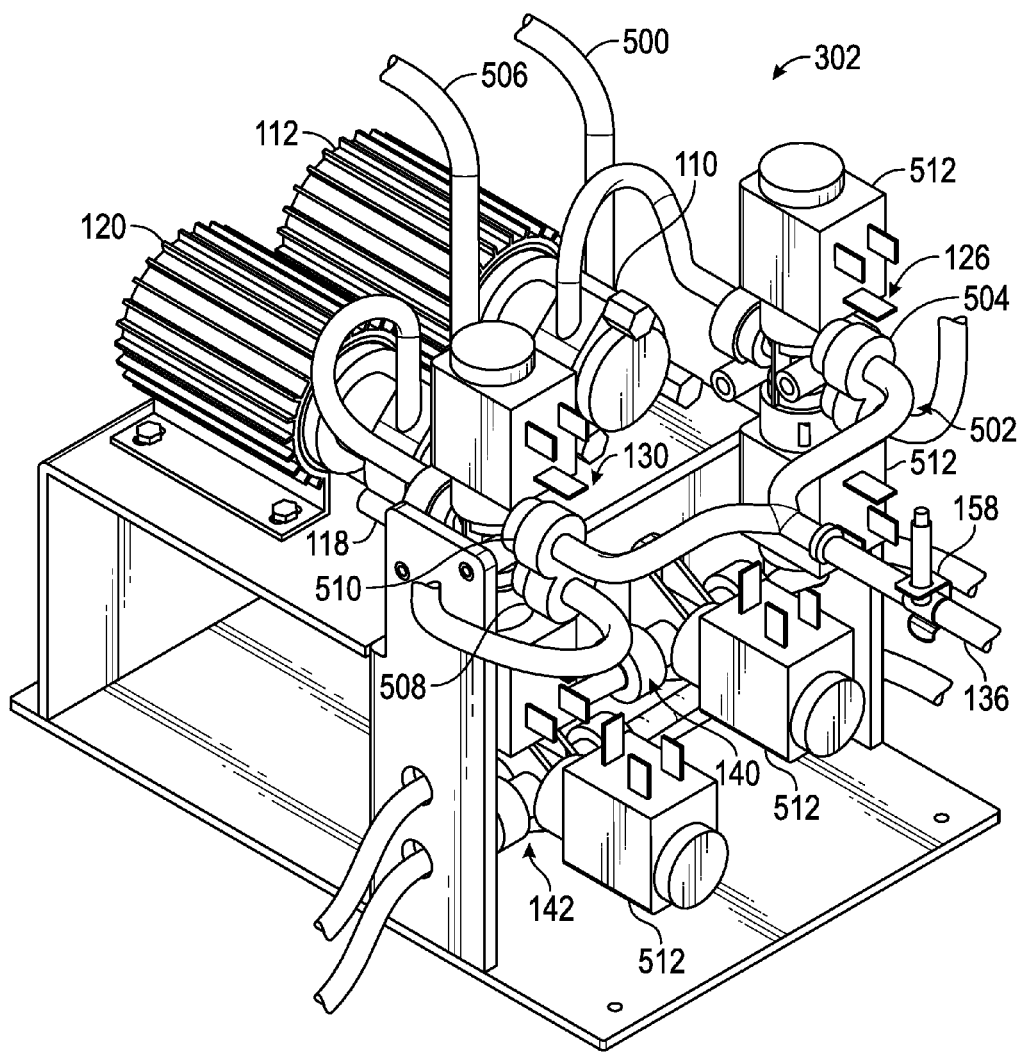
FIG. 5 shows a perspective view of the pump and valve module of the thermal contrast therapy device of FIG. 2.

Referring now to FIG. 5, a perspective view of the pump and valve module 302 is shown. The pump and valve module provides a conveniently removable platform for mounting pumps, motors, and valves. The pump and valve module may include mounting locations for any number of components. For example, as shown in FIG. 5, the pump and valve module may be configured to support the hot pump 110 operably coupled to a hot motor 112, and the cold pump 118 operably coupled to a cold motor 120. A thermal contrast therapy device may utilize any one or more pumps known in the art suitable to circulate fluid through the reservoirs and one or more treatment pads. Pumps are well known in the art, and any suitable pump may be used. As shown in FIG. 5, gear pumps may be used. For example, suitable gear pumps are available from TCS Micropumps Ltd., Faversham, England. In some embodiments, a diaphragm pump may be used. Suitable diaphragm pumps are available from KNF Neuberger Inc., Trenton N.J. When using a diaphragm pump, in some embodiments an unwanted pressure pulse may be created. Such pressure pulse may be dampened using an inline pulse dampener, which may be located, for example, before or after the supply valves (i.e., hot supply valve 126 and/or cold supply valves 130), e.g., along the outflow fluid line 136. In some embodiments, a small segment of expandable tubing may be effective as an inline pulse dampener. In some embodiments, when using a diaphragm pump, a desired pressure pulse in a treatment pad may be provided using one or more of the return valves (i.e., hot return valve 140 and/or cold return valve 142). Alternatively, one or more low pressure peristaltic pumps or "tube pumps" may be used. Suitable peristaltic pumps are available from Anko Products Inc., Bradenton, Fla., or from Watson Marlow, Wilmington, Mass. In some embodiments, the hot pump 110 and the cold pump 118 may be configured to each provide fluid at a flow rate of at least between about 10 to 100 mL per minute, for example, between 10 to 25 mL/min, 25 to 50 mL/min, 50 to 100 mL/min, 100 to 150 mL/min, 150 to 250 mL/min, 250 to 500 mL/min, or 500 to 1000 mL/min, or any intermediate flow rate, lesser flow rate, or greater flow rate.

The pump and valve module 302 may be further configured to support the hot supply valve 126, the cold supply valve 130, the hot return valve 140, and the cold return valve 142. The hot pump draws fluid from the heating block 108 (FIG. 1) through hot feed line 500. Fluid discharged from the hot pump may be routed through the hot supply valve's first outlet of 502 to the heating block 108, or through the hot supply valve's second outlet 504 to a treatment pad 128 (FIG. 1). The cold pump draws fluid from the cooling block 116 (FIG. 1) through cold feed line 506. Fluid discharged from the cold pump may be routed through the cold supply valve's first outlet of 508 to the cooling block 116, or through the cold supply valve's second outlet 510 to a treatment pad. Fluid returning from the treatment pad may be routed through the hot return valve 140 to the heating block, and/or through the cold return valve 142 to the cooling block. In some embodiments, a thermal contrast therapy device may be configured to route fluid returning from the treatment pad to the heating block 108 and/or the cooling block 116 based, at least in part, on the temperature of the fluid. For example, fluid may be routed to the heating block if the temperature of the fluid exceeds a specified temperature, to the cooling block if the temperature of the fluid does not exceed a specified temperature, and/or fluid may be routed in part to the heating block and in part to the cooling block. A fluid return line temperature sensor 152 (FIG. 1) may be used to ascertain the temperature of the fluid, e.g., for purposes of determining which reservoir(s) to which the fluid shall be routed.

Valves are well known, and any one or more suitable valves may be used in a thermal contrast therapy device. In some embodiments, the hot supply valve 126 and the cold supply valve 130 may be three-way magnetic solenoid valves, and the hot return valve 140 and the cold return valve 142 may be two-way magnetic solenoid valves. In some embodiments, valves may be selected that are constructed from a plastic, composite, or other material having a relatively low specific heat capacity, for example to minimize the thermal mass of the valves. Exemplary magnetic solenoid valves include the Series 3825 three-way valve, and the Series 3826 two-way valve, each of which are available from Spartan Scientific, Boardman, Ohio. In some embodiments, solenoid valve coils 512 generate heat during valve operation. Some solenoid valves may be configured such that fluid flows through the valve coils, in which case heat generated by the coils may affect the temperature of the fluid flowing through such valves. Heat transfer from solenoid valve coils may be of particular concern for cold fluid, for example due to the potentially large temperature differential between the fluid and the coil. As shown in FIG. 5, fluid does not flow through the solenoid valve coils 512, but rather, the solenoid valve coils are positioned adjacent to the valves, and perpendicular to the direction of fluid flow. Such a configuration for solenoid valves may be effective to minimize the amount of thermal mass in thermal communication with the fluid flowing through the valve.

As further shown in FIG. 5, a flow meter 158 may be provided. Flow meters are well known in the art and any suitable flow meter may be used, such as a rotary flow meter available from PendoTECH, Princeton, N.J. A flow meter may be used to control the flow rate of the fluid, for example, to provide customized thermal contrast therapy treatment sequences.

Various fluid lines and other components within a thermal contras therapy device may be insulated, for example, to economize the efficiency of the heating system and/or cooling system. Insulation may also enhance the accuracy and/or precision of a thermal contrast therapy device. In some embodiments, the ability of a thermal contrast therapy device to provide certain treatment sequences may depend, at least in part, on having adequate insulation on fluid lines and other components. For example, insulation may enhance the ability of a device to provide treatment sequences involving rapid changes in the rate of heat transfer and/or rapid transitions between specified measures of heat transfer, with a high degree of precision and accuracy. Any suitable insulation may be used. In some embodiments, fluid lines may be insulated using fiberglass braided sleeves.

Figure 6A:
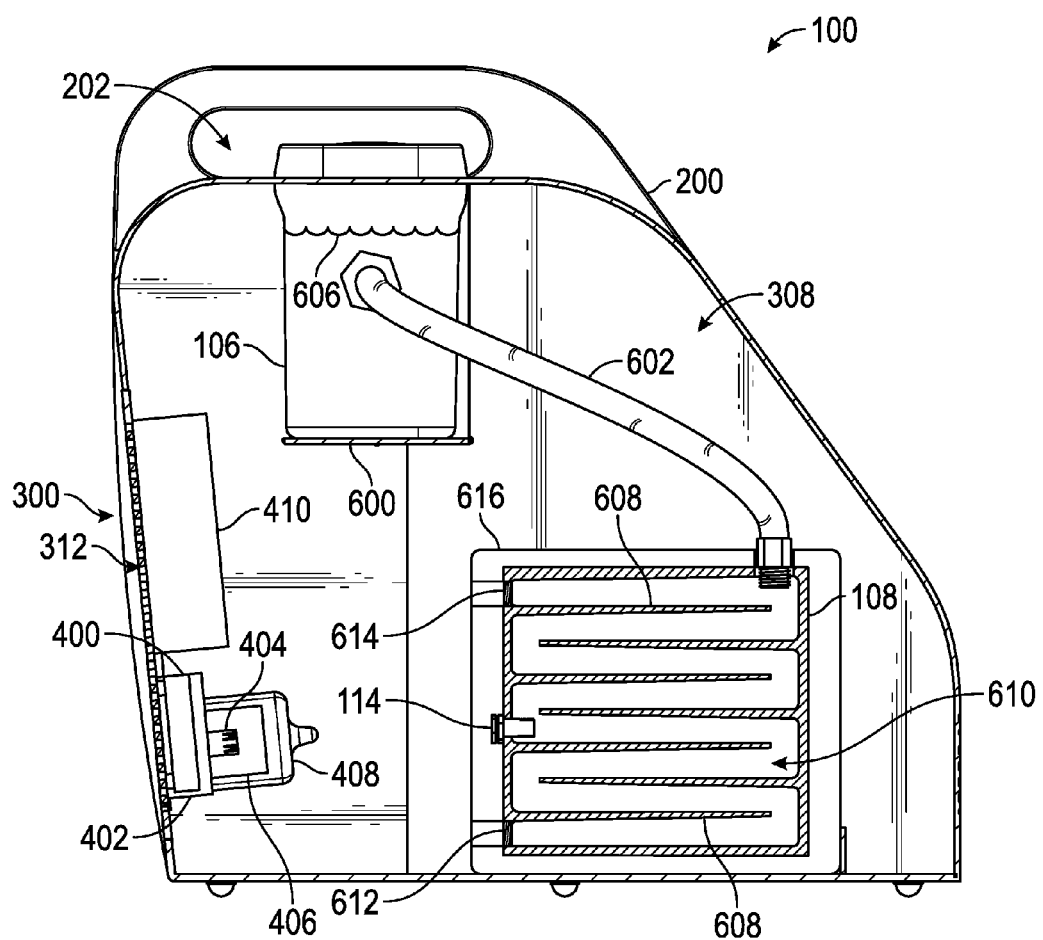
FIGS. 6A and 6B respectively show cross-sectional views from the left side and form the right side of the exemplary thermal contrast therapy device of FIG. 2.
Figure 6B:
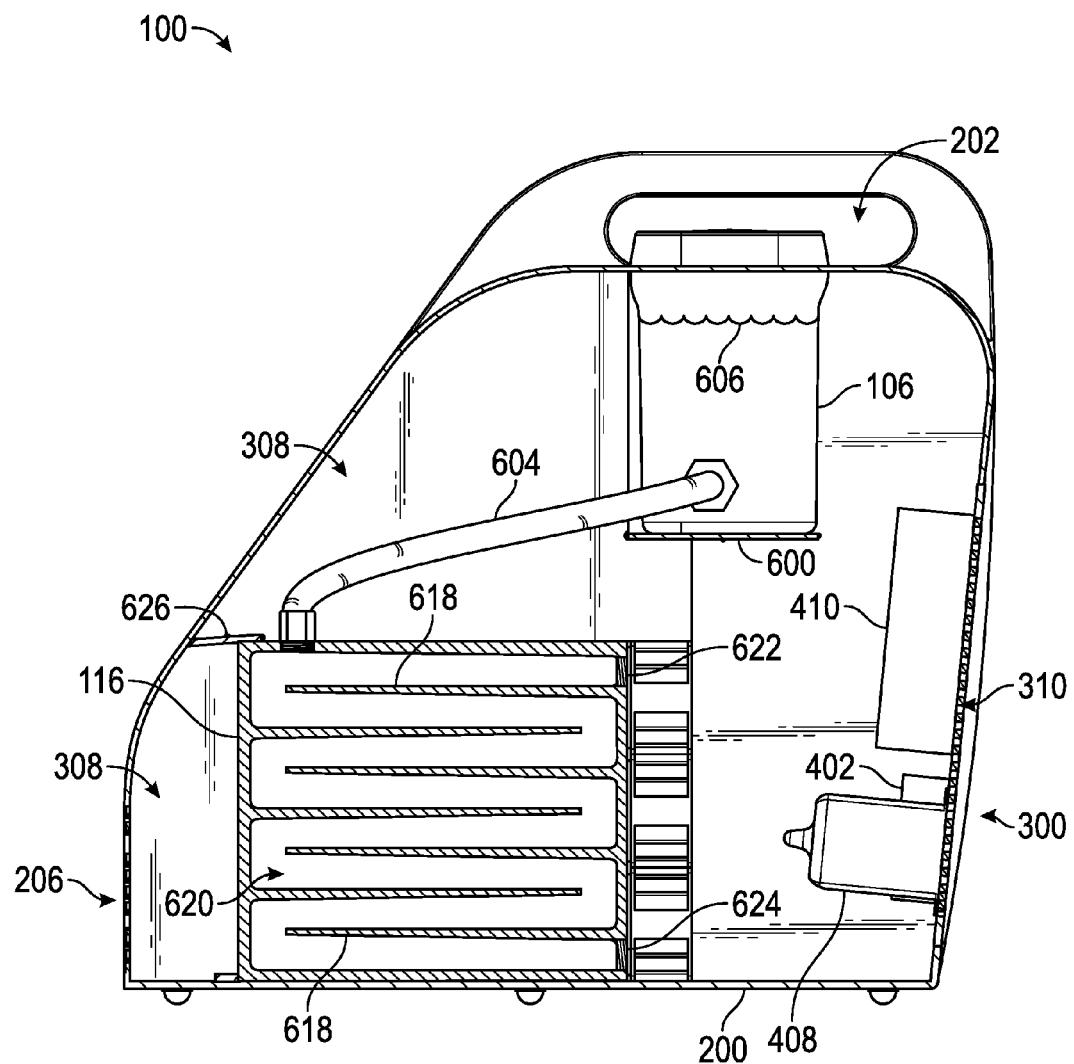

Referring now to FIGS. 6A and 6B, cross-sectional views are shown from the left side and form the right sides of the exemplary thermal contrast therapy device of FIG. 2. FIG. 6A shows a cross-section of the heating block 108, and FIG. 6B shows a cross-section of the cooling block 116. Shared reservoir 106 resides at about a central location within the casing, supported by a bracket 600 and a partition 308 which divides the casing into two zones. Fluid gravity feeds from the shared reservoir to the heating block via a heating block supply line 602, and to the cooling block 116 via cooling block supply line 604. During operation of the device, the heating block and the cooling block will be filled with fluid, and the shared reservoir fluid level 606 will be at least above the top of the interface point between the heating block supply line and the corresponding opening in the shared reservoir. The heating block supply line provides fluid communication with the shared reservoir at about the middle to upper portion of the shared reservoir, and the cooling block supply line provides fluid communication at about the lower portion of the shared reservoir. The supply lines 602, 604 are sloped to allow air to escape to the shared reservoir. The interface points for the supply lines 602, 604 facilitate stratification of hot fluid and cold fluid within the shared reservoir as fluid exchanges between the heating block, the shared reservoir, and the cooling block, during alternating heating periods and cooling periods. These reservoir supply line interface points also allow the heating block and the cooling block to each preferentially draw fluid from stratified hot fluid and cold fluid within the shared reservoir.

In some embodiments, as shown in FIG. 6A, the heating block has a plurality of heating block baffles 608 defining a serpentine path 610 for fluid travel between the heating block inlet 612 and the heating block outlet 614. The heating block baffles may be configured in any desired manner. In some embodiments, a heating block may be provided without baffles. As shown, the heating block inlet may be positioned at a lower elevation of the heating block and the heating block outlet may be positioned at an upper elevation of the heating block. One or more heating elements 114 impart heat energy to the fluid. Heating elements are well known in the art, and any suitable heating element may be used. Such as 12V cartridge heaters. The heating block baffles 608 allow fluid to gradually accumulate heat while traveling through the heating block. As such, the heating block may store fluid having a temperature gradient between the heating block inlet and the heating block outlet. An insulating material 616 may surround all or part of the heating block, which may be effective to improve heating efficiency within the heating block, and/or to protect various other components from heat radiating from the heating block. Closed cell foam may be used as an insulating material.

As shown in FIG. 6B, the cooling block may similarly comprise a plurality of cooling block baffles 618 defining a serpentine path 620 for fluid travel between a cooling block inlet 622 and a cooling block outlet 624. The cooling block baffles may be configured in any desired manner. In some embodiments, a cooling block may be provided without baffles. The cooling block inlet may be positioned at an upper elevation of the cooling block and the cooling block outlet may be positioned at a lower elevation of the cooling block. One or more thermoelectric coolers may be provided to extract heat from the fluid, as described in more detail below. The cooling block baffles 618 allow fluid to gradually cool while traveling through the cooling block. As such, the cooling block may store fluid having a temperature gradient between the cooling block inlet and the cooling block outlet.

Figure 7A:
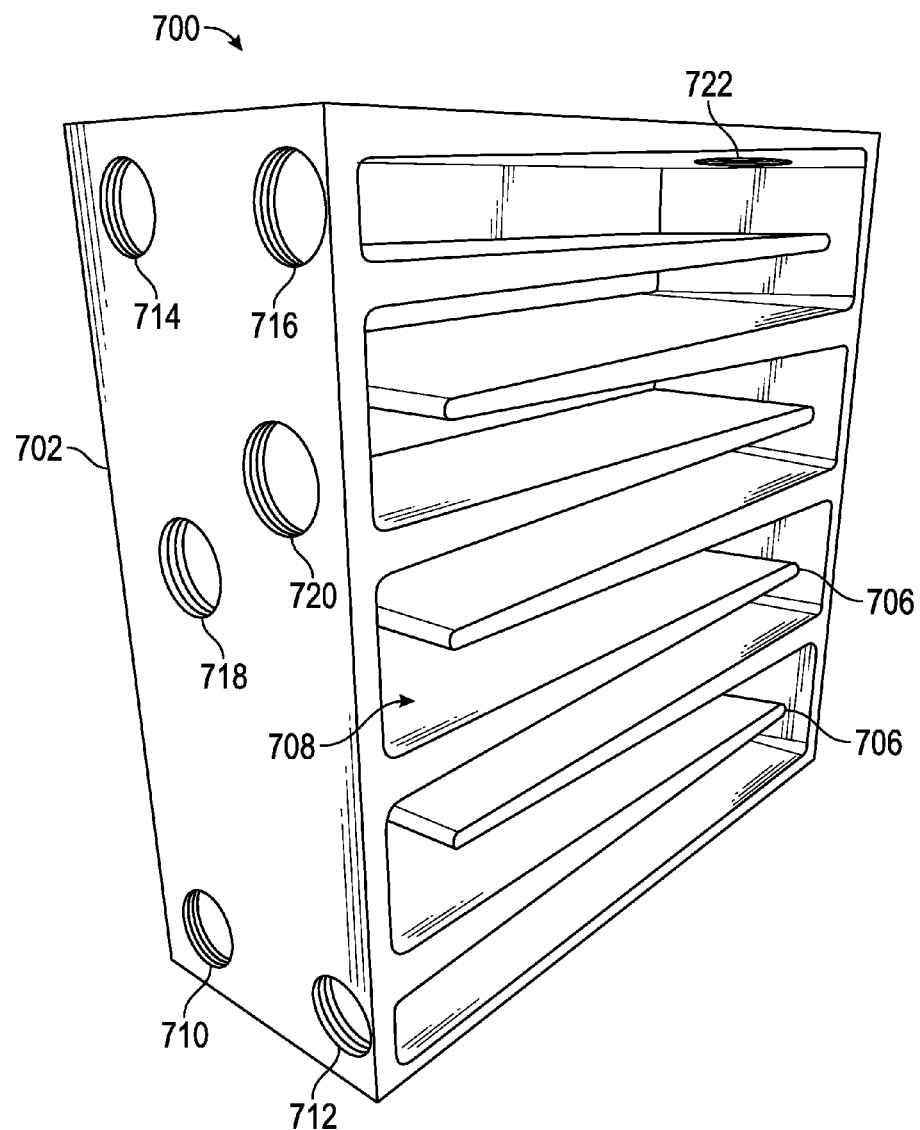
FIGS. 7A and 7B show perspective views of corresponding parts to an exemplary heat transfer block for use in a thermal contrast therapy device.
Figure 7B:
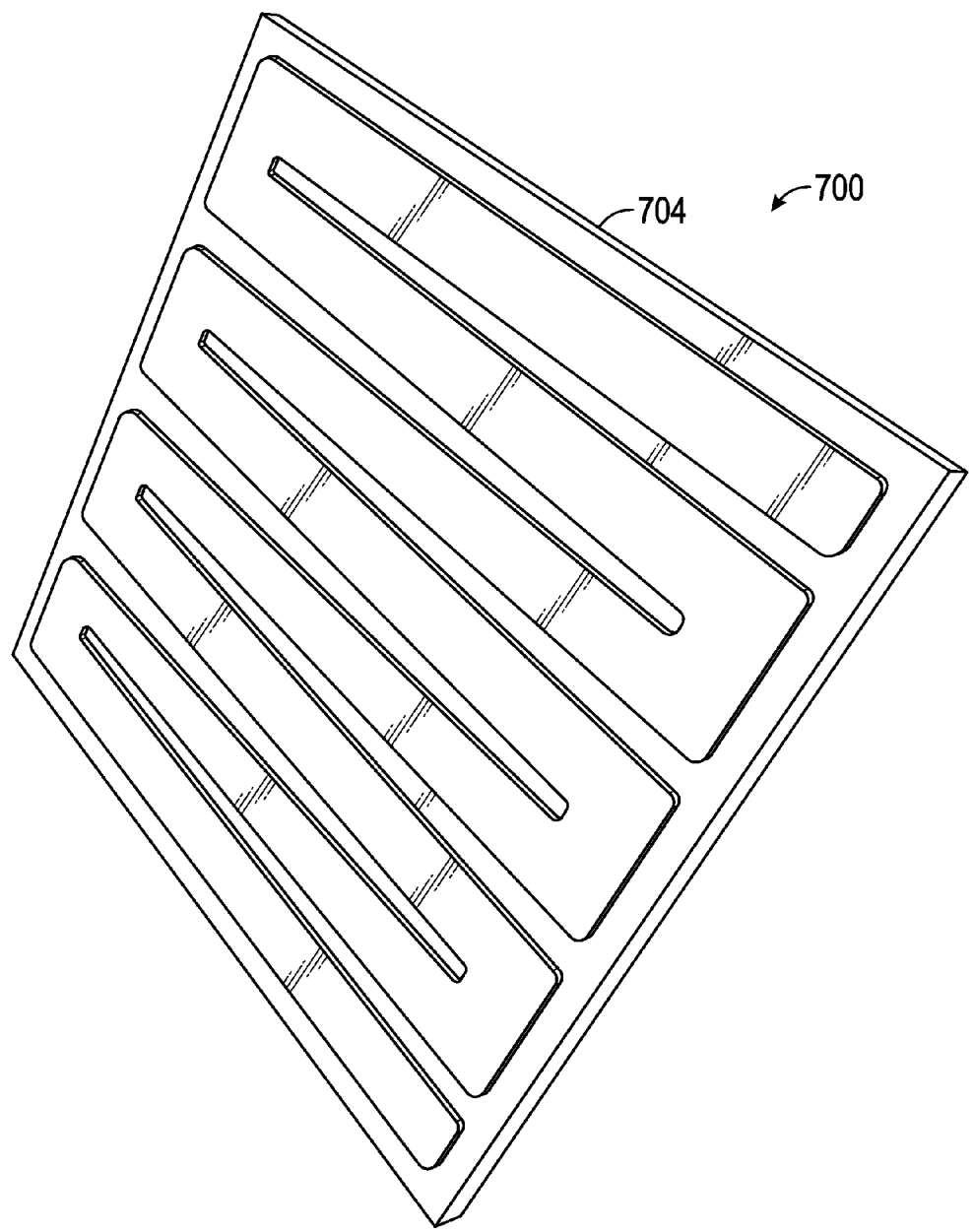

Referring now to FIGS. 7A and 7B, corresponding parts of an exemplary heat transfer block 700 are shown. In some embodiments, the heat transfer block 700 may be used both as a heating block and/or as a cooling block, for example, as shown with respect to the heating block 108 shown in FIG. 6A and the cooling block 116 shown in FIG. 6B. The heat transfer block has a main body 702 (FIG. 7A) and a side cap 704 (FIG. 7B). Both the main body and the side cap may be machined or forged from any desired metal alloy, for example, aluminum alloy. A corrosion resistant surface coating or plating may be applied to the heat transfer block using any suitable corrosion resistant material, including for example, nickel, chrome, zinc, tungsten carbide or other composites, or the like. Such corrosion resistant materials and coating or plating processes are well known in the art. The side cap may be fixedly secured to the main body to form a complete heat transfer block. As shown in FIG. 7A, the heat transfer block has a plurality of baffles 706 defining a serpentine path 708 for fluid travel through the heat transfer block. The baffles 706 may be configured in any desired manner. In some embodiments, a heat transfer block may be provided without baffles. The heat transfer block may be configured with a plurality of orifices for use with various applications. Orifices may be provided for inflow and outflow lines, heating elements, temperature sensors, and other instruments. Unused orifices may be sealed, for example, with a plug. As shown in FIG. 7A, six orifices are provided on the vertical face of the heat transfer block: a first orifice 710 and a second orifice 712 provide access to the bottom channel of the serpentine path, a third orifice 714 and a fourth orifice 716 provide access to the top channel of the serpentine path, and a fifth orifice 718 and a sixth orifice 720 provide access to middle channels of the serpentine path. Such multiple orifices allows a single heat transfer block to be utilized both for the heating block and the cooling block even though different access points may be desired for respective fluid lines and components. In some embodiments, when the heat transfer block of FIG. 7A-B is configured for use as a heating block 108, the first orifice 710 may be used for the heating block inlet 612 and the third orifice 714 may be used for the heating block outlet 614. Heating elements 114 may be installed at the fifth orifice 718 and/or the sixth orifice 720, and a heating block temperature sensor 146 may be installed at the fourth orifice 716, while the second orifice 712 may be sealed, for example, with a plug. In some embodiments, when the heat transfer block of FIG. 7A-B is configured for use as a cooling block 116, the fourth orifice 716 may be used for the cooling block inlet 622, the second orifice 712 may be used for the cooling block outlet 624, and a cooling block temperature sensor 148 may be installed at the first orifice 710, while the third, fifth, and sixth orifices 718, 720, and 714 may be sealed, for example, with a plug. Other heat transfer block configurations, orifice positions thereon, and uses thereof are also within the spirit and scope of the present disclosure.

In some embodiments, the one or more baffles 706 within the heat transfer block may have a sloped surface, for example, as provided by baffles having a cross-sectional thickness at the base which exceeds that of the tip. Such a sloped surface allows air which may be introduced into the heat transfer block to escape through a top orifice 722 at the top of the heat transfer block. When a heat transfer block 700 is configured for use as heating block 108 or as a cooling block 116, the top orifice 722 may be utilized to provide fluid communication with the heating block supply line 602 or the cooling block supply line 604, as applicable. As shown in FIGS. 6A and 6B, the heating block supply line and the cooling block supply line each are sloped to allow air to pass through the supply lines and into the shared reservoir 106.

The baffles 706 of the heat transfer block 700 may be effective to enhance heat transfer with fluid in the block, for example, because the baffles isolate fluid having been heated or cooled to a desired temperature from fluid entering the heat transfer block and having yet to be heated or cooled, as applicable. Given this, the baffles may also be effective to mitigate potential temperature fluctuations in the fluid within the heat transfer block which might otherwise be caused by variations in the temperature of fluid entering the heat transfer block. Such variations in temperature may arise, for example, due to varying measures of heat transfer effected while circulating fluid and/or due to exchanging fluid between the heating block and the cooling block.

In some embodiments, a heating system may be configured to provide fluid having a temperature between about 85° F. to 130° F., or from about 100° F. to 110° F., for example, at least about 85° F., 90° F., 95° F., 100° F., 105° F., 110° F., 115° F., 120° F., 125° F., 130° F., or any intermediate temperature, cooler temperature, or warmer temperature. Other temperatures will also be apparent to the skilled artisan.

Figure 7C:
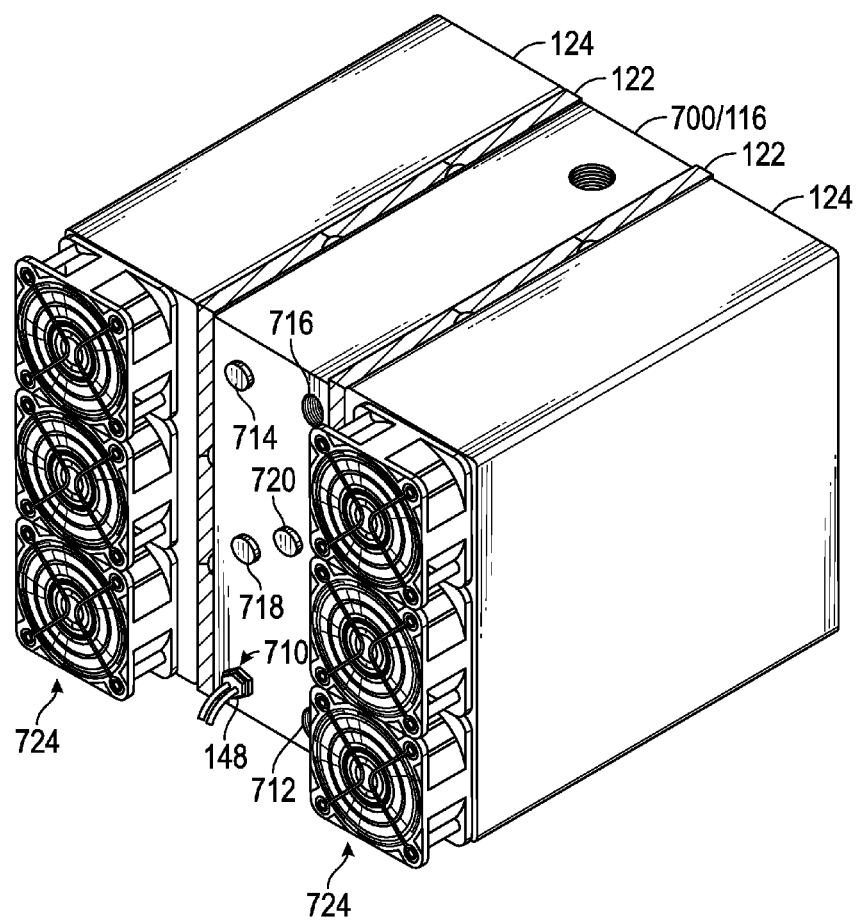
FIG. 7C shows in perspective view, an exemplary embodiment utilizing the heat transfer block of FIGS. 7A and 7B for cooling fluid for use in a thermal contrast therapy device.

Referring now to FIG. 7C, an exemplary embodiment of a cooling block 116 utilizing heat transfer block 700 is shown. The third orifice 716 is used as the cooling block inlet 622, and the first orifice 712 is used as the cooling block outlet 624. A temperature sensor 148 is provided at the first orifice 710. The second orifice 714, the fifth orifice 718, and the sixth orifice 720 each are sealed with a plug. A plurality of thermoelectric coolers 122 are positioned along opposite sidewalls of the cooling block. Heat sinks 124 comprising a plurality of horizontally arranged heat transfer fins (not shown) are provided on opposite sides of the thermoelectric coolers. A plurality of fans 724 are provided to draw air across the heat transfer fins to dissipate heat. Thermoelectric coolers are well known, and any suitable thermoelectric coolers may be used. In the exemplary embodiment shown in FIG. 7C, six (6) thermoelectric coolers are provided on each side of the heat transfer block, each measuring approx. 16 sq. cm. Suitable thermoelectric coolers are available from TE Technology, Inc., Traverse City, Mich. Heat sinks are also well known and any suitable heat sinks may be used. Suitable fans are available from Newark element14, Chicago, Ill. It will be appreciated that the heat transfer capacity of the thermoelectric coolers and heat sinks may be selected for the desired operating range of a thermal contrast therapy device.

In some embodiments, a cooling system may be configured to provide fluid having a temperature between about 30° F. to 70° F., or from about 40° F. to 50° F., for example, less than at least about 30° F., 35° F., 40° F., 45° F., 50° F., 55° F., 60° F., 65° F., 70° F., or any intermediate temperature, cooler temperature, or warmer temperature. Other temperatures will also be apparent to the skilled artisan.

In some embodiments, the thermal contrast therapy device may be configured so as to cause the heat sink fans 724 to draw air from outside of the casing, thereby avoiding recirculation of air from within the casing, which may otherwise affect cooling efficiency. For example, heat sinks 124 on opposite sides of the cooling block may respectively rest snugly against the sidewall of the casing 200 and the partition 308 (FIG. 3), and optionally, a seal 626 (FIG. 6B), may be provided so as to form a duct that directs airflow from the vents 206 to the heat sinks and out of the casing through vents 310 (FIG. 3). The seal may span the substantial distance between the sidewall of the casing and the partition 308, thus assuring that the fans draw fresh air from outside of the casing.

The skilled artisan will appreciate that the size of heat transfer block 700 for use as a heating block and/or as a cooling block in a thermal contrast therapy device may be determined based on a number of factors, including intended use of the thermal contrast therapy device, and the desired heating capacity or cooling capacity of the heating system or cooling system, as applicable. In some embodiments, the heat transfer block may be configured to hold a fluid volume of between about 5 to 100 ounces, for example, about 5 ounces, 10 ounces, 20 ounces, 30 ounces, 40 ounces, 50 ounces, 60 ounces, 70 ounces, 80 ounces, 90 ounces, or 100 ounces.

Fluid for a thermal contrast therapy device may comprise any suitable heat transfer medium. In some embodiments, the fluid may include an anti-freeze or anti-boil agent such as ethylene glycol, propylene glycol, glycerol, or combinations thereof. The fluid may also include a corrosion inhibitor. The fluid may be dyed, for example, so that it may be easily viewed within transparent, semi-transparent, or translucent fluid lines and/or treatment pads. In some embodiments, the fluid may comprise a thermochromic material, such as a reversible thermochromic pigment. The thermochromic material may provide a visual indication as to the temperature of fluid within a fluid line or treatment pad, for example, to indicate transitions between heating periods and cooling periods and/or to indicate that the fluid is within a desired temperature range. In some embodiments, a thermochromic film may be provided on fluid lines and/or treatment pads, in addition or as an alternative to providing a thermochromic pigment within the fluid. Suitable thermochromic pigment are available from OliKrom, Pessac, France.

Treatment Pads

Thermal contrast therapy generally may be administered via one or more treatment pads applied to a patient's body. The thermal contrast therapy devices disclosed herein may be configured to function with a plurality of different treatment pads. A treatment pad may comprise a network of interconnected cells or capillaries or a serpentine conduit, or combinations thereof, with an inflow port configured to receive fluid via an inflow tube, and outflow port configured to return fluid via an outflow tube. Various shapes and sizes of treatment pads may be provided in order to accommodate different patient sizes and/or different areas of the body, and/or in order to accommodate or integrate with various orthopedic braces, casts, and other devices.

Figure 8A:
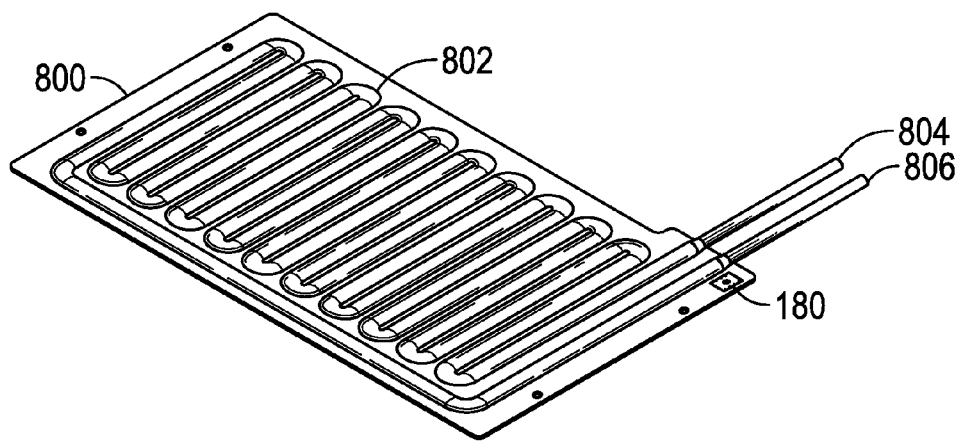
FIG. 8A shows an exemplary treatment pad for administering thermal contrast therapy.
Figure 8B:
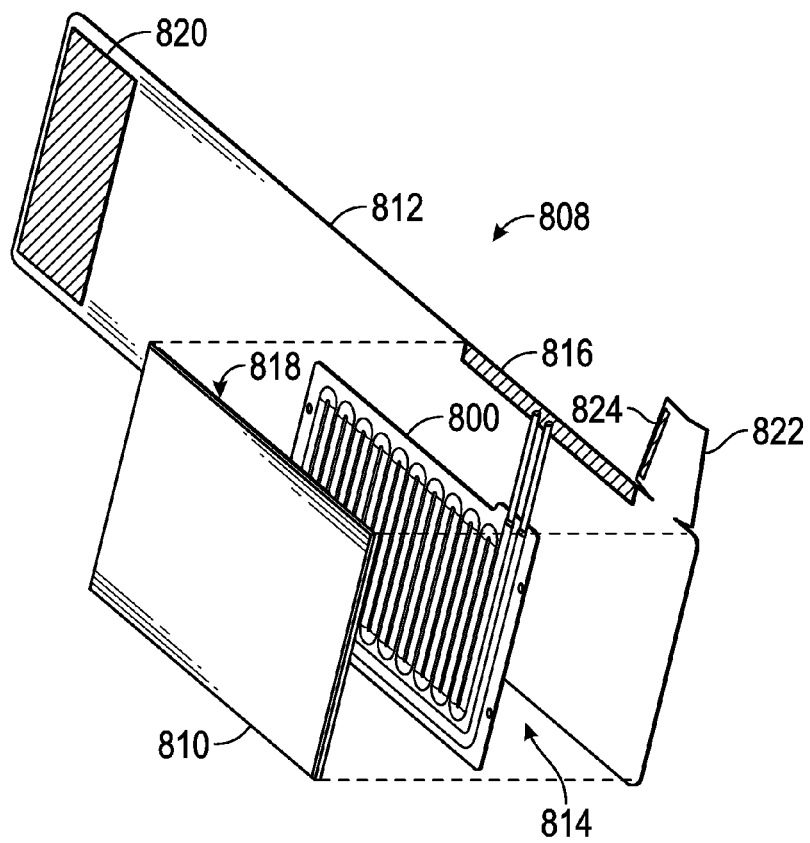
FIG. 8B shows a perspective, exploded view of an exemplary cuff configured to receive a treatment pad, such as the treatment pad of FIG. 8A.

FIG. 8A shows an exemplary treatment pad 800 having a serpentine conduit 802 occupying a substantial surface area of the treatment pad. During thermal contrast therapy, fluid enters the treatment pad through an inflow port 804, then passes through the serpentine conduit, and then exits the treatment pad through an outflow port 806. In some embodiments, a treatment pad is configured such that the inflow port corresponds to the side of the serpentine conduct which provides the shortest distance to the central region of the treatment pad. A treatment pad may be formed from a pair of thermoplastic panels which may be sealed together by conductive heat fusion, a process which is well known in the art. The thermoplastic panels may be formed from polyurethane, polyvinyl chloride, or any other suitable material.

The serpentine conduit 802 allows fluid within the pad to be displaced by fresh fluid entering the pad. By contrast, a treatment pad having a network of interconnected cells or capillaries may allow fluid within the pad to mix with fresh fluid entering the pad. In some embodiments, a treatment pad having a serpentine conduit allows for more rapid transitions between alternating heating periods and cooling periods. A treatment pad having a serpentine conduit may be transitioned from a first period to a second period of a thermal contrast therapy treatment sequence at least as quickly as the duration of time determined by dividing the volume of fluid in the treatment pad by the flow rate of the fluid passing through the serpentine conduit. In some embodiments, such volume of fluid may be reduced by a volume corresponding to portions of the treatment pad which are not in substantial thermal communication with the patient's body. In some embodiments, such calculated duration of time for effecting a transition may also account for the volume of fluid in outflow fluid line 136 and/or supply line 168 or a portion thereof, and/or other components from within which fluid is to be displaced upon transition between periods. Such calculated duration of time may also account for time required to overcome thermal loading of system components from the previous period. By contrast, in some embodiments, a treatment pad having a network of interconnected cells or capillaries may provide a more gradual transition between alternating heating periods and cooling periods.

In some embodiments, a pad ID tag 180 may be embedded within a treatment pad. Alternatively, in some embodiments a pad ID tag 180 may be embedded within a fitting configured to be attached to a treatment pad, such as a pad interface fitting, as discussed below. A thermal contrast therapy device may be configured to receive an indication from a pad ID tag effective to identify a treatment pad operably connected to the thermal contrast therapy device, thereby enabling the thermal contrast therapy device to acquire information about the particular treatment pad operably connected to the device, and/or to perform a treatment sequence that is calibrated for the particular treatment pad operably connected to the device. For example, a pad ID tag may transmit an indication that a treatment pad is configured for use with a given body part, and upon a thermal contrast therapy device having received such indication, the device may perform a treatment sequence intended to treat such body part. In some embodiments, by identifying the particular treatment pad operably connected to the device, a substantially similar treatment sequence may be provided using any one of a plurality of different treatment pads, notwithstanding differences in the dimensional or physical characteristics of such treatment pads. This includes, for example, effecting a desired measure of heat transfer between the fluid and the patient's tissue, using any one of a plurality of various treatment pads. A pad ID tag 180 may be a microchip, RFID tag, RUBEE® tag, UWB tag, ZIG-BEE® tag, or other suitable component capable of enabling a tag reader or processor to identify at least one characteristic of a treatment pad. In some embodiments, for example, in lieu of a pad ID tag, a treatment pad may be identified manually, for example by an input via a user interface.

Once a particular treatment pad has been identified by a thermal contrast therapy device, operating parameters of the device may be automatically adjusted so as to correspond to one or more characteristics of the particular treatment pad operably connected to the device. With some treatment sequences, treatment pads having various dimensional or physical characteristics may require different fluid flow rates and/or fluid temperatures in order to deliver desired treatment conditions. For example, as between various treatment pads, some treatment sequences may require different flow rates and/or fluid temperatures in order to effect a specified measure of heat transfer (i.e., a quantity of heat and/or a rate of heat transfer) as called for by the treatment sequence. A thermal contrast therapy device may be configured to automatically adjust one or more parameters of a treatment sequence based, at least in part, on one or more characteristics of a particular treatment pad. Such adjustments may be configured to enable a thermal contrast therapy device to effect a given treatment sequences consistently across a plurality of different treatment pads having various dimensions and/or configurations, for example, by varying the temperature and/or flow rate of the fluid as between various treatment pads, based, at least in part, on one or more characteristics of a given treatment pad operably connected to the device. Such automatic adjustments enable a thermal contrast therapy device to provide enhanced accuracy, precision, and control of treatment sequence parameters across a plurality of various treatment pads.

In some embodiments, one or more temperature sensors may be positioned at various locations on or within a treatment pad. Such temperature sensor(s) may be configured to measure the temperature of the patient's tissue proximate to the treatment cuff. Additionally and/or in the alternative, one or more temperature sensors may be configured to measure the temperature of fluid at a given point within the treatment cuff. Such temperature measurements may be used to provide customized thermal contrast therapy treatment sequences.

In some embodiments, a cuff may be provided for securing a treatment pad to an area of a patient's body. Cuffs of various shape or sizes may be provided, to accommodate different treatment pads and/or to fit different parts of the body or different sized patients. For example, FIG. 9 shows a perspective, exploded view of a cuff 808 configured to receive the treatment pad of FIG. 8A. The cuff 808 comprises a contact surface 810, secured on three sides to a main wrap 812 so as to create a pocket 814 configured to receive the treatment pad. Hook and loop fastener elements 816, 818 may be provided on opposite sides of the contact surface and the main wrap to secure the treatment pad within the pocket. The contact surface may be fabricated from a thin material such as perforated nylon mesh, or any other material that may provide a comfortable surface to the touch while also minimizing interference with heat conduction. A first hook-fastener element 820 may be provided at the end of the cuff to allow the cuff to be removably secured around a body part of a patient. The main body may be fabricated from a material configured to catch the first hook-fastener element 820, for example, hook-compatible neoprene such as airprene, thus providing an adjustable fit. The main body may be configured with an extension element 822 to wrap around the inflow port 804 and outflow port 806 of the treatment pad. The extension element may be removably secured with a second hook-fastener element 824, so as to provide insulation and/or structural support to the inflow port and the outflow port.

Figure 8C:
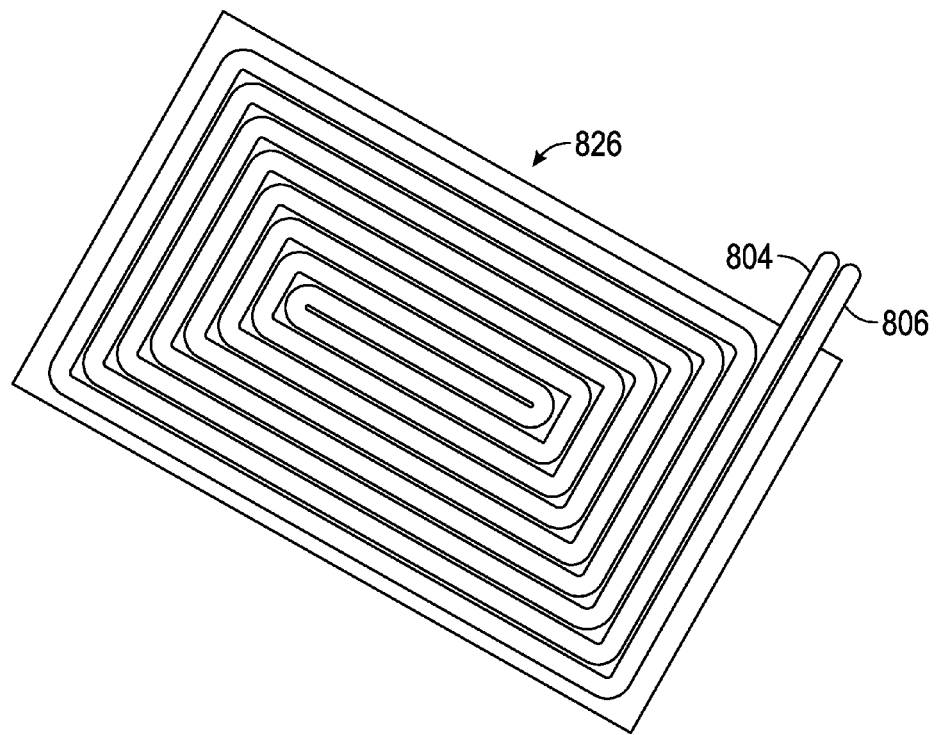
FIGS. 8C and 8D show additional exemplary treatment pads for administering thermal contrast therapy.

The serpentine conduit or network of interconnected cells or capillaries within a treatment pad may be formed in any desired configuration. A serpentine conduit may embody a variety of different conduit patterns or combinations of patterns. As shown in FIG. 8A, a serpentine conduit may comprise a plurality of hairpin corners, thus directing fluid back and forth across the pad. In some embodiments, as shown in FIG. 8C, a serpentine conduit may comprise a Fermat's spiral 826, thus directing fluid in a spiral pattern that doubles-back on itself. In some embodiments, as shown in FIG. 8C, a serpentine conduct may comprise a modified Fermat's spiral 828, in which fluid follows a pattern comprising a spiral pattern that doubles-back on itself and a plurality of hairpin corners.

During thermal contrast therapy, resulting heat transfer between the fluid and a patient's tissue changes the temperature of fluid passing through a treatment pad. Thus, the temperature of fluid at inflow port 804 may differ from the temperature of fluid at outflow port 806. Similarly, the temperature of fluid may differ as between any two points within a treatment pad. The rate of heat transfer effected by the fluid depends on fluid temperature, and as such, the rate of heat transfer may differ as between two points within a treatment pad. Consequently, some treatment pad configurations may yield a perceptible or measurable difference in the rate of heat transfer as between two regions of the treatment pad.

Figure 8D:
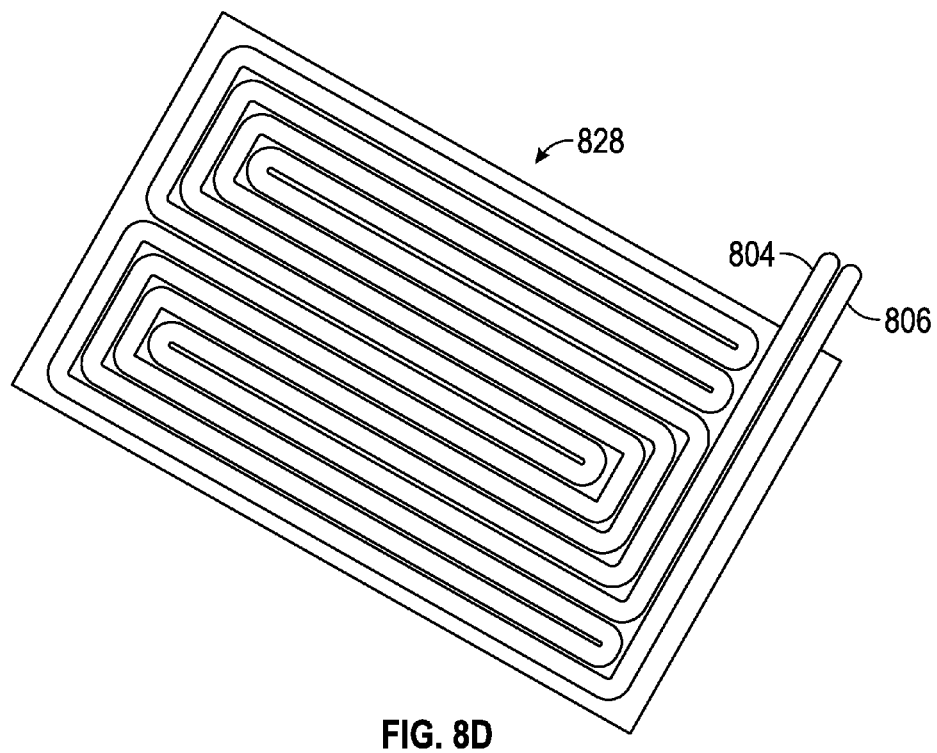

In some embodiments, a treatment pad may be provided having a configuration effective to provide a substantially uniform rate of heat transfer across the effective surface area of the treatment pad. A treatment pad having a serpentine conduit, for example, a serpentine conduit having a Fermat's spiral configuration, may be effective to provide a substantially uniform rate of heat transfer across the effective surface area of the treatment pad. In some embodiments, a treatment pad may be provided having a configuration effective to impart a substantially uniform rate of heat transfer as between various regions of the treatment pad, for example, as between a first region and a second region. The rate of heat transfer of a first region and a second region may in some embodiments be within less than about 5%, 4%, 3%, 2%, or 1% of one another. In some embodiments, a treatment pad may be configured such that the temperature of fluid entering the pad is conductively tempered through countercurrent conductive heat transfer between an adjacent aspect of the pad. For example, fluid having traveled a first distance through the serpentine conduit may be conductively tempered by fluid having traveled a second distance through the serpentine conduit. Conductive tempering of fluid may occur, for example, due to countercurrent conductive heat transfer as between any adjacent points within a treatment pad, and may be effective to allow a treatment pad to impart a substantially uniform rate of heat transfer as between various regions of the treatment pad. In some embodiments, when a serpentine conduit having a Fermat's spiral (e.g., FIG. 8C) is provided, a first aspect of the serpentine conduit located a linear distance along the conduit from the inflow port 804 may be adjacent to a second aspect of the serpentine conduit that is located an approximately equivalent linear distance along the conduit from the outflow port 806. With such a configuration, the temperature gradient between fluid passing the first aspect and fluid passing the second aspect will tend to be approximately proportional to the linear distance along the serpentine conduct between the first aspect and the second, with such temperature gradient decreasing as such linear distance decreases. As such, in some embodiments, a serpentine conduct having a Fermat's spiral configuration may be effective to maximize countercurrent conductive heat transfer, thereby minimizing relative temperature differences across various aspects of the treatment pad. In some embodiments, with a serpentine conduit having a modified Fermat's spiral (e.g., FIG. 8D), fluid flow alternates between a left region and a right region of a treatment pad, such that entering inflow port 804 serpentines a plurality of times through both the left region and the right region of the treatment pad before having traveled past the point in the serpentine path which is equidistant from the fluid inflow port and the fluid outflow port 806. Likewise, fluid having passed such equidistant point along the serpentine path further serpentines a plurality of times through both the left region and the right region of the treatment pad before exiting the fluid outflow port 806. With such a configuration, fresh fluid may be uniformly distributed through the surface area of the treatment pad, which may be effective to minimize the time required to supply a specified fluid temperature and/or measure of heat transfer with the patient's tissue across a substantial distribution of the treatment pad.

Quick Release Extension Cords

Referring now to FIGS. 9A-9C, FIG. 10, and FIG. 11, an exemplary quick-release extension cord for providing fluid and data communication between a thermal contrast therapy device and a treatment pad (FIGS. 9A-9C) and corresponding device interface fitting (FIG. 10) and pad interface fitting (FIG. 11) will now be discussed.

Figure 9A:
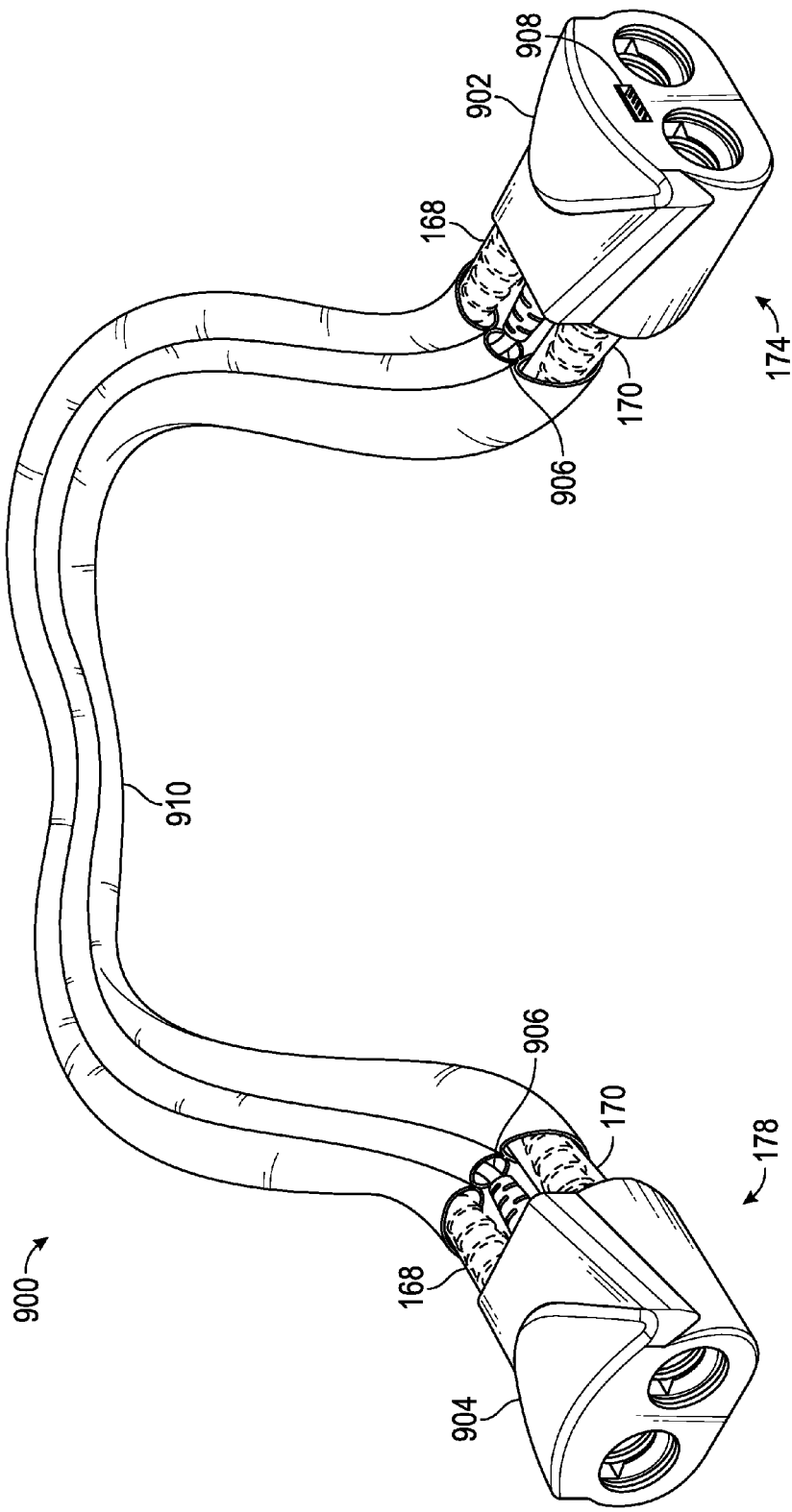
FIG. 9A shows a perspective view of an exemplary quick-release extension cord for providing fluid and data communication between a thermal contrast therapy device and a treatment pad.

FIG. 9A shows a perspective view of exemplary quick-release extension cord 900 for providing fluid and data communication between a thermal contrast therapy device and a treatment pad. A device-side fitting 174 releasably couples with the device interface fitting of FIG. 10, and pad-side fitting 178 releasably couples with the pad interface fitting of FIG. 11. Supply line 168 and return line 170 provide fluid communication between the device-side fitting and the pad-side fitting, such that when attached to the device interface fitting 172 and the pad interface fitting 176, the extension cord provided fluid communication between the thermal contrast therapy device and the treatment pad. Quick-release buttons 902, 904 on opposite ends of the extension cord respectively release prongs within the device-side fitting and the pad-side fitting, which snap into place over corresponding notches on the device interface fitting 210, 212 (FIG. 10) and the pad interface 1104, 1106 (FIG. 11). Fluid lines 168, 170 attach to hose barbs on opposite ends of the device interface fitting and the pad interface fitting. A data cable 906 runs between a data plug 908 configured to mate with data fitting 214, and a pad ID reader 182 (FIGS. 9B-9C) embedded within the pad-side fitting 178 as discussed below. A housing 910 surrounds the supply line, return line, and data cable, to insulate the fluid in the supply line and return line and/or to prevent the various lines from becoming tangled. As shown in FIG. 9A, the housing is cut-away slightly from the device-side fitting 174 and the pad-side fitting 178 so as to partially show the supply line, return line, and data cable. In some embodiments, the housing may be partitioned, as shown in FIG. 9A, with different segments provided for the fluid supply line and return line. The housing and may be configured from any suitable material, for example a fabric or a plastic. Insulation may be provided within the housing, for example, to insulate the fluid supply line and return line from the outside elements and/or from one another. Insulation is well known, and any suitable insulation may be used, such as closed-cell foam, elastomeric materials, fiberglass, or the like.

Figure 9B:
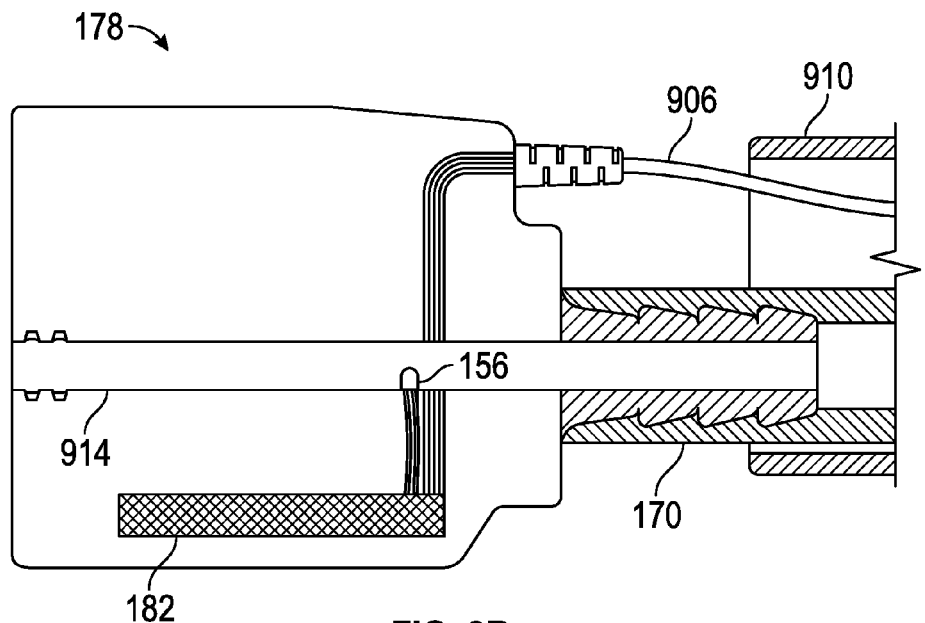
FIG. 9B shows a cross-sectional side view of the pad-side fitting of the quick-release extension cord of FIG. 9A.
Figure 9C:
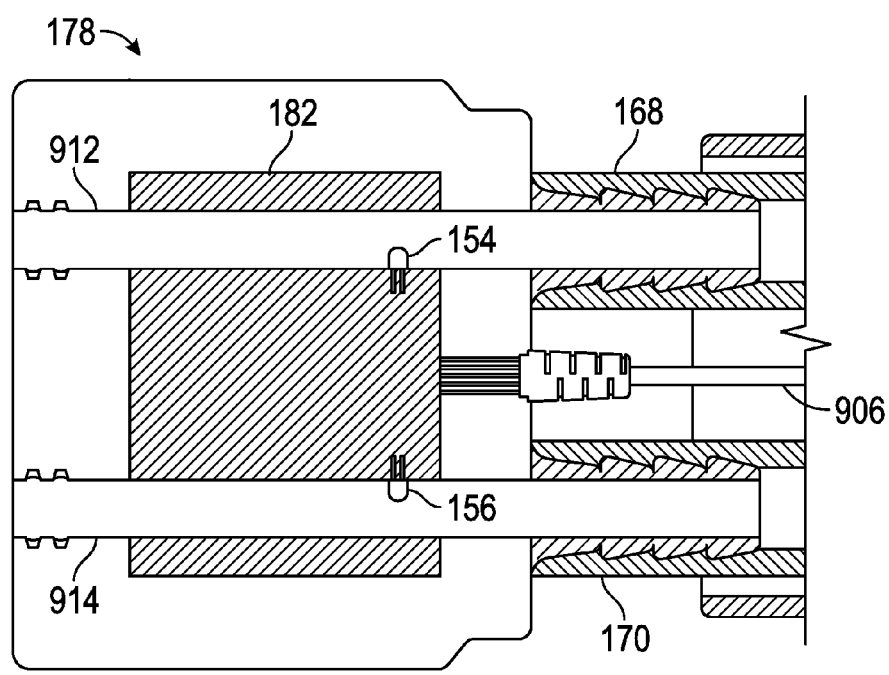
FIG. 9C shows a cross-sectional top view of the pad-side fitting of the quick-release extension cord of FIG. 9A.

FIGS. 9B and 9C respectively show a cross-sectional side view and a cross-sectional top view of the pad-side fitting of the quick-release extension cord of FIG. 9A. Fluid from supply line 168 flows through a supply channel 912 to a treatment pad, and fluid from the treatment pad flow through a return channel 914. Temperature sensors 154, 156 measure the temperature of fluid passing through the supply channel and return channel, respectively. Such temperature sensors, being proximately located to the inflow port 804 and outflow port 806 of a treatment pad (FIG. 8A), may be used to measure the temperature of fluid entering and exiting the treatment pad and the corresponding change in temperature may be used for calculating the measure of heat transfer effected by fluid passing through the treatment pad. The skilled artisan will appreciate that for purposes of measuring the temperature change of the fluid between the entrance and exit of the treatment pad, temperature measurements obtained at or near the inflow port and/or the outflow port of the treatment pad may be more accurate than measurements obtained at more distant locations. This may be of particular concern to the artisan when performing a treatment sequence requiring a high degree of precision, for example, a treatment sequence configured to effect a desired measure of heat transfer. In some embodiments, the pad-side fitting includes a built-in pad ID reader 182, which may be coupled to a data cable 906, for example, to transmit data to a thermal contrast therapy device. Temperature sensors 154, 156 may also be coupled to the pad ID reader, or such sensors may be directly coupled to a data cable leading to the thermal contrast therapy device. In some embodiments, the pad ID reader may include a local processor configured to perform various desired operations, for example using data collected from a pad ID tag, temperature sensors, or other sources.

A quick release extension cord 900 may be any desired length, for example, between about 3 feet to 12 feet, about 3 feet to 6 feet, or about 4 feet to 8 feet. In some embodiments, a quick release extension cord may be at least about 3 feet, 4 feet, 5 feet, 6 feet, 7 feet, 8 feet, 9 feet, 10 feet, 11 feet, 12 feet, or longer.

Figure 10:
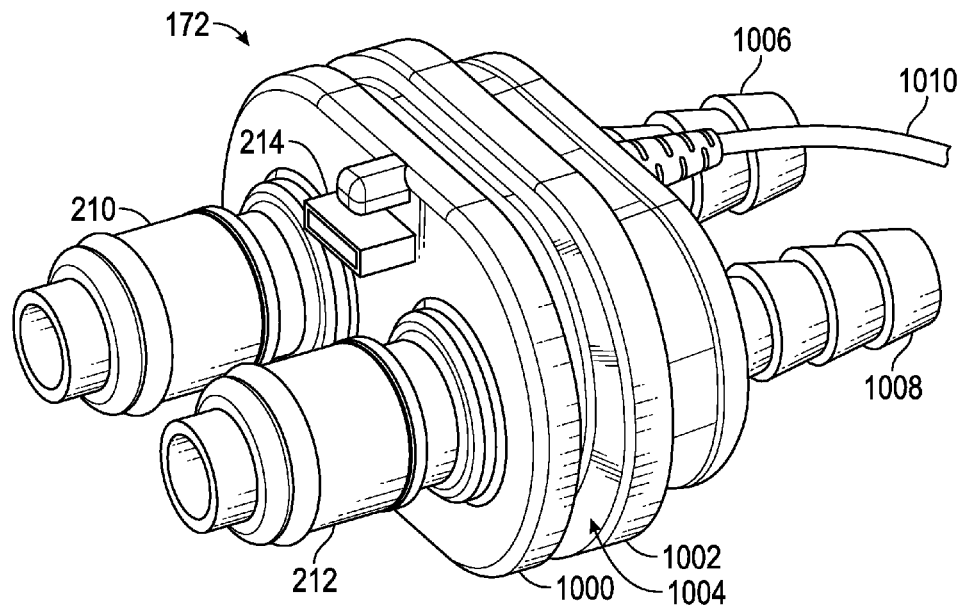
FIG. 10 shows a perspective view of an exemplary device interface fitting for coupling the quick-release extension cord of FIGS. 9A-C to a thermal contrast therapy device.
Figure 11:
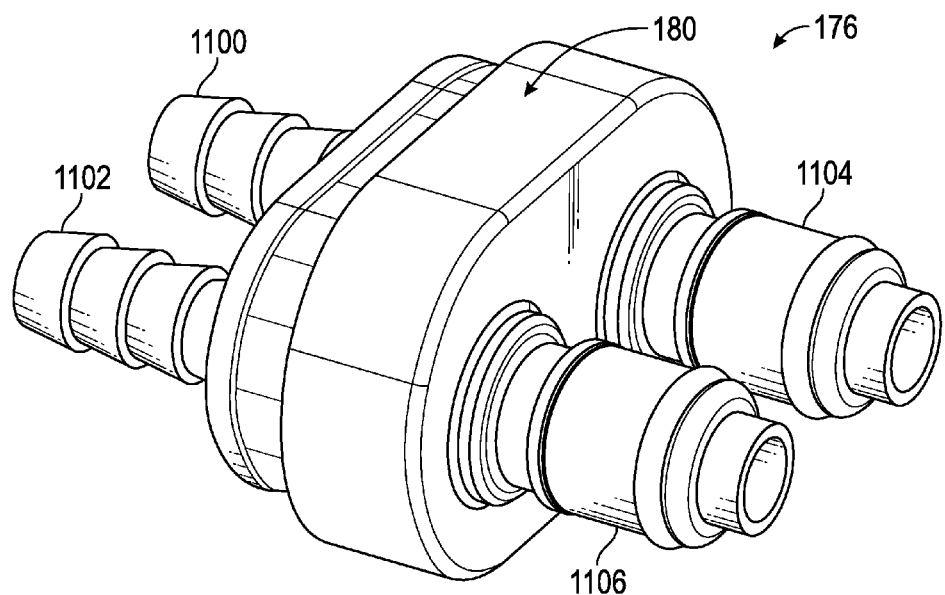
FIG. 11 shows a perspective view of an exemplary pad interface fitting for coupling the quick-release extension cord of FIGS. 9A-C to a treatment pad.

FIG. 10 shows a perspective view of an exemplary device interface fitting 172 for coupling fluid lines and a data line to a thermal contrast therapy device. The device interface fitting spans an opening in the casing of the thermal contrast therapy device 100 (FIG. 2). Flanges 1000, 1002 reside on opposite sides of the opening in the casing, with a notch 1004 receiving the perimeter of the opening, so as to secure the device interface fitting in place. An outflow fluid line 136 and return fluid line 138 may be secured to respective hose barbs 1006, 1008 on the device interface fitting. A supply line fitting 210 and a return line fitting 212 may releasably couple with corresponding fluid-line receptacles on a device-side fitting 174. Similarly, a data fitting 214 may interface with a corresponding cable receptacle on the device-side fitting. A device-side data cable 1010 coupled to data fitting 214 provides data communication to the thermal contrast therapy device.

FIG. 11 shows a perspective view of an exemplary pad interface fitting 176, for coupling fluid lines to a treatment pad. The inflow port 804 and outflow port 806 of a treatment pad (FIG. 8A) attach to respective hose barbs 1100, 1102, and fittings 1104, 1106 releasably couple with corresponding receptacles on the pad-side fitting 178. In some embodiments, a pad ID tag 180 such as a microchip, RFID tag, RUBEE® tag, UWB tag, ZIGBEE® tag, or other wireless transmitter may be embedded within the pad interface fitting. The pad ID tag may be configured to enabling a tag reader or processor to identify at least one characteristic of a treatment pad to which the pad-interface fitting is attached and which may be operably connected to a thermal contrast therapy device.

Temperature Control

In some embodiments, a processor 144 may be configured to control the temperature of the fluid, utilizing temperature measurements from any one or more temperature sensors. For example, temperature sensors 154 and/or 156 within the quick release extension cord 900 may be used to control the temperature of the fluid based on the temperature of the fluid entering or exiting the treatment pad, respectively. Additionally or in the alternative, fluid temperature may be controlled based on the temperature of the patient's tissue proximate to the treatment pad and/or the temperature of the fluid at a given point within the treatment pad. Such temperature control may be configured to enable a thermal contrast therapy device to provide customized treatment sequences based, at least in part, on fluid temperature.

Customized thermal contrast therapy treatment sequence may be provided, for example, by varying the temperature of the fluid during heating periods and/or cooling periods, and providing fluid of a desired temperature to a treatment pad. In some embodiments, the temperature of the fluid in the heating block 108 and/or the cooling block 116 may be increased or decreased during the course of a thermal contrast therapy treatment so as to provide fluid having a desired temperature during the various heating periods and/or cooling periods. Alternatively, the respective temperatures of the hot fluid and cold fluid may be maintained relatively constant, and the two fluids may be mixed in various proportions to provide a desired fluid temperature. Such mixing allows a thermal contrast therapy device to provide a range of desired fluid temperatures depending on the degree of mixing, without having to repeatedly heat or cool a reservoir of fluid to the desired temperature. Thus, during a heating period, hot fluid may be tempered with a measure of cold fluid via cold supply valve 130 so as to attain a desired fluid temperature at the treatment pad. Similarly, during a cooling period, cold fluid may be tempered hot supply valve 126 with a measure of hot fluid.

Flow Control

In some embodiments, a processor 144 may be configured to control the flow rate of the fluid that circulates through a thermal contrast therapy device and/or a treatment pad, utilizing flow measurements from any one or more flow meters. For example, a flow meter 158 may be configured to measure the flow rate of fluid in the outflow fluid line 136. The flow rate of fluid circulating through a thermal contrast therapy device may be varied to control the measure of heating and/or cooling that takes place in the heating block and cooling block, respectively. The flow rate of fluid circulating through a treatment pad may be controlled in order to effect a specified measure of heat transfer between fluid in the treatment pad and a patient's tissue. In some embodiments, the flow rate of the fluid may be controlled, at least in part, by varying the speed of one or more pumps 110, 118, for example by adjusting the power supplied to the respective motors 112, 120 via pulse width modulation technology. Alternatively or in addition, the flow rate of fluid may be controlled, at least in part, using one or more valves. For example, the flow rate of fluid that passes through a magnetic solenoid valve may be controlled by pulsing the valve between open and closed positions at a given frequency. The flow rate of hot fluid that circulates through a treatment pad may be controlled by varying the proportion of fluid flowing through the first outlet and second outlet of hot supply valve 126, for example, by providing a pulse sequence for the first outlet and the second outlet effective to yield the desired flow rate to the treatment pad. Similarly, the flow rate of cold fluid that circulates through a treatment pad may be controlled by varying the proportion of fluid flowing through the first outlet and second outlet of cold supply valve 130. Such flow rate control may be configured to enable the device to provide customized thermal contrast therapy treatment sequences based, at least in part, on fluid flow rate. In some embodiments customized thermal contrast therapy treatment sequences may be based, at least in part, on both flow rate and temperature of the fluid.

Pulsation and Compression

In some embodiments, a thermal contrast therapy device may be configured to provide pulsation in the treatment pad and/or compression of the cuff. Such pulsation and/or compression may be provided during all or part of a treatment sequences. Pulsation may be provided by cycling one or more valves within the thermal contrast therapy device between the open and closed position. The hot supply valve 126, the cold supply valve 130, the hot return valve 140, and/or the cold return valve 142 may be used to provide pulsation. In some embodiments, one or more magnetic solenoid valves may be used to generate a pressure pulse in the fluid. The pressure pulse may be generated by cycling a magnetic solenoid valve between opened and closed positions. The frequency of the pressure pulse may be controlled based on the timing between opening and closing events of the one or more valves. In addition to magnetic solenoid valves and peristaltic pumps, other means for generating pressure pulses are within the scope of the present disclosure.

In some embodiments, a treatment cuff may be configured to provide compression during the thermal contrast therapy. Compression enhances the contact between the treatment pad and the patient's tissue, thereby providing a more efficient heat transfer between the fluid and the patient's tissue. Compression may be provided, for example, via air pumped into a bladder within the treatment cuff from an air hose. The treatment cuff may have an air bladder configured to receive and hold air at a pressure effective to provide the desired level of compression. Air may be provided via any suitable air compressor known in the art. Such compression may be provided during all or part of a treatment sequences. For example, compression may be provided during heating periods but not cooling periods, during cooling periods but not heating periods, only during transition periods, during both heating periods and cooling periods, during only a subset of periods, or during all of the periods. In some embodiments, the level of compression may be varied. For example, the rate of heat transfer between the fluid and the patient's tissue proximate to the treatment pad may be varied by varying the level of compression effected by the treatment cuff. The compression level may be automatically adjusted to effect a desired rate of heat transfer. In some embodiments, pulse compression may be provided by alternating between a plurality of pressure levels, for example, to pulse massage the patient's tissue.

Without wishing to be constrained by theory, it is believed that a therapeutic effect may be achieved by synchronizing the frequency of a pressure pulse with patient's heart rate. Such pressure pulse may be provided via a pressure pulse in the fluid and/or compression of the treatment cuff. In some embodiments, a thermal contrast therapy device may be configured to receive an indication of a patient's heart rate, and to provide a pressure pulse having a frequency which is at least approximately synchronized with the patient's heart rate. Such synchronized pressure pulse may be provided during at least part of the treatment sequence. Synchronization may be achieved by measuring the patient's heart rate, for example, with a heart rate monitor auxiliary device, and adjusting the frequency of the valve sequencing accordingly. Without wishing to be constrained by theory, it is further believed that a therapeutic effect may also be achieved by providing a pressure pulse frequency selected to correspond to a desired heart rate. For example, it is believed that under certain conditions a pressure pulse frequency may effect a change in the patient's heart rate, in which the heart rate shifts towards and/or substantially synchronizes with the frequency of the pressure pulse. The range within which a patient's heart rate may be manipulated depends on physiological limitations of the patient, as well as the degree with which the particular patient may respond to the pressure pulse. In this way, a desired therapeutic effect may include inducing a desired heart rate during thermal contrast therapy.

Calibration

In some embodiments, a thermal contrast therapy device may be calibrated based on variations in the device and/or the preferences of one or more users of the device. A given treatment sequence may yield different effects due to differences between various devices (e.g., different manufacturers or model numbers), variations between devices (e.g., manufacturing differences between production runs), or set-up configurations (e.g., the length of the inflow and/or outflow lines between the device and treatment pad). These differences may be compensated for by calibrating treatment sequences for a particular device. A thermal contrast therapy device may be calibrated, for example, by measuring fluid temperature and/or flow rate, etc. with calibration equipment and adjusting calibration settings for the device. Calibration allows for customized thermal contrast therapy treatment sequences to be provided with consistency across a plurality of devices and/or for a plurality of users.

The artisan will appreciate that a given treatment sequence may yield different effects on different patients due to differences between patients, such as physiological attributes or personal preference. These differences may similarly be compensated for by providing a calibration adjustment corresponding to a particular patient. For example, a treatment sequence may be calibrated for a particular patient by providing a calibration adjustment to any one or more treatment sequence parameters. Providing a calibration adjustment may include, for example, shifting a set-point corresponding to a sequence parameter by a factor. As examples, one or more fluid temperature set-points in a treatment sequence may be shifted up or down; one or more set-points for a desired measure of heat transfer (i.e., rate of heat transfer or quantity of heat transfer) in a treatment sequence may be shifted up or down; or the number of periods in a treatment sequences and/or the duration of a treatment sequences may be shifted up or down. The calibration adjustment and/or factor may be based on a percentage, an absolute value, a formula, or the like. The calibration adjustment and/or factor may be derived empirically for an individual patient, and/or from data in a database associated with a thermal contrast therapy system, for example, data that relates to treatment sequences associated with other users. Such calibration adjustments may be applied to all treatment sequences, a subset of treatment sequences, or to a particular device, etc., and/or any of the foregoing as associated with a particular user.

II. Methods for Providing Thermal Contrast Therapy

Exemplary treatment methods for providing thermal contrast therapy will now be discussed. Those skilled in the art will appreciate that numerous other methods for providing thermal contrast therapy are within the spirit and scope of the present disclosure. Various thermal contrast therapy treatment methods may be performed using the devices and systems described herein. In some embodiments, various treatment methods for providing thermal contrast therapy may be performed using other devices and systems. The methods disclosed herein include computer-implemented methods of providing thermal contrast therapy.

Thermal contrast therapy may be provided by circulating fluid from a thermal contrast therapy device through a treatment pad applied to a patient, while providing a sequence of alternating cooling periods and heating periods. The alternating cooling periods and heating periods respectively deliver or remove heat from the treatment area. In some embodiments, a treatment sequence may include a plurality of transition periods, each occurring between alternating cooling periods and heating periods. During such transition periods, fluid having a first temperature corresponding to the first period displaces fluid having a second temperature corresponding to the second period. Thus, the rate of heat transfer between the patient's tissue and the fluid is transitioned from a first heat transfer rate which corresponds to the first period to a second heat transfer rate which corresponds to the second period.

Without wishing to be constrained by theory, it is believed that a patient's response to thermal contrast therapy may be enhanced by providing customized treatment sequences. Thus, in some embodiments, a customized thermal contrast therapy treatment sequence may be provided. A customized treatment sequence may be based upon, for example, any one or more of the following: characteristics of the patient sought to be treated, the area of the body sought to be treated, one or more symptoms or conditions sought to be treated, one or more desired therapeutic effects, and other considerations. In some embodiments, a customized treatment sequence may be based, at least in part, on a physiological parameter value exhibited by the patient.

A patient's response to thermal contrast therapy may depend on certain characteristics of the patient, including, for example, the patient's age, gender, body mass, fat content, physical fitness, energy level, and general state of health. Physiological characteristics as well as thermodynamic properties may also impact a patient's response to thermal contrast therapy. This includes a patient's ability to generate body heat, ability to repair the loss of heat, and ability to support the loss of heat without negatively impacting the body's vital processes, as well as the condition of the patient's nervous system at the time of treatment, and the extent to which the patient is accustomed to thermal contrast therapy. Other variables which may affect a patient's response to thermal contrast therapy include factors related to any particular chronic or acute condition or ailment affecting the patient, including a condition or ailment sought to be treated with thermal contrast therapy.

A patient's response to thermal contrast therapy may also depend on any one or more of a number of variables related to the conditions of the treatment sequence, including the rate of heat transfer between the fluid and the patient's tissue, the temperature of the heating periods and/or cooling periods, the pressure applied during treatment, the quantity and sequence of the heating periods and/or cooling periods, the various cycle times for each heating period and/or cooling period; the duration of, and rate of change during, transitions between heating periods and/or cooling periods, including whether a neutral temperature period is provided between heating periods and/or cooling periods, the duration of the thermal contrast therapy treatment sequence, the frequency with which thermal contrast therapy treatment is to be provided, the dimensions and configuration of the one or more treatment pads, the pulsation frequency of the fluid, and other variables.

Customized thermal contrast therapy treatment sequences may be provided based, at least in part, on any one or more of the variables disclosed herein, and/or other factors. Additionally, a series of treatment sequences making up a treatment program may be prescribed based on any one or more of the variables disclosed herein, and/or other factors. A treatment sequence may be customized, for example, in respect of the time duration for one or more periods, the number of periods in the treatment sequence, the fluid temperature corresponding to cooling periods and/or heating periods, the measure of heat transfer (i.e., quantity and/or rate) to be effected between the fluid and the patient's tissue during a treatment sequence and/or the respective heating periods and cooling periods thereof, or customization of any other operating variable of a thermal contrast therapy device. In some embodiments, a processor 144 may be configured to receive an indication from one or more temperature sensors and/or flow meters and to effect a desired measure of heat transfer between the fluid and the patient's tissue. Changes to the rate of heat transfer may be effected, for example, by automatically adjusting the temperature and/or flow rate of the fluid. The flow rate and/or fluid temperature may be changed according to any desired transition curve. In some embodiments, the processor 144 may be configured to receive an indication of one or more physiological parameter values and to cause the thermal contrast therapy device to perform a customized thermal contrast therapy treatment sequence based, at least in part, on the one or more physiological parameter values.

A customized treatment sequence may correspond to a treatment program having been prescribed to a user, or selected by a user of a thermal contrast therapy device. In some embodiments, a customized treatment sequence may be uploaded or stored in a database accessible by a thermal contrast therapy system or device. For example, a treatment provider or a user may select a treatment from a menu of one or more treatment options in a database associated with a thermal contrast therapy system configured to provide customized thermal contrast therapy treatment programs. Alternatively, a customized treatment sequence may be manually input by a treatment provider or a user.

Heat Transfer

A thermal contrast therapy treatment may be quantified based on measures of heat transfer, for example, the rate of heat transfer and/or the quantity of heat transfer effected during the respective heating periods and cooling periods of a treatment sequence. Without wishing to be constrained by theory, it is believed that various therapeutic effects of thermal contrast therapy may be enhanced by providing customized treatments which effect a specified measure of heat transfer (i.e., a rate of heat transfer and/or quantity of heat transfer). In some embodiments, a customized thermal contrast therapy treatment sequence includes effecting a specified measure of heat transfer between the fluid and the patient's tissue during one or more of the cooling periods and heating periods. The specified measure of heat transfer may be effected by automatically adjusting the flow rate and/or temperature of the fluid.

The rate of heat transfer between fluid in a treatment pad and a patient's tissue may be expressed as:

$$q = \frac{m}{t} c_p \Delta T \qquad (3)$$

where q is the mean heat transfer rate, $$\frac{m}{t}$$

is the mass flow rate per unit time, $c_p$ is the specific heat capacity of the fluid, and $\Delta T$ is the temperature gradient between the fluid and the patient's tissue. Those skilled in the art will appreciate that q represents an optimum heat transfer rate, and that in practice, while the vast majority of heat transfer during a during thermal contrast therapy treatment will be between the fluid and the patient's tissue proximate to the treatment pad, a portion of the heat transferred will be attributable to other considerations. For example, a portion of the heat will transfer to the cuff material and/or the surrounding atmosphere, etc. These considerations may be quantified empirically and/or by principles of thermodynamics known in the art, and the mean heat transfer rate during a given heating period or cooling period within a thermal contrast therapy treatment sequence may thus be expressed as:

$$q_{TCT} = k \frac{m}{t} c_p \Delta T \qquad (4)$$

where k is an efficiency constant which represents the proportion of heat transferred to the tissue proximate to the treatment pad.

The total heat transferred during a given heating period or cooling period may be obtained from:

$$Q_{TCT} = q_{TCT} \Delta t \qquad (5)$$

where $\Delta t$ is the duration of the applicable heating period or cooling period. Likewise, the heat transferred from the various heating periods and/or cooling periods may be summed to provide the total heat transferred during n periods, where n represents all or a subset of the periods comprising a thermal contrast therapy treatment sequence, as follows:

$$Q_{TCT} = \Sigma_{n=1}^{n} q_{TCT_1} \Delta t_1 + q_{TCT_2} \Delta t_2 + \ldots + q_{TCT_n} \Delta t_n \qquad (6)$$

In some embodiments, it may be advantageous to sum the heating periods and cooling periods separately, so as to ascertain the total heat transferred to the patient during heating periods and the total heat transferred from the patient during cooling periods.

In some embodiments it may be advantageous to model the heating and/or cooling of a patient's tissue during thermal contrast therapy. Such models may be used to evaluate treatment outcomes relative to model predictions, to perform research on various thermal contrast therapy treatment sequences and parameters thereof, and/or to suggest and evaluate new treatment strategies, etc.

The general factors to consider when quantifying heat transfer during thermal contrast therapy include heat transfer effected during the treatment, heat production due to metabolic processes, heat transfer due to blood perfusion, geometry of the thermal contrast therapy treatment area (e.g., as defined by the one or more treatment pads), the thermophysical properties of various types of body tissue, and thermoregulatory mechanisms.

Across a control volume, the principle of conservation of energy provides that the balance of thermal energy can be stated as:

$$q_{TCT} = q_{storage} + q_{loss} + q_{met} + W \tag{7}$$

where $q_{TCT}$ is the heat energy gained by the control volume, for example from a given heating period or cooling period during a thermal contrast therapy treatment, $q_{storage}$ is the heat energy stored within the control volume of tissue and fluid, $q_{loss}$ is the heat energy lost through the boundary of the control volume, $q_{met}$ is the heat energy produced by metabolic heating, and W is work performed on the control volume.

Heat is transferred by conduction, convection, evaporation, and radiation. The two primary mechanisms for heat transfer inside tissue during thermal contrast therapy are convection and conduction. Under most conditions for thermal contrast therapy, heat transfer by evaporation (or perspiration) and radiation, as well as the work, W, are negligible. The temperature gradient inside the tissue drives heat transfer through conduction, and blood perfusion drives heat transfer through convection.

According to Fourier's law, the conductive heat transfer between two layers is found by the relation:

$$q_{cond} = -kA\frac{dT}{dx} \tag{8}$$

where $q_{cond}$ is the conductive heat transfer per unit time, k is the thermal conductivity, A is the cross sectional area and dT/dx is the temperature gradient in the direction of heat transfer across a material of thickness x.

Those skilled in the art will appreciate that several approaches exist for modeling heat transfer from blood perfusion and that any one or more of such models may be used. Approaches for modeling heat transfer from blood perfusion include: the Pennes bioheat model; the Wulff continuum model; the Klinger continuum model; the Chen-Holmes (CH) continuum model; the Weinbaum, Jiji and Lemons (WJL) bioheat model; and the Simplified Weinbaum-Jiji model; the Zolfaghari and Maerefat simplified thermoregulatory bioheat model. These models generally employ a certain level of approximation, particularly because blood circulates in a variety of vessels ranging in lumen diameter from the approximately 2.5 cm, in the case of the aorta, to the approximately 6-10 µm, in the case of capillaries. More precise models based on computer algorithms or empirical research may also be utilized.

These aforementioned blood perfusion models generally rely on the basis of one of two main approaches: the continuum approach and the discrete vessel (vascular) approach. In the continuum approach, the thermal impact of all blood vessels are modeled with a single global parameter; and in the vascular approach, the impact of each vessel is modeled individually. The Pennes bioheat model is one of the most widely used approaches for modeling heat transfer from blood perfusion. The Pennes bioheat model assumes that the rate of heat transferred by the circulating blood at the capillary level equals the difference between the venous and arterial temperatures multiplied by the flow rate, as follows:

$$q_{blood} = \rho_b c_b w_b (T_a - T_v) \tag{9}$$

where $\rho_b$ is the density of the patient's blood, $c_b$ is the specific heat of the patient's blood, $w_b$ is the perfusion rate, $T_a$ is the arterial blood temperature, and $T_v$ is the venous blood temperature.

The heat energy stored in the control volume can be expressed as follows:

$$q_{storage} = \int_v \rho c(\bar{x}) \frac{dT(\bar{x}, t)}{dt} dv \tag{10}$$

where $\rho$ is the tissue density, c is the specific heat, and T is the tissue temperature.

The terms of equations (8), (9), and (10) may be substituted into equation (7) and integrated over the entire volume and surface area, to obtain the Pennes bioheat equation:

$$\rho c \frac{\partial T}{\partial t} = \nabla k \nabla T + \rho_b c_b w_b (T_a - T_v) + q_{met} \tag{11}$$

The Pennes bioheat equation can thus be used to analyze heat transfer in various body tissues under various thermal contrast therapy treatment sequences, including the customized treatment sequences disclosed herein.

The Pennes bioheat model assumes that the blood perfusion effect is homogenous and isotropic and that thermal equilibration occurs in the microcirculatory capillary bed due to the low blood flow velocity at the capillary level. Thus, the Pennes bioheat model assumes that blood enters capillaries at the temperature of arterial blood, $T_a$, where convective heat transfer occurs to bring the temperature to that of the surrounding tissue, such that the temperature at which the blood enters the venous circulation is that of the local tissue.

Pennes performed a series of studies to validate this model, which show reasonable agreement between the model and experimental data. Those skilled in the art will appreciate that while the Pennes bioheat model is often adequate, there are certain shortcomings in this model due to its inherent simplicity, and that other models, for example, those which utilize the discrete vessel (vascular) approach, may be more suitable in situations where enhanced precision is desired. For example, the Pennes bioheat model does not account for countercurrent heat transfer between adjacent vessels, or directionality effects due to the presence of larger blood vessels, or heat exchange with larger vessels in which complete thermal equilibrium may not be assumed. The CH continuum model and the WJL bioheat model, for example, address these issues. Accordingly, such other models may be used to analyze heat transfer as an alternative or in addition to the Pennes bioheat model.

Conditions particular to the patient intended to receive treatment and/or the particular area of the body sought to be treated, among other factors, may cause a given thermal contrast therapy treatment sequence to effect a different measure of heat transfer (i.e., a different rate of heat transfer and/or a different quantity of heat transfer). For example, various thermodynamic properties and other factors affecting heat transfer may be attributable to a patient's age, gender, body mass, body fat percentage, body mass index, metabolic rate, neural sensitivity, physical fitness, energy level, and general state of health. This includes the thermal conductivity, density, and heat capacity of a patient's body tissues and fluids, the surface thickness of various layers (e.g., dermis, epidermis, fat, muscle) of a patient's body tissue, factors related to a patient's blood perfusion, including blood pressure, blood flow rate, venous structure (e.g., capillary density, lumen diameter distribution, etc.), and a patient's metabolic rate. Likewise, given the various factors which may impact the measure of heat transfer effected during a given thermal contrast therapy treatment sequence, as between two patients and/or body parts sought to be treated, a different treatment may be required as between them in order to effect the same measure of heat transfer during the respective treatments. Furthermore, different thermal contrast therapy treatment sequences may be required for the same patient as, when, and if factors change which may impact the measure of heat transfer effected during a given treatment sequence.

Customized thermal contrast therapy treatment sequences may be configured to effect a specified measure of heat transfer during the treatment sequence and/or the one or more of the heating periods and/or cooling periods thereof. The specified measure of heat transfer (i.e., rate of heat transfer and/or quantity of heat transfer) may depend on any one or more of the factors affecting thermal contrast therapy treatments such as the factors disclosed herein, including: conditions particular to the patient intended to receive treatment, the particular area of the body sought to be treated, the particular symptom or condition sought to be treated, the particular desired therapeutic result, and/or other considerations.

Relationship Between Flow Rate and Heat Transfer

The rate of heat transfer between fluid in a treatment pad and a patient's tissue is directly proportional to the flow rate of the fluid. An increase in the flow rate increases the rate of heat transfer and a decrease in the flow rate decreases the rate of heat transfer. As heat transfer occurs between the fluid and the patient's body proximate to the treatment pad, the temperature of the fluid within the treatment pad will shift towards the temperature of the patient's tissue. The magnitude of this change in temperature is inversely proportional to the flow rate of the fluid. A relatively high flow rate will yield a relatively low change in temperature between the inflow and outflow ports of the treatment pad, and thus a relatively high driving force for heat transfer. Conversely, a relatively low flow rate will yield a relatively high change in temperature between the inflow and outflow ports of the treatment pad, and thus a relatively low driving force for heat transfer. Thus, the rate of heat transfer effected by the fluid depends on flow rate, and the rate of heat transfer effected during heating periods and/or cooling periods may be controlled by varying the flow rate of the fluid. Accordingly, at a constant fluid temperature entering the treatment pad, the rate of heat transfer may be increased by increasing the flow rate of the fluid, to the point where the change in temperature of the fluid between the inflow port and the outflow port of the treatment pad approaches zero. Conversely, the rate of heat transfer may be decreased by decreasing the flow rate of the fluid, to the point where the difference in temperature between the patient's body and the fluid approached zero.

The following example illustrates the relationship between the flow rate of fluid and the rate of heat transfer effected by the fluid. A cooling period was provided, via a thermal contrast therapy device having a treatment pad attached to a patient's lower leg. The temperature of the fluid (water) entering the treatment pad was maintained at about 40° F. At a flow rate of about 120 mL per minute, the fluid exiting the treatment pad was about 58° F. At a flow rate of about 240 mL per minute, the fluid exiting the treatment pad was about 53° F. Thus, using equation (3), the rate of heat transfer to the fluid was about 4.7 BTU per minute when the flow rate was 120 mL per minute (120 mL/min×1 sq. ft/28,316.8 mL×62.24 lb/sq. ft×1 BTU/lb-° F.×18° F.), and about 6.9 BTU per minute when the flow rate was 240 mL per minute (240 mL/min×1 sq. ft/28,316.8 mL×62.24 lb/sq. ft×1 BTU/lb-° F.×13° F.).

Thus, customized thermal contrast therapy treatment sequences may be provided which are based, at least in part, on providing a specified flow rate of the fluid. For example, a specified measure of heat transfer may be provided by varying the flow rate of the fluid. In some embodiments, a specified rate of heat transfer may be effected solely by varying the flow rate of the fluid. Alternatively, the specified measure of heat transfer may be attained by varying both the flow rate and the temperature of the fluid. For example, in some embodiments, the temperature of the fluid may be varied to attain a close approximation of a specified rate of heat transfer, and then the flow rate of the fluid may be varied to provide fine-tuning to more precisely control the rate of heat transfer.

In some embodiments, the artisan may derive advantages from utilizing changes in flow rate, in addition to or as an alternative to changes in fluid temperature, to effect a specified rate of heat transfer. For example, the heating and cooling loads on a thermal contrast therapy device may be reduced by using flow rate to effect a desired rate of heat transfer. This may yield more efficient, cost-effective devices, as well as enhanced ability to provide customized treatment sequences. Additionally, the rate of heat transfer may, in some embodiments, be more effectively controlled via the flow rate of the fluid than via the temperature of the fluid. This may be the case, for example, regarding embodiments having configurations such that the rate of heat transfer may be changed more rapidly and/or more precisely via a change in flow rate than via a change in temperature. In some embodiments a treatment pad having a small fluid volume may enhance the effect of flow rate on the rate of heat transfer, and consequently the range of control over the rate of heat transfer via flow rate. In certain embodiments where flow rate control facilitates more precise and/or more rapid control over the rate of heat transfer, customized thermal contrast therapy treatment sequences may be provided based, at least in part, on flow rate control which may not otherwise be feasible using only fluid temperature to control the rate of heat transfer. For example, a customized treatment sequences may include rapidly transitioning between heating periods and cooling periods, rapidly changing the rate of heat transfer, and/or more precisely controlling the rate of heat transfer.

During a thermal contrast therapy treatment sequence, the temperature gradient between the fluid entering the treatment pad and the patient's tissue proximate to the treatment pad may decrease as a result of the ensuing heat transfer. Thus, at a constant flow rate and constant temperature of fluid entering the treatment pad, the rate of heat transfer may decline over the course of a heating period or cooling period due to such decreasing temperature gradient. In some embodiments, a customized thermal contrast therapy treatment sequence may be provided in which the flow rate of the fluid is adjusted so as to maintain a desired rate of heat transfer notwithstanding changes in the temperature of the tissue proximate to the treatment pad. Such changes in flow rate may be effected, for example, over the course of a given heating period and/or cooling period, and/or from one period to the next over the course of the treatment sequence. For example, as the tissue proximate to the treatment pad changes temperature in response to heat transfer, the flow rate of the fluid may be increased so as to offset the decreasing rate of heat transfer that would otherwise result as tissue temperature proximate to the treatment pad shifts towards the temperature of the fluid in the treatment pad.

Additionally, temperature changes to a patient's tissue effected during one heating period or cooling period may impact the rate of heat transfer in a subsequent period. For example, alternating heating periods and cooling periods may provide a greater temperature gradient between the patient's tissue and the fluid in subsequent alternating periods. Thus, the driving force for heat transfer in a subsequent period may be enhanced, at least initially, due to the change in tissue temperature effected by the preceding period. Such enhanced temperature gradient may be desirable or undesirable, depending on the desired effects of the particular treatment sequence. In some embodiments, the flow rate of the fluid may be modified based, at least in part, on the temperature gradient between the patient's tissue and the fluid. This may include effecting a change in the flow rate of the fluid in consideration of an enhanced temperature gradient effected by one or more preceding periods. In some embodiments, a sequence of alternating cooling periods and heating periods may be configured to provide an enhanced temperature gradient in one or more subsequent periods in the sequence. In some embodiments, a neutral period may be provided between one or more of the alternating cooling periods and heating periods so as to provide a subdued temperature gradient in one or more subsequent periods in the sequence, for example, the period following the neutral period. In some embodiments, the flow rate of the fluid may be varied to effect a desired temperature gradient during at least a portion of a heating period and/or cooling period.

In some situations, thermal contrast therapy may be provided under circumstances where a patient may be particularly sensitive to hot and/or cold fluid temperatures. This may be the case, for example, with patients suffering from frostbite or hypothermia, elderly patients, patients with diabetes and related physiological complications (e.g., gangrene), patients with lymphedema or other disorders associated with vascular or lymphatic insufficiency (e.g., chronic venous insufficiency, venous stasis ulcers, post-mastectomy edema or chronic lymphedema), patients with peripheral vascular disease or other circulatory deficiency syndrome (e.g., arteriosclerosis, deep vein thrombosis, Buereger's disease, or thromboangiitis obliterans). Such sensitive patients may be unable to tolerate certain fluid temperatures without severe discomfort or injury to tissue. In these instances, it may be infeasible to use aggressive fluid temperatures to increase the rate of heat transfer without exceeding some discomfort or injury threshold. Instead, the rate of heat transfer may be enhanced by increasing the flow rate of the fluid, while maintaining a fluid temperature that is within the patient's pain tolerance and/or which will not cause injury to tissue. This approach may enable some sensitive patients to receive the benefit of enhanced cycles of vasoconstriction and vasodilation, enhanced improvements in blood flow, and/or other enhanced therapeutic effects, while maintaining a moderate fluid temperature that is suitable for sensitive patients.

Dynamically Controlled Treatment Sequences

A customized thermal contrast therapy treatment sequence may include dynamically controlling the sequence to effect a desired treatment and/or to attain a desired therapeutic effect. Any one or more variables of the treatment sequence may be dynamically controlled in order to provide a customized treatment sequence. In some embodiments, automatic adjustments to a thermal contrast therapy treatment sequence may include: changing a setting for the temperature and/or flow rate of the fluid; changing the duration of one or more of the cooling periods, heating periods, and/or transition periods; changing the number of cooling periods, heating periods, and/or transition periods; changing the rate of change of the temperature and/or flow rate of the fluid; and/or prescribing a sequence for one or more future thermal contrast therapy treatments.

Specified Measure of Heat Transfer

In some embodiments, the treatment sequence may be dynamically controlled to provide a desired measure of heat transfer (i.e., a rate of heat transfer and/or quantity of heat transfer) during one or more of the heating periods and/or cooling periods. The measure of heat transfer during one or more of the heating periods and/or cooling periods may be controlled, for example, using equations (4) and/or (5) and by adjusting the flow rate and/or temperature of the fluid, and/or the duration of the one or more periods. The rate of heat transfer, $q_{TCT}$, may be controlled for a given period, for example, using equation (4) and then adjusting the temperature gradient between the fluid and the patient's tissue proximate to the treatment pad, $\Delta T$. The quantity of heat transfer, $Q_{TCT}$, may be controlled, for example, using equation (5) and then adjusting the rate of heat transfer, $q_{TCT}$ and/or the duration of the period, $\Delta t$. The temperature gradient may be controlled by adjusting the temperature and/or the flow rate of the fluid. Dynamically controlled thermal contrast therapy treatment sequences may be provided which utilize any one or more equations for modeling blood perfusion (e.g., the Pennes bioheat model), and/or which take into account other factors which may impact heat transfer during thermal contrast therapy. Such factors include heat production due to metabolic processes, geometry of the thermal contrast therapy treatment area (e.g., as defined by the treatment pads), the thermophysical properties of various types of body tissue, and/or thermoregulatory mechanisms.

Figure 12A:
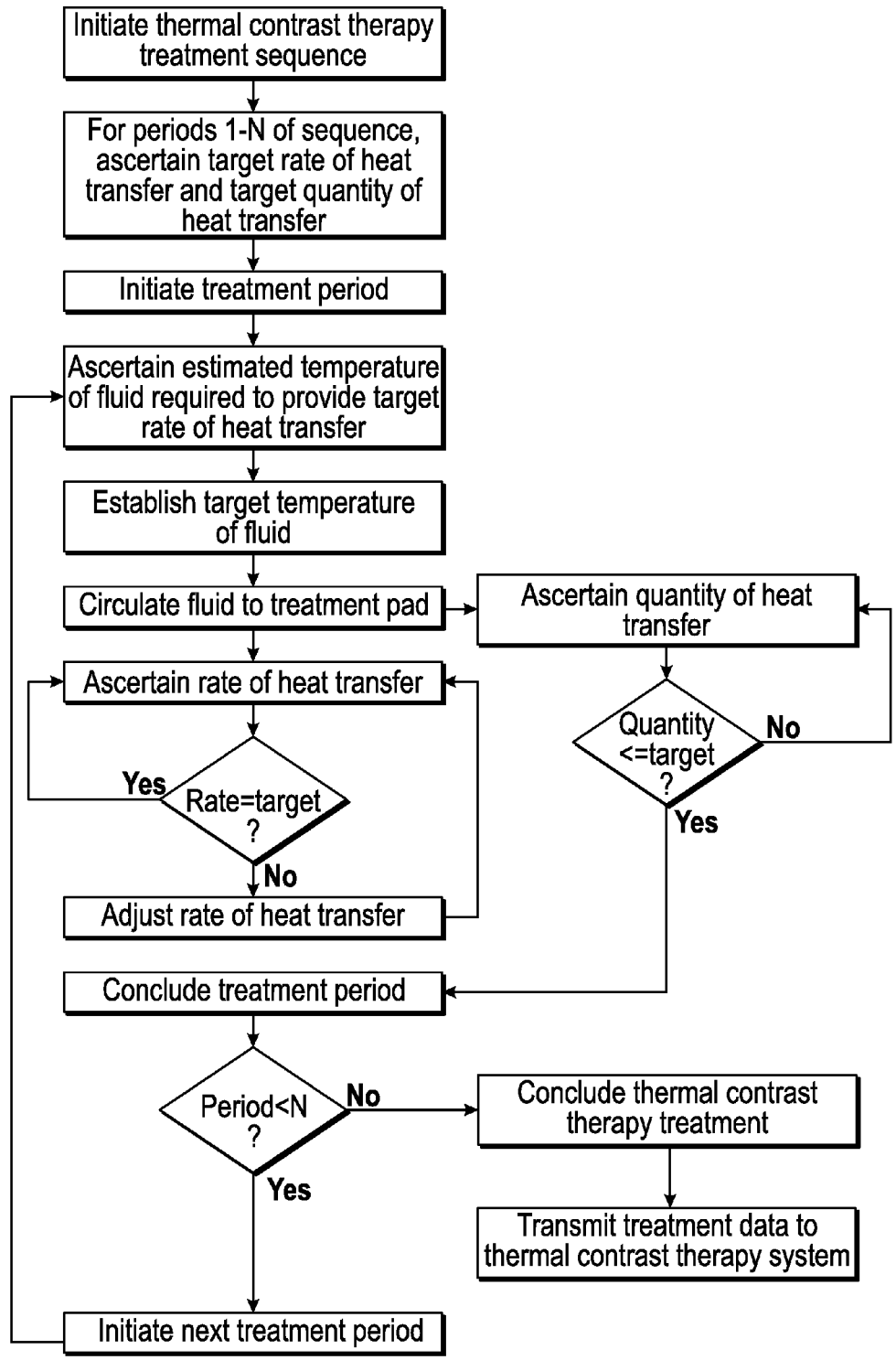
FIG. 12A shows a flow chart illustrative of an exemplary process for providing a desired measure of heat transfer during a thermal contrast therapy treatment sequence.

Referring to FIG. 12A, a flow chart is shown which illustrates an exemplary process for providing a specified measure of heat transfer during a thermal contrast therapy treatment sequence. The thermal contrast therapy device initiates the thermal contrast therapy treatment sequence. For each period of the treatment sequence, fluid is circulated to the treatment pad, the temperature of the fluid being approximately that which is required to provide the desired rate of heat transfer. Throughout the course of the treatment period, the rate of heat transfer is ascertained, and a determination is made as to whether the actual rate of heat transfer matches the target rate of heat transfer. The target may be a specific value or a range. If the rate of heat transfer does not match the target rate, then the rate of heat transfer is adjusted. The rate of heat transfer may be adjusted by changing the temperature and/or flow rate of the fluid.

Throughout the course of each treatment period within the sequence, the quantity of heat transfer effected is ascertained and a determination is made as to whether the actual quantity of heat transfer is less than or equal to the target quantity. In some embodiments, the period is concluded when the quantity of heat transfer reaches or exceeds the target quantity. Alternatively, the period may continue for a specified duration of time and conclude when the specified duration has elapsed.

When the treatment period has concluded, it is ascertained whether there are additional periods remaining in the sequence. If there are additional periods remaining, the device proceeds through such remaining periods until all of the periods have been administered. The treatment sequence concludes when all of the periods have been administered, at which point data associated with the treatment sequence may be transmitted to a thermal contrast therapy system.

Figure 12B:
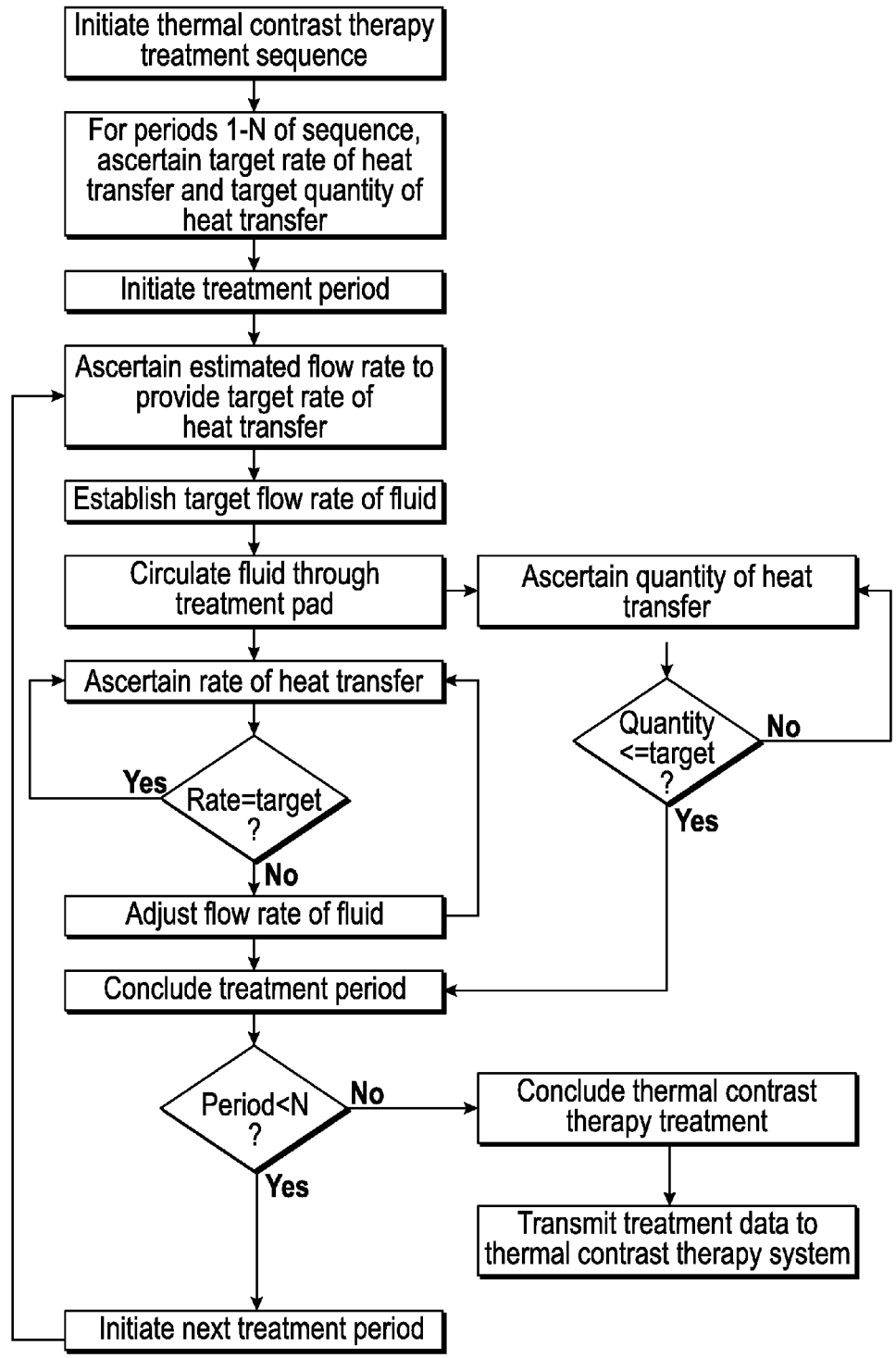
FIG. 12B shows a flow chart illustrative of an exemplary process for providing a desired measure of heat transfer during a thermal contrast therapy treatment sequence, utilizing flow rate to control the rate of heat transfer.

Referring to FIG. 12B, a flow chart is shown illustrating an exemplary process for providing a specified measure of heat transfer during a thermal contrast therapy treatment sequence, utilizing flow rate to modify the rate of heat transfer. The process described in FIG. 12B proceeds similar to that of FIG. 12A, with the additional step of controlling the rate of heat transfer by varying the flow rate of the fluid.

Physiological Parameter Values

In some embodiments, a customized thermal contrast therapy treatment sequence may be dynamically controlled to optimize one or more physiological parameter values. For example, one or more variables of a treatment sequence may be automatically adjusted when the patient exhibits a physiological parameter that corresponds to a predefined value. The physiological parameter values may be based on the patient's vital signs. A predefined value may include, for example, an increase from a previous value, a decrease from a previous value, a previous value, and/or a target value.

Physiological parameters which may be monitored and utilized to dynamically control a thermal contrast therapy treatment sequence include: body temperature (e.g. core temperature, local temperature, etc.), heart rate, blood pressure, blood flow, blood oxygen level, or other vital signs. Such vital signs may be monitored using any number of devices known in the art. For example, a thermal contrast therapy treatment sequences may be automatically adjusted so as to optimize the magnitude of an increase in blood circulation and/or blood oxygen content induced by cycles of vasoconstriction and vasodilation. In some embodiments, a thermal contrast therapy treatment sequence may include rapidly alternating cooling periods and heating periods and/ or rapid transition between alternating cooling periods and heating periods. Such a sequence may be effective to induce cycles of vasoconstriction and vasodilation. Cycles of vasoconstriction and vasodilation may be provided in a manner effective to cause an increase in blood circulation and/or blood oxygen content in a patient's tissue. In some embodiments, a thermal contrast therapy treatment sequence may be dynamically controlled to optimize vasoconstriction and vasodilation exhibited by the patient.

In some embodiments, a treatment sequence may be dynamically controlled based on a physiological parameter value exhibited by a patient during treatment. For example, based on a patient's vital signs, adjustments may be made during treatment to any one or more of: the fluid temperature provided during heating periods and/or cooling periods, the duration and/or number of heating periods and/or cooling periods, the quantity of heat transfer and/or rate of heat transfer during one or more of the heating periods and/or cooling periods. A treatment sequence may also be dynamically controlled based on a physiological parameter value exhibited by a patient prior to a treatment or during a previous treatment.

Figure 13A:
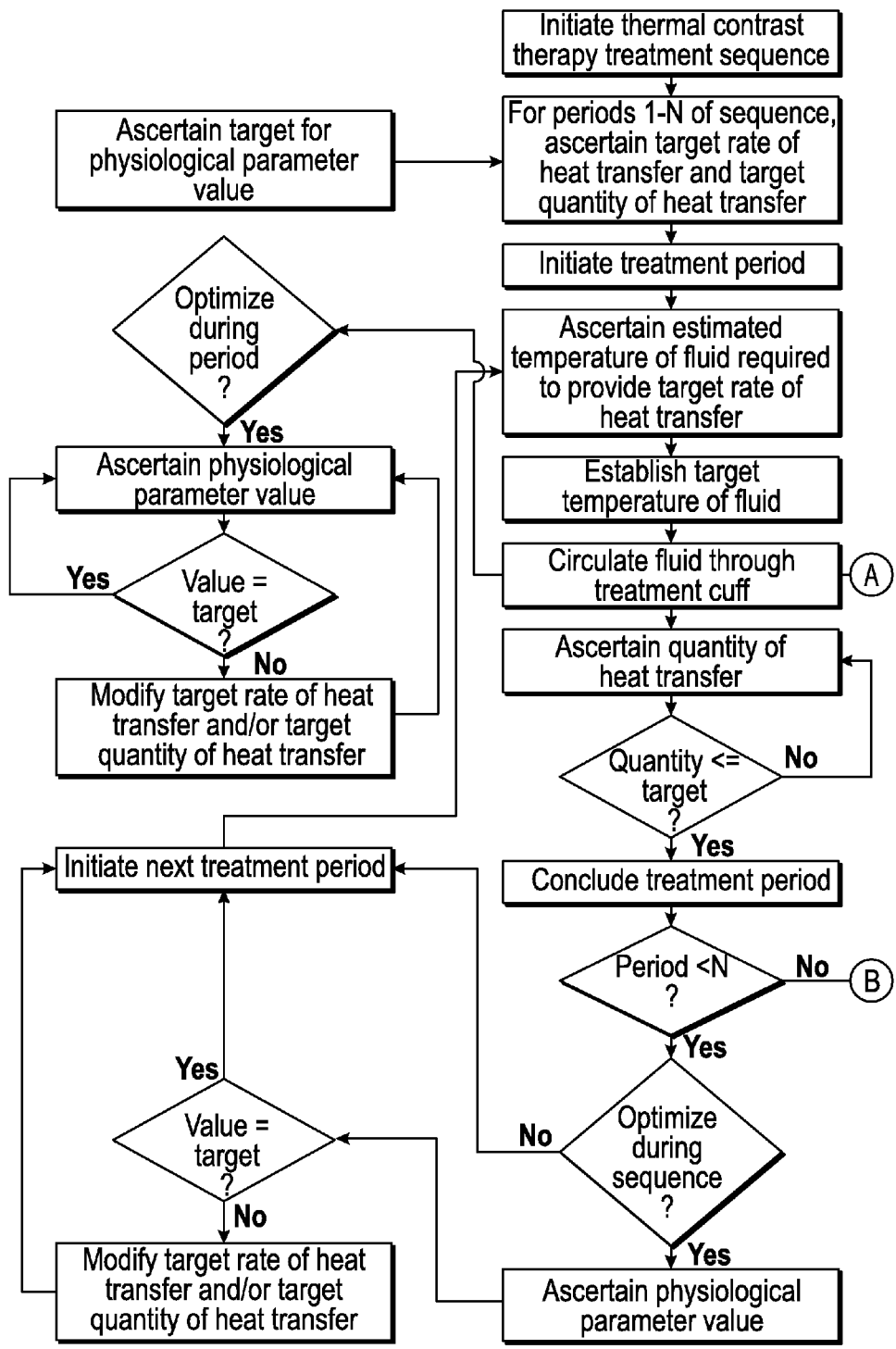
FIGS. 13A and 13B show a flow chart illustrative of an exemplary process for providing a customized thermal contrast therapy treatment sequence, dynamically controlled to optimize a physiological parameter value.
Figure 13B:
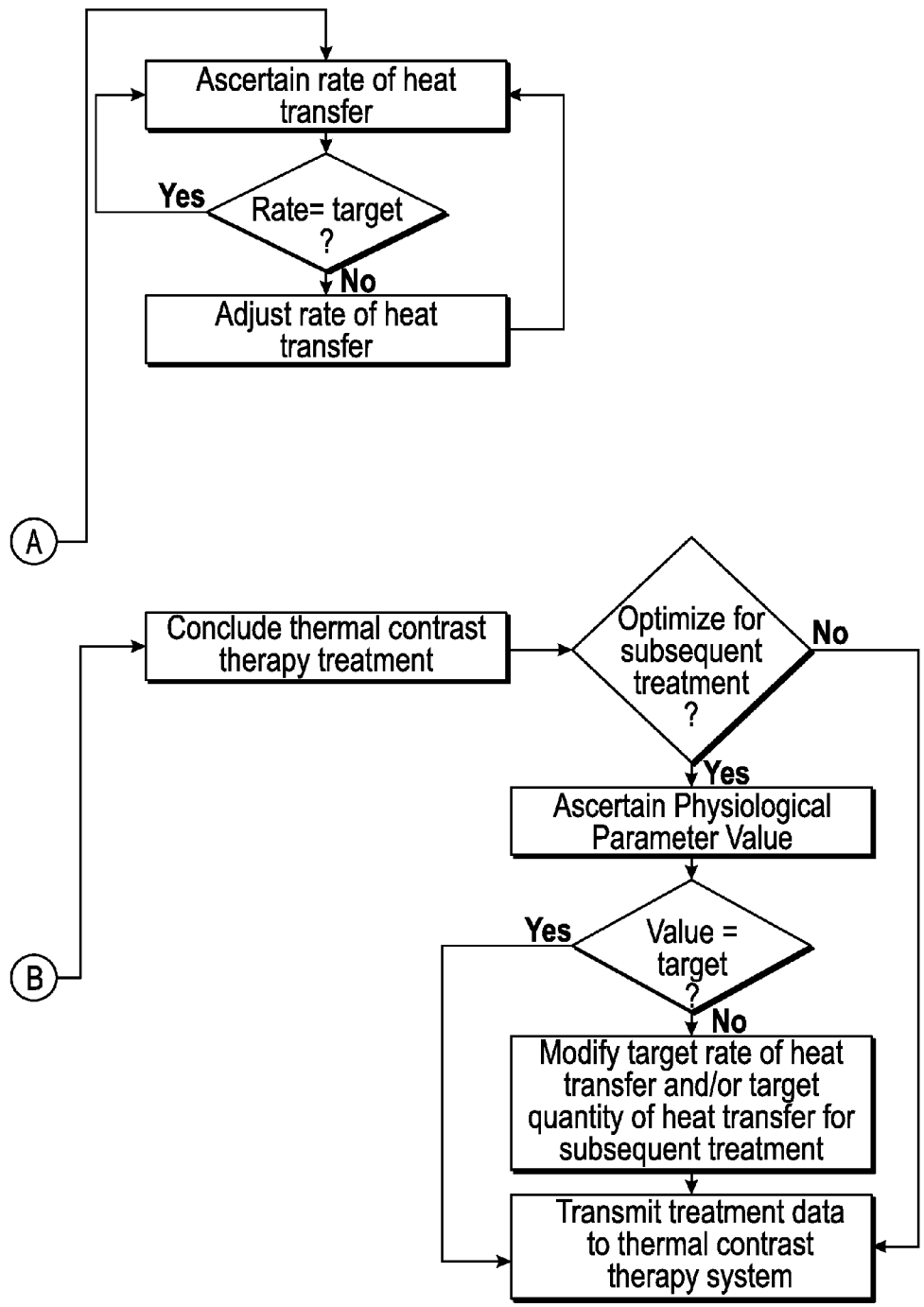

Referring to FIGS. 13A and 13B, a flow chart is shown illustrating an exemplary customized thermal contrast therapy treatment sequence, dynamically controlled to optimize a physiological parameter value. The treatment may be configured to optimize a physiological parameter value during any one or more of the periods, and/or for subsequent periods within the sequence, and/or for subsequent treatments within a treatment program. During a treatment period, it is ascertained whether the sequence calls for optimizing a physiological parameter value during the period. If so, the physiological parameter value is ascertained, and if the value is less than or greater than a predefined target value, one or more measures of heat transfer (i.e., the rate of heat transfer and/or the quantity of heat transfer) to be provided during the period are modified, e.g., to optimize the physiological parameter value. A predefined value corresponding to a physiological parameter may be one or more of: a target value, a minimum value, a maximum value, a range, an average, a standard deviation, an upper control limit, a lower control limit, a calculated value, a previous value, a change in the value, an increase from a previous value, a decrease from a previous value, a safety threshold, a deviation from any of the foregoing, an ascertained difference between a physiological parameter value and any of the foregoing and/or any other value desirable for dynamically controlling a thermal contrast therapy treatment sequence. A predefined value may, for example, be obtained from a treatment provider or derived from a database. Alternatively or in addition, a thermal contrast therapy device and/or system may provide one or more preconfigured predefined values. Such preconfigured values may be modified by a user and/or a treatment provider.

When a treatment period has concluded, it is ascertained whether the sequence calls for optimizing a physiological parameter value for subsequent periods within the sequence. If so, the physiological parameter value(s) exhibited during the concluded period and/or other previously concluded periods are ascertained, and if the value(s) are less than or greater than a predefined target value, one or more measures of heat transfer to be provided during one or more subsequent periods in the sequence are modified, e.g., to optimize the physiological parameter value.

When a treatment sequence has concluded, it is ascertained whether the sequence calls for optimizing a physiological parameter value for subsequent treatment sequences within a treatment program. If so, the physiological parameter value(s) exhibited during the concluded sequence and/or other previously concluded sequences are ascertained, and if the value(s) are less than or greater than a predefined target value, one or more measures of heat transfer to be provided during one or more subsequent treatment sequences are modified, e.g., to optimize the physiological parameter value. At the conclusion of the treatment sequence, data associated with the sequence may be transmitted to a thermal contrast therapy system, e.g., to be stored in a database for future use.

Automatic Adjustments to a Treatment Sequence

Dynamically controlled treatment sequences may include one or more automatic adjustments to a treatment sequence.

Automatic adjustments may occur at any desired time during the course of the sequence. A sequence may be automatically adjusted during the course of one or more cooling periods or heating periods within the sequence, for example, based on a physiological parameter value exhibited during the same period. Such automatic adjustment may be provided, for example, to attain a desired effect from a particular period within the sequence during which the one or more adjustments occur. Additionally, or in the alternative, one or more subsequent periods within a sequence may be automatically adjusted based on the effects of one or more prior periods, for example, based on a physiological parameter value exhibited during a previous cooling period or heating period. Automatic adjustments in a subsequent period or periods may be provided, for example, to attain a desired effect from such subsequent period or periods. Automatic adjustments to a treatment sequence may be effected at any time during the course of treatment, for example, to attain a desired effect from the particular treatment. Automation adjustments may also be effected over the course of several treatments, for example, to attain a desired effect from a series of treatments.

In some instances, the particular settings which might be expected to produce a desired therapeutic effect may not be known, or may be uncertain. Given this, in some embodiments a thermal contrast therapy treatment sequence, and/or series of treatments within a treatment program may be configured to administer varying heating periods and/or cooling periods, treatment sequences, and/or overall treatment programs, while monitoring physiological parameter values, other therapeutic effects, and/or other factors related to the treatment, and then to cause the treatment sequence(s), period(s), or program(s) to be dynamically modified, e.g., to optimize one or more physiological parameter values or other desired therapeutic effects. Such automatic adjustments may be made to heating periods and/or cooling periods within a treatment sequence, to one or more treatment sequences making up a treatment program, and/or to an overall treatment program.

In some embodiments, a dynamically controlled treatment sequence may be provided, in which the dynamic control is configured to provide conditions intended to correspond to conditions of a prior treatment sequence. This may include reproducing or replicating conditions of a prior treatment, or adjusting one or more variables which may affect the treatment, a physiological parameter value, and/or a therapeutic effect of the treatment, for example, based at least in part on conditions corresponding to one or more prior treatments.

In some embodiments, a thermal contrast therapy treatment sequence may be dynamically controlled or automatically adjusted based on a patient's comfort level. For example the sequence may be adjusted based on input as to whether the treatment feels painful or uncomfortable, too hot or too cold, or just right. Such patient input may be derived from one or more physiological parameter values, such as vital signs, or input may be provided directly by patient, for example via a user interface.

Those skilled in the art will appreciate that both feed-back and feed-forward control loops may be utilized with the dynamically controlled treatment sequences disclosed herein.

Exemplary Customized Thermal Contrast Therapy Treatments

Exemplary customized thermal contrast therapy treatments will now be discussed. Those skilled in the art will appreciate that numerous other treatment sequences are within the spirit and scope of the present disclosure. Customized thermal contrast therapy treatment sequences may be provided based on any one or more variables, including the variables disclosed herein. Customized treatment sequences may be provided based on the preference of the practitioner or therapist, or the patient receiving treatment. Treatment sequences may be developed on the basis of research and/or results attained by users associated with a thermal contrast therapy system.

Treatment sequences may be customized based on the area of the body sought to be treated, the particular symptom or condition sought to be treated, or the particular desired therapeutic result(s). As examples, customized treatment sequences may be provided for any area of the body, such as the hand, wrist, forearm, elbow, upper arm, shoulder, foot, ankle, calf, shin, knee, thigh, hip, pelvic region, abdomen, lumbar, mid-back, upper-back, neck, and cranium.

Customized treatment sequences may also be provided for any one or more conditions or symptoms sought to be treated, such as: edema or swelling, fever, toxins, spasms, constipation, immune function inflammation, sprains, strains, general pain, neuropathy, arthritis, carpel tunnel, non-healing wounds, gangrene, migraine headaches, whiplash associated disorders, hair loss, muscular spasms, sinus pressure, disorders associated with lack of proper blood flow, bed sores, and respiratory ailments, among other things. Customized treatments may also be provided for patients with hypothermia or frostbite, for example, to enhance circulation in affected tissue.

As further examples, customized treatments may be provided to encourage healing of bones and tissue, and to rehabilitate injuries to bone, muscle, ligaments, tendons, and skin. Customized treatments may also be provided after an acute injury or surgery, for example, to reduce pain and swelling and promote healing. Customized treatments may be provided to athletes after or between training sessions to speed recovery or reduce delayed onset muscle soreness, by helping to flush lactic acid from sore muscles. Customized treatments may also be provided to relax joint tissue, such as ligaments and tendons, to increase range of motion. Customized treatments may also be provided for patients with spinal cord or nerve damage, for example, to enhance blood flow to the injured nerve tissue, or prevent or mitigate disputation of the tenuous blood supply.

Customized treatments may also be provided as a therapy for diabetes and related physiological complications, for example, gangrene, or for lymphedema or other disorders associated with vascular or lymphatic insufficiency, for example, chronic venous insufficiency, venous stasis ulcers, post-mastectomy edema or chronic lymphedema, and for peripheral vascular disease or other circulatory deficiency syndrome, for example, arteriosclerosis, deep vein thrombosis, Buereger's disease, or thromboangiitis obliterans, or to positively influence the immune system.

Treatments may also be customized based on one or more desired therapeutic effects sought to be attained. As examples, therapeutic effects sought to be attained from thermal contrast therapy may include increased blood flow, increased blood oxygen levels, reduced inflammation, pain reduction, accelerated healing, increased medication effectiveness and focus, improved distal perfusion, improved arterial inflow, improved venous return flow, toxin removal, reduction of inflammatory kinins, and assistance to a chronically decompensated heart by complementing the heart cycle.

Without wishing to be constrained by theory, it is believed that thermal contrast therapy performed on one area of the body may cause a sympathetic response in a different area of the body. For example, treatment performed on one limb (e.g., an arm or leg) may effect a therapeutic response in the opposite limb. Accordingly, in some embodiments customized treatments may be provided to effect a sympathetic response. The sympathetic response may include activation of the sympathetic nervous system, associated sensations associated with therapy in a limb opposite to the limb receiving direct treatment, increased blood flow, enhanced tissue healing and rehabilitation, and other desired therapeutic effects. In some embodiments, thermal contrast therapy may be provided so as to effect a sympathetic response in a different area of the body in addition to or as an alternative to providing therapy directly to such area. This may be effective to enhance the therapeutic effects of thermal contrast therapy in patients and/or particular areas of the body which may be particularly sensitive and therefore unable to tolerate certain fluid temperatures without severe discomfort or injury to tissue.

The total treatment time for a thermal contrast therapy sequence may range from a few minutes to several hours in duration, for example, from 10 minutes to 2.5 hours, or from 20 minutes to 75 minutes. As further examples, the total treatment time may be between about any two of the following durations: 5 minutes, 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, 105 minutes, 110 minutes, 115 minutes, 120 minutes, 125 minutes, 130 minutes, 135 minutes, 140 minutes, 145 minutes, 150 minutes, or any intermediate time period, or longer.

A treatment sequence may begin with either a heating period or a cooling period. Different therapeutic effects may be attained depending on whether therapy begins with a heating period or a cooling period. The duration of a heating period or a cooling period may range from a few seconds to several minutes. As examples, the duration of heating periods and/or cooling periods may range from about 5 seconds to 60 seconds, from about 1 minute to 5 minutes, from about 5 minutes to 20 minutes, or longer. A period may last, for example, between about any two of the following durations: 5 seconds, 10 seconds, 15 seconds, 20 seconds, 25 seconds, 30 seconds, 35 seconds, 40 seconds, 45 seconds, 50 seconds, 55 seconds, 60 seconds, 65 seconds, 70 seconds, 75 seconds, 80 seconds, 85 seconds, 90 seconds, 95 seconds, 100 seconds, 105 seconds, 110 seconds, 115 seconds, 120 seconds, 125 seconds, 130 seconds, 135 seconds, 140 seconds, 145 seconds, 150 seconds, 155 seconds, 160 seconds, 165 seconds, 170 seconds, 175 seconds, 180 seconds, 185 seconds, 190 seconds, 195 seconds, 200 seconds, 205 seconds, 210 seconds, 215 seconds, 220 seconds, 225 seconds, 230 seconds, 235 seconds, 240 seconds, 250 seconds, 260 seconds, 270 seconds, 280 seconds, 290 seconds, 300 seconds, 10 minutes, 15 minutes, 20 minutes, 25 minutes, 30 minutes, or any intermediate time period, or longer. Alternatively, in some embodiments, a cooling or heating period may be provided which comprises continuous application of hot or cold.

Transition time may be limited by the time required for fluid corresponding to a first period to be displaced by fluid corresponding to a second period, and/or the time required to overcome the thermal mass of various components of the thermal contrast therapy device, fluid lines, and treatment pad which may be in thermal communication with the fluid, particularly those components which are in thermal communication with fluid from the heating block and with fluid from the cooling block. The thermal contrast therapy devices disclosed herein may facilitate rapid transitions between alternating heating periods and cooling periods, for example, by minimizing the time required to displace fluid and/or by minimizing the thermal mass in thermal communication with fluid from the heating block and with fluid from the cooling block.

Transition time may also depend on a desired therapeutic effect. In some instances a rapid transition may be desired, whereas in other instances a more gradual transition may be desired. For example, when treating a physically fit patient for muscle spasms, a rapid transition may be desired, whereas an elderly person afflicted by poor circulation may be unable to withstand a high level of contrasting heat transfer, and as such, a mild transition may be desired. In some embodiments, a rapid transition may enhance the pumping effect of vasoconstriction and vasodilation. Transition times between alternating heating periods and cooling periods may range from a few seconds to several minutes, for example, from about 5 seconds to 30 minutes, from about 5 seconds to 90 seconds, from about 15 seconds to 300 seconds, from about 30 seconds to 90 seconds, from about 60 seconds to 180 seconds, from about 5 minutes to 10 minutes, or from about 10 minutes to 30 minutes. Transition times may be, for example, less than about 5 seconds, 10 seconds, 15 seconds, 20 seconds, 25 seconds, 30 seconds, 35 seconds, 40 seconds, 45 seconds, 50 seconds, 55 seconds, 60 seconds, 65 seconds, 70 seconds, 75 seconds, 80 seconds, 85 seconds, 90 seconds, 120 seconds, 180 seconds, 240 seconds, 300 seconds, 10 minutes, 15 minutes, 20 minutes, 25 minutes, 30 minutes, or any intermediate time period, or longer period.

In some embodiments, a neutral period comprising a neutral temperature and/or rate of heat transfer may be provided between some or all of the heating periods and cooling periods. The neutral period may be provided as part of the transition between heating periods and cooling periods, or the neutral period may be treated as its own distinct period. The duration of a neutral period may range from a few seconds to several minutes. As examples, the duration of neutral periods may range from about 5 seconds to 60 seconds, from about 1 minute to 5 minutes, from about 5 minutes to 20 minutes, or longer. A neutral period may last, for example, between about any two of the following durations: 5 seconds, 10 seconds, 15 seconds, 20 seconds, 25 seconds, 30 seconds, 35 seconds, 40 seconds, 45 seconds, 50 seconds, 55 seconds, 60 seconds, 65 seconds, 70 seconds, 75 seconds, 80 seconds, 85 seconds, 90 seconds, 95 seconds, 100 seconds, 105 seconds, 110 seconds, 115 seconds, 120 seconds, 125 seconds, 130 seconds, 135 seconds, 140 seconds, 145 seconds, 150 seconds, 155 seconds, 160 seconds, 165 seconds, 170 seconds, 175 seconds, 180 seconds, 185 seconds, 190 seconds, 195 seconds, 200 seconds, 205 seconds, 210 seconds, 215 seconds, 220 seconds, 225 seconds, 230 seconds, 235 seconds, 240 seconds, 5 minutes, 10 minutes, 15 minutes, 20 minutes, 25 minutes, 30 minutes, or any intermediate time period, or longer.

In some embodiments, a thermal contrast therapy treatment sequence may be provided in which the fluid temperature and/or rate of heat transfer exhibits a continuous cyclical change at least for a portion of the treatment sequence. For example, the sequence may continuously cycle between alternating heating periods and cooling periods. When performing such a sequence, a thermal contrast therapy device may be configured to effect a first specified temperature and/or rate of heat transfer, and then transition to a second specified temperature and/or rate of heat transfer upon having attained the first specified temperature and/or rate of heat transfer. Such a sequence may continuously cycle between any number of specified temperatures and/or rates of heat transfer. When a treatment sequence or a portion thereof exhibits a continuous cyclical change between specified temperatures and/or rates of heat transfer, the continuous cyclical change may be characterized as having heating periods and/or cooling periods with a duration approaching zero seconds (e.g., less than 15 seconds, less than 10 seconds, less than 5 seconds, less than 1 second, or zero seconds), and transition periods consuming the balance of the duration of time attributed to the continuous cyclical change.

Fluid temperatures during heating periods may range from about 85° F. to 130° F., or from about 100° F. to 110° F. The fluid temperature during a heating period may be, for example, greater than about 85° F., 90° F., 95° F., 100° F., 105° F., 110° F., 115° F., 120° F., 125° F., 130° F., or any intermediate temperature, cooler temperature, or warmer temperature. Other temperatures for heating periods will also be apparent to the skilled artisan.

During cooling periods, fluid temperatures may range from about 30° F. to 70° F., or from about 40° F. to 50° F. As further examples, cold fluid temperatures may be less than about 30° F., 35° F., 40° F., 45° F., 50° F., 55° F., 60° F., 65° F., 70° F., or any intermediate temperature, cooler temperature, or warmer temperature. Other temperatures for cooling periods will also be apparent to the skilled artisan.

Transition periods may provide fluid of any temperature which is between the temperature corresponding to the period preceding the transition period and the temperature which corresponds to the period following the transition period. For example, fluid temperatures during a transition period may be between about any two of the following temperatures: 30° F., 35° F., 40° F., 45° F., 50° F., 55° F., 60° F., 65° F., 70° F., 75° F., 80° F., 85° F., 90° F., 95° F., 100° F., 105° F., 110° F., 115° F., 120° F., 125° F., 130° F., or any intermediate temperature, cooler temperature, or warmer temperature. Other temperatures for transitions will also be apparent to the skilled artisan.

Transition periods may be configured to provide a customized transition curve. The transition curve between two periods may be rapid or gradual, may comprise various rates of change during the transition, and may include a neutral period comprising providing for a specified period of time, a desired rate of heat transfer, and/or a desired temperature for the fluid, which is between that of the period preceding the neutral period and the period following the neutral period.

Flow rates of fluids may range from about 10 mL/min to 1000 mL/min. For example, flow rates may be at least about 10 mL/min, 50 mL/min, 100 mL/min, 150 mL/min, 200 mL/min, 250 mL/min, 300 mL/min, 350 mL/min, 400 mL/min, 450 mL/min, 500 mL/min, 550 mL/min, 600 mL/min, 650 mL/min, 700 mL/min, 750 mL/min, 800 mL/min, 850 mL/min, 900 mL/min, 950 mL/min, 1000 mL/min, or any intermediate flow rate, higher flow rate, or lower flow rate. Flow rates may be increased where a high rate of heat transfer is desired, or decreased where a low rate of heat transfer is desired. In some embodiments, flow rate may be reduced to zero to provide a gradually declining rate of heat transfer. In some embodiments, flow rate may be increased to a point where the temperature difference between the fluid entering and exiting a treatment pad approaches a target value, for example, a minimum value, or approximately zero.

Rates of heat transfer may range from about 0.5 BTU/min to 25 BTU/min. For example, the rate of heat transfer during a given period may be between about any two of the following rates: 0.5 BTU/min, 1 BTU/min, 1.5 BTU/min, 2 BTU/min, 2.5 BTU/min, 3 BTU/min, 3.5 BTU/min, 4 BTU/min, 4.5 BTU/min, 5 BTU/min, 5.5 BTU/min, 6 BTU/min, 6.5 BTU/min, 7 BTU/min, 7.5 BTU/min, 8 BTU/min, 8.5 BTU/min, 9 BTU/min, 9.5 BTU/min, 10 BTU/min, 10.5 BTU/min, 11 BTU/min, 11.5 BTU/min, 12 BTU/min, 12.5 BTU/min, 13 BTU/min, 13.5 BTU/min, 14 BTU/min, 14.5 BTU/min, 15 BTU/min, 15.5 BTU/min, 16 BTU/min, 16.5 BTU/min, 17 BTU/min, 17.5 BTU/min, 18 BTU/min, 18.5 BTU/min, 19 BTU/min, 19.5 BTU/min, 20 BTU/min, 20.5 BTU/min, 21 BTU/min, 21.5 BTU/min, 22 BTU/min, 22.5 BTU/min, 23 BTU/min, 23.5 BTU/min, 24 BTU/min, 24.5 BTU/min, 25 BTU/min, 30 BTU/min 40 BTU/min 50 BTU/min 100 BTU/min 150 BTU/min, or any intermediate rate, greater rate, or lesser rate. Other heat transfer rates will also be apparent to the skilled artisan.

Referring to FIGS. 14A-1 and 14A-2 through 14G-1 and 14G-2, a selection of exemplary thermal contrast therapy treatment sequences are shown. As shown in FIGS. 14A-1 and 14A-2, 14B-1 and 14B-2, 14C-1 and 14C-2, and 14D-1 and 14D-2, a treatment sequence may be configured to provide a desired fluid temperature during the various periods of the treatment sequence, and as shown in FIGS. 14E-1 and 14E-2, 14F-1 and 14F-2, and 14G-1 and 14G-2, a treatment sequence may be configured to provide a desired measure of heat transfer during the various periods of the treatment sequence. Additionally, treatment sequences may be configured to effect both a desired fluid temperature and a desired measure of heat transfer. Treatment sequences configured to effect a desired measure of heat transfer may provide for a desired rate of heat transfer and/or a desired quantity of heat transfer. Where a treatment sequence provides for a desired quantity of heat transfer, the duration of the treatment periods within the sequence may depend on the rate of heat transfer. In addition or as an alternative, treatment sequences configured to effect a desired rate of heat transfer may provide for treatment periods having a predefined time duration, where the desired quantity of heat transfer depends on such time duration.

FIGS. 14A-1 and 14A-2 show an exemplary customized thermal contrast therapy treatment sequence configured to provide a desired fluid temperature during the various periods of the treatment sequence, for a first treatment of an athletic injury to a knee or elbow in a healthy/strong patient within the first 24 hours after the injury, to reduce inflammation. The treatment may be suitable, as an example, for an athlete to treat a knee injury that has occurred within 24 hours prior to treatment. The sequence shown in FIGS. 14A-1 and 14A-2 may be the first treatment of this injury, and as such the temperature contrast starts mildly and builds up through the treatment by decreasing the temperature of the fluid during cooling periods while maintaining constant temperature during the heating periods. Mid-way through the sequence, the treatment region is allowed to calm with lesser contrast (by gradually increasing the temperature during the cooling periods), so as to reduce a sudden shock when the treatment it stopped.

Figures 1, 14B:
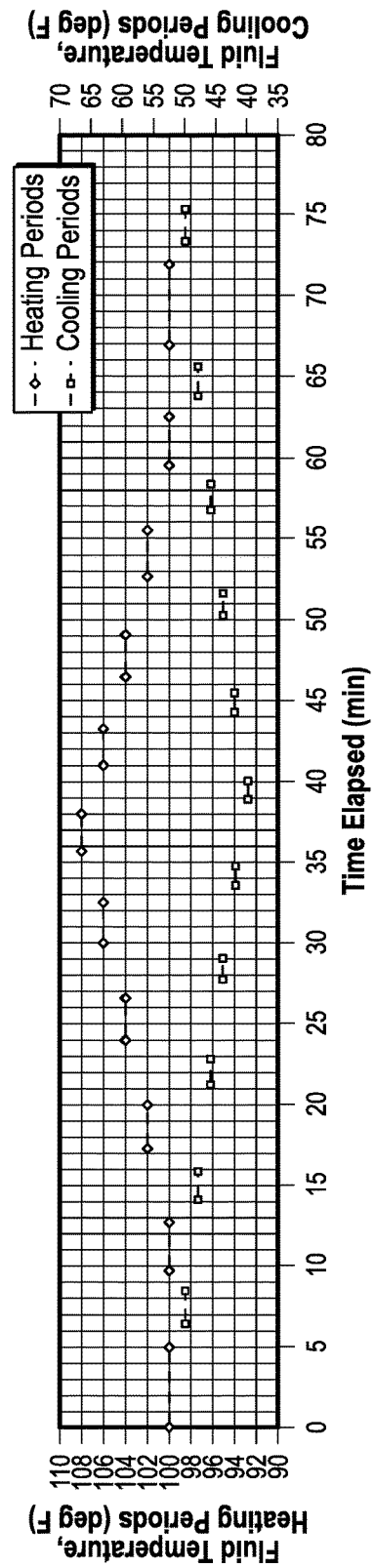

FIGS. 14B-1 and 14B-2 show an additional exemplary treatment sequence configured to provide a desired fluid temperature during the various periods of the treatment sequence. This treatment sequence may be suitable, as an example, for subsequent treatment of an athletic injury to a knee or elbow in a healthy/strong patient after the first 24 hours following the injury, to reduce inflammation and increase blood flow. For example, the sequence shown in FIGS. 14B-1 and 14B-2 may be provided as a subsequent treatment after previously having provided the sequence shown in FIGS. 14A-1 and 14A-2. Here, vasodilation and vasoconstriction may be enhanced by providing a gradually increasing fluid temperature during the heating periods and a gradually declining fluid temperature during cooling periods. Mid-way through the sequence, the region is allowed to calm with lesser contrast (by gradually increasing the temperature during the cooling periods and decreasing the temperature during heating periods), so as to reduce a sudden shock when the treatment it stopped.

Figures 1, 14C:
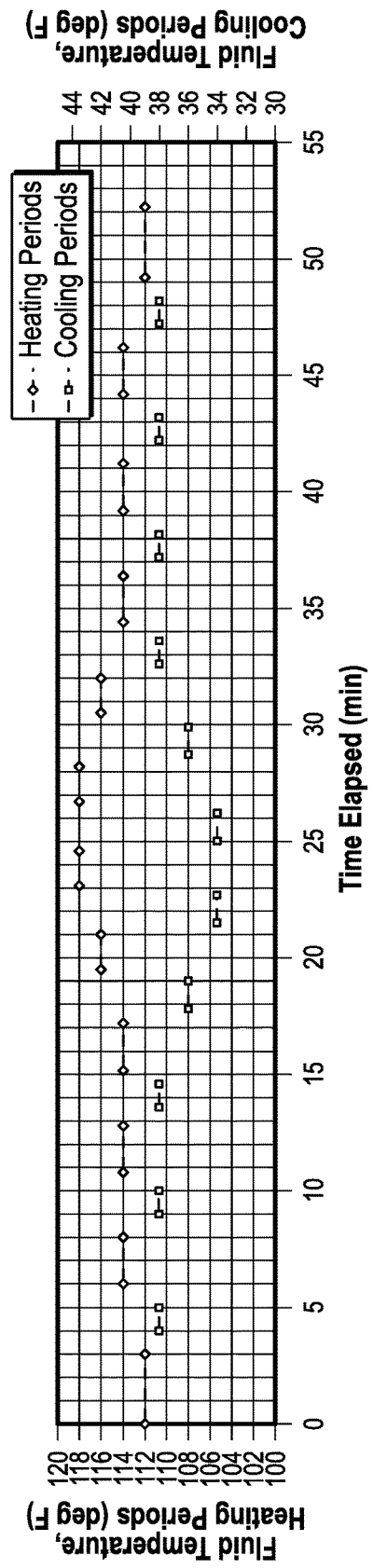

FIGS. 14C-1 and 14C-2 show yet an additional exemplary treatment sequence configured to provide a desired fluid temperature during the various periods of the treatment sequence, which may be suitable for ongoing treatment during rehabilitation of an athletic injury to a knee or elbow. This treatment sequence may be suitable for a strong/healthy patient after the first 48 hours following the injury, to reduce inflammation, increase blood flow, and for pain management. For example, the sequence shown in FIGS. 14C-1 and 14C-2 may be provided as a subsequent treatment after previously having provided the sequence in FIGS. 14B-1 and 14B-2. Here, rapid consecutive alternating heating periods and cooling periods are provided, as indicated by the short transition times, and temperature differences between heating periods and cooling periods are large, with treatment temperatures intended to be at the threshold of a patient's tolerance so as to attain the maximum tolerable effect.

Figures 1, 14D:
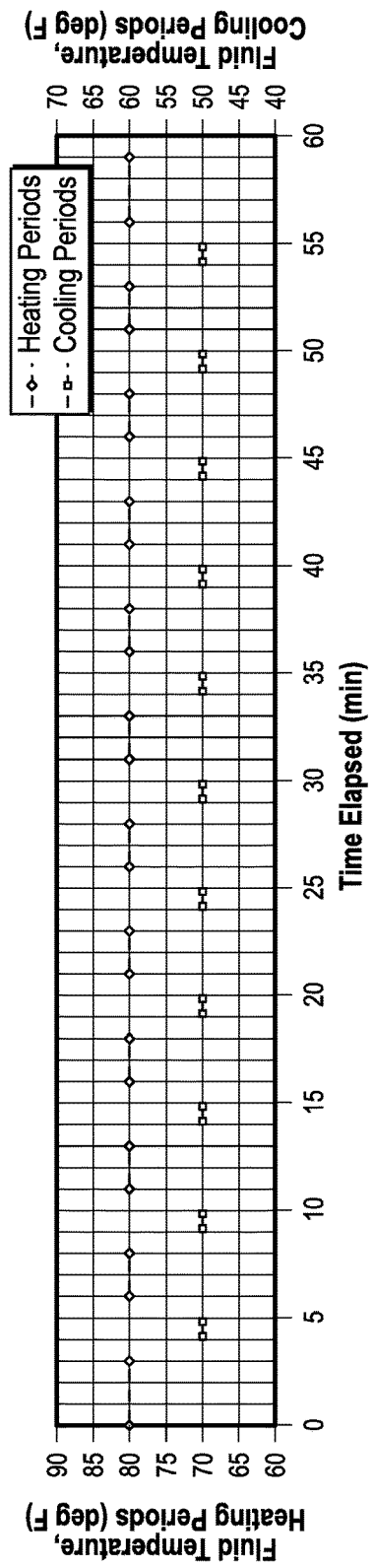

FIGS. 14D-1 and 14D-2 show an exemplary thermal contrast therapy treatment sequence configured to provide a desired fluid temperature during the various periods of the treatment sequence, which may be suitable for treatment of gangrene below the knee. This treatment sequence may be suitable for an elderly patient in relatively poor physical condition, with a desired therapeutic effect of increasing blood flow and revitalizing tissue. Here, relaxed transitions and more modest temperature variations are used, given the patient's physical condition and sensitive nature of the tissue being treated.

Figures 1, 14E:
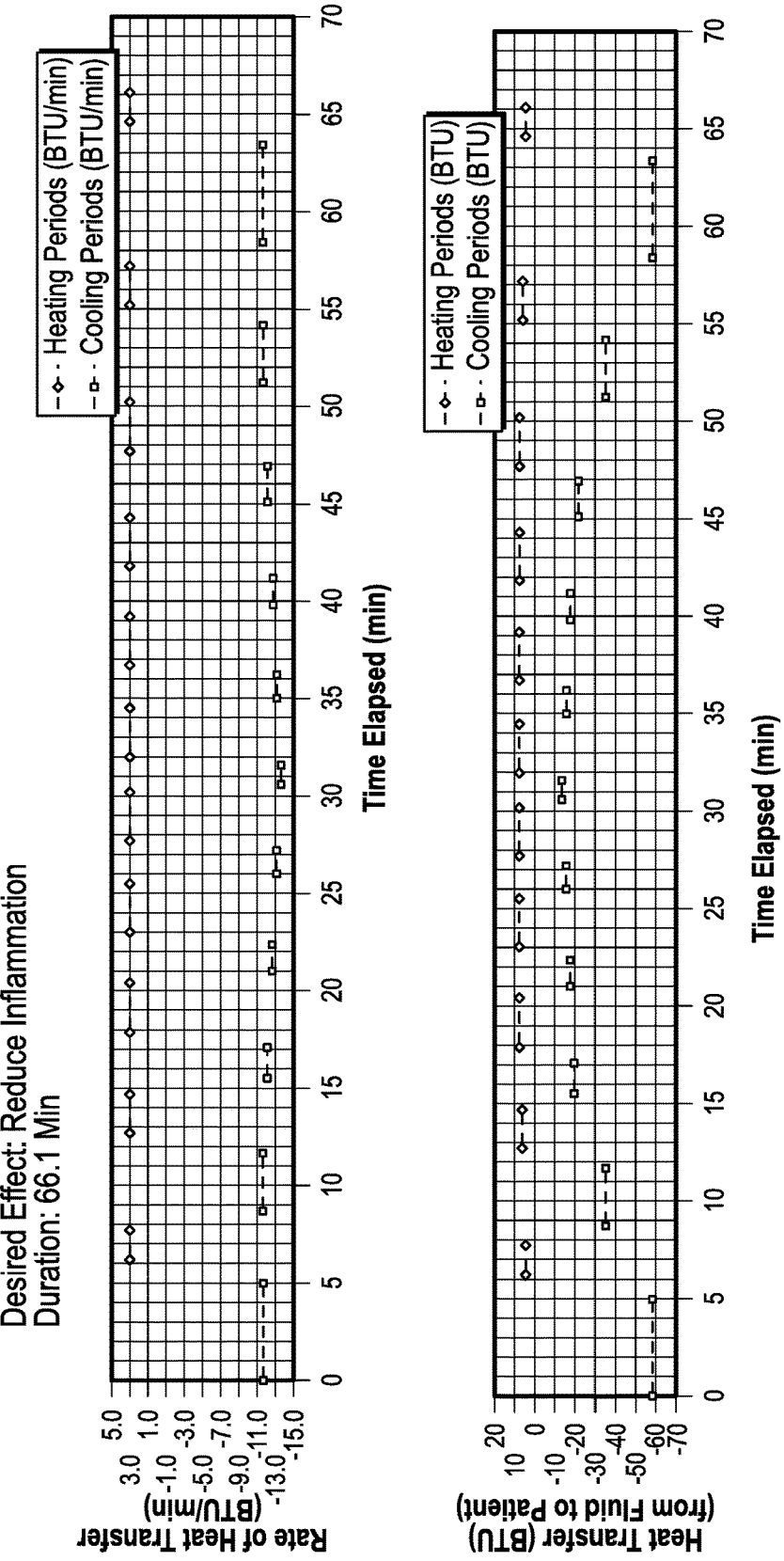

As shown in FIGS. 14E-1 and 14E-2, 14F-1 and 14F-2, and 14G-1 and 14G-2, a treatment sequence may be configured to provide a desired measure of heat transfer during the various periods of the treatment sequence. FIGS. 14E-1 and 14E-2 show an exemplary thermal contrast therapy treatment sequence configured to provide a desired measure of heat transfer during the various periods of the treatment sequence, which may be suitable for a first treatment of an athletic injury to a knee or elbow in a healthy/strong patient within the first 24 hours after the injury, to reduce inflammation. The treatment may be suitable, as an example, for an athlete with a knee injury that has occurred within 24 hours prior to treatment. The sequence shown in FIGS. 14E-1 and 14E-2 may be the first treatment of this injury, and as such the contrasting rates of heat transfer start mildly and builds up through the treatment by decreasing the temperature of the fluid cooling periods while maintaining constant temperature during the heating periods. Mid-way through the sequence, the region is allowed to calm with lesser contrast (by gradually increasing the temperature during the cooling periods), so as to reduce a sudden shock when the treatment it stopped.

Figures 1, 14F:
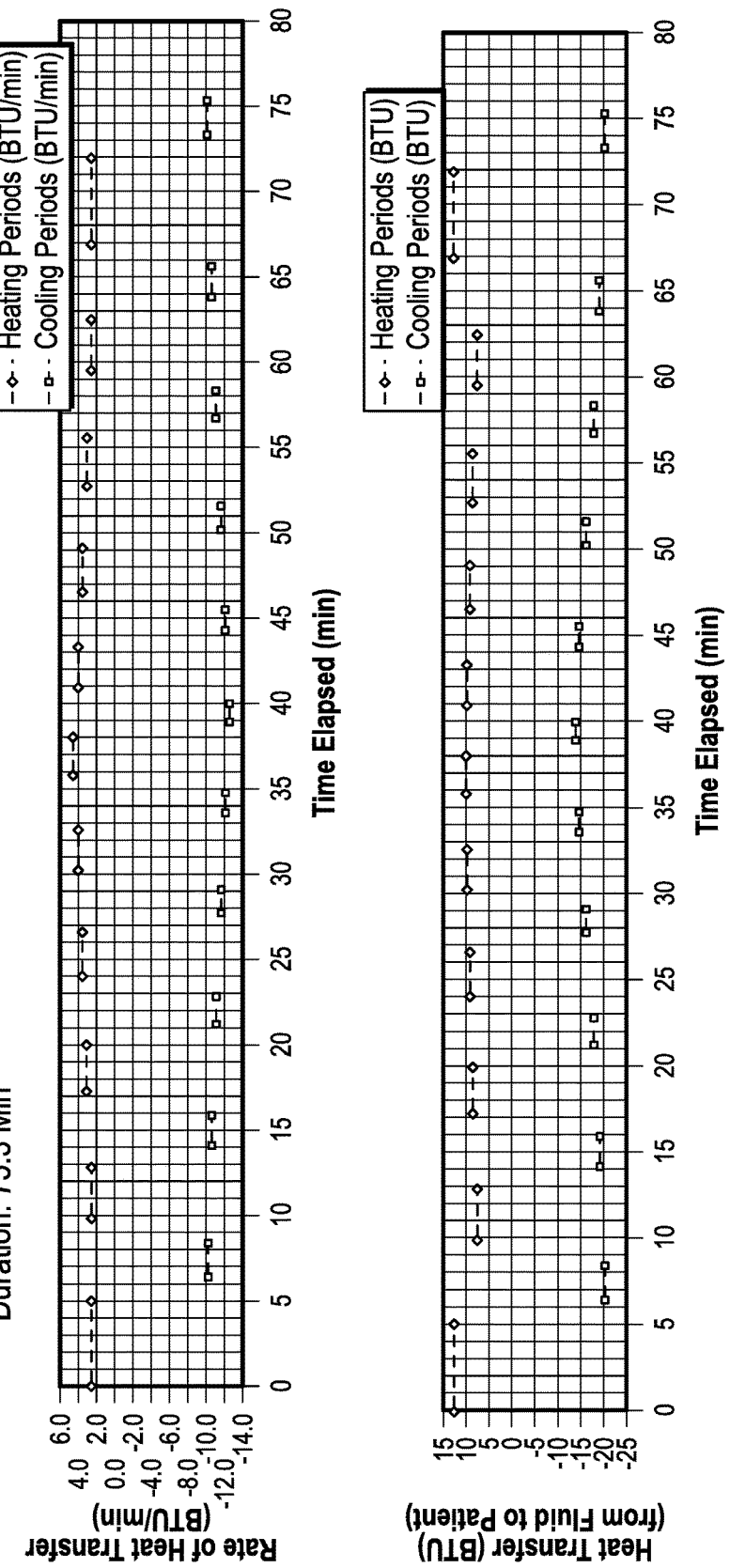

FIGS. 14F-1 and 14F-2 show an exemplary thermal contrast therapy treatment sequence configured to provide a desired measure of heat transfer during the various periods of the treatment sequence, which may be suitable for subsequent treatment of an athletic injury to a knee or elbow in a healthy/strong patient after the first 24 hours following the injury, to reduce inflammation and increase blood flow. For example, the sequence shown in FIGS. 14F-1 and 14F-2 may be provided as a subsequent treatment after previously having provided the sequence in FIGS. 14A-1 and 14A-2 or FIGS. 14E-1 and 14E-2. Here, vasodilation and vasoconstriction may be enhanced by providing a gradually increasing rate of heat transfer during the heating periods and a gradually increasing rate of heat transfer during cooling periods. Then, towards the end of the treatment sequence, the rate of heat transfer during cooling periods is gradually decreased to lessen vasoconstriction and to encourage increased blood flow in the tissue. Mid-way through the sequence, the region is allowed to calm with lesser contrast (by gradually decreasing the rate of heat transfer), so as to reduce a sudden shock when the treatment it stopped.

Figures 1, 14G:
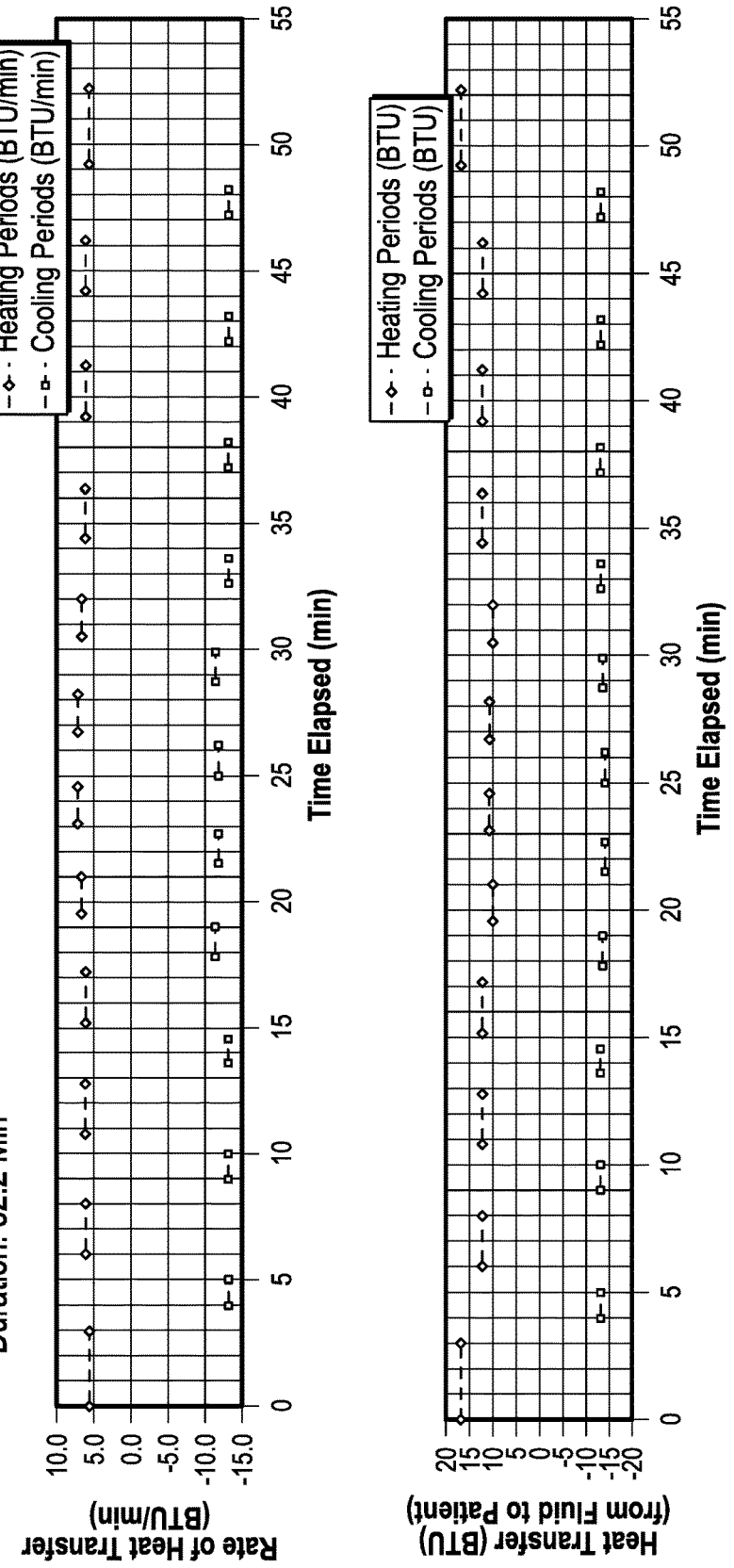

FIGS. 14G-1 and 14G-2 show an exemplary thermal contrast therapy treatment sequence configured to provide a desired measure of heat transfer during the various periods of the treatment sequence, which may be suitable for ongoing treatment during rehabilitation of an athletic injury to a knee or elbow. This sequence may be suitable for a strong/healthy patient after the first 48 hours following the injury, to reduce inflammation increase blood flow, and for pain management. For example, the sequence shown in FIGS. 14G-1 and 14G-2 may be provided as a subsequent treatment after previously having provided the sequence in FIGS. 14B-1 and 14B-2 or FIGS. 14F-1 and 14F-2. Here, rapid consecutive alteration between heating periods and cooling periods are provided, as indicated by the short transition times, and contrasting rates of heat transfer between heating periods and cooling periods are large, with such heat transfer rates intended to be at the threshold of a patient's tolerance so as to attain the maximum tolerable effect.

Each of the treatments sequences shown in FIGS. 14A-1, 14A-2 through 14G-1, 14G-2 may be modified or combined with other sequences, features, or alternative embodiments. For example, the sequences shown in FIGS. 14A-1, 14A-2 through 14D-1, 14A-2 may be configured to provide a desired measure of heat transfer during the various periods rather than a desired fluid temperature. Additionally, any of the sequences may be dynamically controlled. For example, treatment sequence parameters may be automatically adjusted to optimize a physiological parameter value, and/or to effect a desired measure of heat transfer.

In the case of treating a recent injury, one or more of the heating periods may be replaced by a neutral period. Once the swelling has been controlled, heating periods may be introduced to increase contrast and therefore increase the blood flow to that region to provide pain reduction and to further encourage healing.

In the case of a weak or elderly patient, one or more of the cooling periods may be replaced by a neutral period. As the patient becomes increasingly accustomed to thermal contrast therapy, the cooling periods may be introduced.

Those skilled in the art will appreciate that various other treatment sequences are within the scope of the present disclosure, all as may be selected based on the preference of the practitioner, therapist, or the patient receiving treatment, the area of the body sought to be treated, the particular symptom or condition sought to be treated, the particular desired therapeutic result, and/or other considerations.

III. Other Embodiments

The foregoing detailed description of illustrative embodiments has set forth various embodiments of thermal contrast therapy devices, treatment methods for providing thermal contrast therapy, and systems for providing and managing thermal contrast therapy treatments. While the devices disclosed herein may be characterized by their applicability for performing certain treatment methods disclosed herein, it will be apparent that numerous other devices may be configured to provide thermal contrast therapy. For example, in some embodiments, a thermal contrast therapy device may be configured to utilize a heat transfer medium other than a fluid. For example, particulate mediums such as cellulose particles, grains, sands, pellets, or the like may be used in a device configured to effect heat transfer through such a particulate medium. Examples of such devices include devices configured to cause fluidization of particles, such as a device having a fluidized bed component, or a device configured to cause the particulate medium to exhibit fluid-like characteristics or to be pumped using fluid type technologies. Additionally, it will be understood that alternating periods of heating and cooling may be provided through virtually any means of respectively delivering and removing heat from the treatment area, including conduction, convection, radiation, and combinations thereof. When utilizing conduction, an apparatus in physical contact with the treatment area may be provided to effect heat transfer. For example, in some embodiments, heating and/or cooling may be provided to the treatment area via thermoelectric heating and/or cooling modules, respectively. When utilizing convection, heat transfer is effected through a fluid, for example, a gas, liquid, or fluidized particles. When utilizing radiation, no heat transfer medium may be required, for example, where heat transfer is effected through electromagnetic waves.

Similarly, it will be apparent that numerous other treatment methods and treatment sequences may be provided with a thermal contrast therapy device. For example, a thermal contrast therapy device may be configured to provide only heat therapy and/or only cold therapy. Additionally, virtually any treatment sequence may be provided in accordance with the present disclosure.

The foregoing detailed description of illustrative embodiments has set forth various embodiments of thermal contrast therapy devices, treatment methods, and systems via the use of block diagrams, flowcharts, and/or examples. Insofar as such block diagrams, flowcharts, and/or examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of ordinary skill in the art in light of the present disclosure.

In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as volatile and non-volatile memory devices, floppy and other removable disks, hard disk drives, SSD drives, flash drives, optical discs (e.g., CD ROMs, DVDs, etc.), and computer memory; and transmission type media such as digital and analog communication links using TDM or IP based communication links (e.g., packet links).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control elements (e.g., feedback for sensing temperature; control heaters for adjusting temperature). A typical data processing system may be implemented utilizing any suitable commercially available components, such as those typically found in data computing/communication and/or network computing/communication systems.

The foregoing described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality. Specific examples of operably couplable include but are not limited to physically mateable and/or physically interacting components and/or wirelessly interactable and/or wirelessly interacting components and/or logically interacting and/or logically interactable components.

All of the above U.S. patents, U.S. patent application publications, U.S. patent applications, foreign patents, foreign patent applications and non-patent publications referred to in this specification and/or listed in any Application Data Sheet, are incorporated herein by reference, in their entireties.

While various aspects and embodiments have been disclosed herein, other aspects and embodiments will be apparent to those skilled in the art. The various aspects and embodiments disclosed herein are for purposes of illustration and are not intended to be limiting. It is intended that the scope of this disclosure be defined by the following claims and their equivalents:

What is claimed is:

1. A thermal contrast therapy device comprising:
   a cooling system comprising a first pump configured to circulate cold fluid through a cooling block via a cold fluid recirculation line that provides fluid communication with a cooling block inlet; and
   a heating system comprising a second pump configured to circulate hot fluid through a heating block via a hot fluid recirculation line that provides fluid communication with a heating block inlet;
   the first pump being further configured to circulate cold fluid through a treatment pad via an outflow fluid line while the second pump circulates hot fluid through the heating block with at least a portion of said hot fluid bypassing the treatment pad via the hot fluid recirculation line; and
   the second pump being further configured to circulate hot fluid through the treatment pad via the outflow fluid line while the first pump circulates cold fluid through the cooling block with at least a portion of said cold fluid bypassing the treatment pad via the cold fluid recirculation line.

2. The thermal contrast therapy device of claim 1, wherein the cooling system further comprises a cold fluid feed line configured to provide fluid communication between a cooling block outlet and the first pump; and/or
   wherein the heating system further comprises a hot fluid feed line configured to provide fluid communication between a heating block outlet and the second pump.

3. The thermal contrast therapy device of claim 1, wherein the cooling system and the heating system converge at the outflow fluid line.

4. The thermal contrast therapy device of claim 1, wherein the device is configured to provide a sequence of alternating cooling periods and heating periods, the periods in the sequence each having a duration of between about 15 seconds to 300 seconds.

5. The thermal contrast therapy device of claim 1, wherein the device is configured to provide a sequence of alternating cooling periods and heating periods, the periods in the sequence each having a duration of between about 5 minutes to 20 minutes.

6. The thermal contrast therapy device of claim 1, wherein the device is configured to provide a sequence comprising a continuous cyclical change in fluid temperature and/or rate of heat transfer.

7. The thermal contrast therapy device of claim 6, wherein the device is configured to synchronize the frequency of the pressure pulse with the heart rate of a patient receiving treatment.

8. The thermal contrast therapy device of claim 1, wherein the device is configured to effect a pressure pulse in a treatment pad, the pressure pulse effected at least in part by alternating a valve between opened and closed positions.

9. The thermal contrast therapy device of claim 1, wherein the device is configured to provide hot fluid ranging from about 85° F. to 130° F.

10. The thermal contrast therapy device of claim 1, wherein the device is configured to provide cold fluid ranging from about 30° F. to 70° F.

11. The thermal contrast therapy device of claim 1, further comprising a shared reservoir configured to hold a volume of fluid to supply both the heating system and the cooling system.

12. The thermal contrast therapy device of claim 11, wherein the device is configured to circulate cold fluid through the cooling system, via a loop excluding the shared reservoir, the heating system, and the treatment pad; and/or to circulate hot fluid through the heating system, via a loop excluding the shared reservoir, the cooling system, and the treatment pad.

13. A thermal contrast therapy device comprising:
   a cooling system configured to circulate cold fluid through a treatment pad via an outflow fluid line;
   a heating system configured to circulate hot fluid through the treatment pad via the outflow fluid line; and
   a shared reservoir configured to hold a volume of fluid to supply both the heating system and the cooling system;
   wherein fluid gravity feeds from the shared reservoir to the cooling system via a first supply line, and from the shared reservoir to the heating system via a second supply line, and
   wherein the first supply line interfaces with the shared reservoir through a first opening, and the second supply line interfaces with the shared reservoir through a second opening, the first opening located at an elevation below the elevation of the second opening.

14. The thermal contrast therapy device of claim 13, wherein the device is configured to allow the shared reservoir to hold a substantially constant volume of fluid during a sequence of alternating cooling periods and heating periods.

15. The thermal contrast therapy device of claim 13, wherein the first opening being located at an elevation below the elevation of the second opening is effective, at least in part, to allow stratification of hot fluid and cold fluid in the shared reservoir and for the heating system to preferentially draw stratified hot fluid from the shared reservoir and/or the cooling system to preferentially draw stratified cold fluid from the shared reservoir.

16. The thermal contrast therapy device of claim 13, wherein the shared reservoir is configured to keep the cooling system and the heating system substantially filled with fluid.

17. The thermal contrast therapy device of claim 13, wherein the shared reservoir is configured to receive:
   fluid from the cooling system via the first supply line, when a volume of fluid from the treatment pad and/or the heating system displaces a corresponding volume of fluid in the cooling system, the first supply line being configured to allow displaced fluid from the cooling system to backflow into the shared reservoir; and fluid from the heating system via the second supply line, when a volume of fluid from the treatment pad and/or the cooling system displaces a corresponding volume of fluid from the heating system, the second supply line being configured to allow displaced fluid from the heating system to backflow into the shared reservoir.

18. The thermal contrast therapy device of claim 13, wherein the device is configured to circulate cold fluid through the cooling system, via a loop excluding the shared reservoir, the heating system, and the treatment pad; and/or to circulate hot fluid through a heating block, via a loop excluding the shared reservoir, the cooling system, and the treatment pad.

19. The thermal contrast therapy device of claim 13, wherein the device further comprises a temperature sensor configured to ascertain the temperature of the fluid, and wherein the device is configured to route circulating fluid either to the heating system and/or the cooling system based, at least in part, on an ascertained temperature.

20. The thermal contrast therapy device of claim 13, wherein the device is configured to provide hot fluid ranging from about 85° F. to 130° F.

21. The thermal contrast therapy device of claim 13, wherein the device is configured to provide cold fluid ranging from about 30° F. to 70° F.

22. A thermal contrast therapy device comprising:
a cooling system configured to circulate cold fluid through a treatment pad via an outflow fluid line;
a heating system configured to circulate hot fluid through the treatment pad via the outflow fluid line; and
a shared reservoir configured to hold a volume of fluid to supply both the heating system and the cooling system;
wherein fluid gravity feeds from the shared reservoir to the cooling system via a first supply line, and from the shared reservoir to the heating system via a second supply line, and the shared reservoir is configured to receive:
fluid from the cooling system via the first supply line, when a volume of fluid from the treatment pad and/or the heating system displaces a corresponding volume of fluid in the cooling system, the first supply line being configured to allow displaced fluid from the cooling system to backflow into the shared reservoir; and
fluid from the heating system via the second supply line, when a volume of fluid from the treatment pad and/or the cooling system displaces a corresponding volume of fluid from the heating system, the second supply line being configured to allow displaced fluid from the heating system to backflow into the shared reservoir.

23. A thermal contrast therapy device comprising:
a cooling system configured to circulate cold fluid through a treatment pad via an outflow fluid line;
a heating system configured to circulate hot fluid through the treatment pad via the outflow fluid line; and
a shared reservoir configured to hold a volume of fluid to supply both the heating system and the cooling system;
wherein the device is configured to circulate cold fluid through the cooling system, via a loop excluding the shared reservoir, the heating system, and the treatment pad; and/or to circulate hot fluid through a heating block, via a loop excluding the shared reservoir, the cooling system, and the treatment pad.

* * * * *